United States Patent [19]
Vlasselaer

[11] Patent Number: 5,663,051
[45] Date of Patent: *Sep. 2, 1997

[54] SEPARATION APPARATUS AND METHOD

[75] Inventor: Peter Van Vlasselaer, Sunnyvale, Calif.

[73] Assignee: Activated Cell Therapy, Inc., Mountain View, Calif.

[*] Notice: The term of this patent shall not extend beyond the expiration date of Pat. No. 5,474,687.

[21] Appl. No.: 570,397

[22] Filed: Dec. 11, 1995

Related U.S. Application Data

[63] Continuation-in-part of Ser. No. 299,469, Aug. 31, 1994, Pat. No. 5,474,687, Ser. No. 299,468, Aug. 31, 1994, Ser. No. 299,467, Aug. 31, 1994, and Ser. No. 299,465, Aug. 31, 1994.

[51] Int. Cl.$^6$ .................................................. G01N 33/574
[52] U.S. Cl. ..................... 435/7.23; 210/781; 210/782; 215/309; 220/501; 220/503; 220/563; 220/564; 422/72; 422/101; 422/102; 435/2; 435/7.21; 435/7.24; 435/803; 436/514; 436/518; 436/527; 436/824
[58] Field of Search ...................... 422/72, 101, 102; 220/501, 503, 563, 564; 215/309; 210/781, 782; 435/2, 7.21, 7.23, 7.24, 803; 436/514, 518, 527, 824

[56] References Cited

U.S. PATENT DOCUMENTS

| | | |
|---|---|---|
| 3,441,205 | 4/1969 | Young, Jr. . |
| 3,513,976 | 5/1970 | James . |
| 3,706,305 | 12/1972 | Berger et al. ............... 128/762 |
| 3,706,306 | 12/1972 | Berger et al. ............... 128/762 |
| 3,750,645 | 8/1973 | Bennett et al. ............. 128/760 |

(List continued on next page.)

FOREIGN PATENT DOCUMENTS

| | | |
|---|---|---|
| 0595641A2 | 10/1993 | European Pat. Off. . |
| 24494 | of 1913 | United Kingdom . |
| 605467 | 7/1948 | United Kingdom . |
| WO91/07660 | 5/1991 | WIPO . |
| WO93/08268 | 4/1993 | WIPO . |
| WO93/08269 | 4/1993 | WIPO . |

OTHER PUBLICATIONS

Dicke, et al., "The Selective Elimination of Immunologically Competent Cells from Bone Marrow and Lymphatic Cell Mixtures," *Transplationation* 6(4):562–570 (1968).

Dicke, et al., "Avoidance of Acute Secondary Disease by Purification of Hemopoietic Stem Cells with Density Gradient Centraifugation." *Exp. Hematol.* 20:126–130 (1970).

Dicke, et al., "Allogenic Bone Marrow Transplantation After Elimination of Immunocompetent Cells by Means of Density Gradient Centrifugation," *Transplant. Proc.* 3(1):666–668 (1971).

Wallach, et al., "Affinity Density Perturbation: A New Fractionation Principle and Its Illustration in a Membrane Separation." *FEBS Letters* 21(1):29–33 (1972).

(List continued on next page.)

*Primary Examiner*—Donald E. Adams
*Assistant Examiner*—Susan C. Wolski
*Attorney, Agent, or Firm*—Carol A. Stratford

[57] ABSTRACT

Disclosed is an apparatus designed to be used for enriching specific cell types from cell mixtures. The apparatus includes a centrifugable device that includes a constriction defining a lower region and a defined cell separation medium. The constriction prevents mixing between the upper and lower portions of the device. Also disclosed are methods that use precisely defined cell separation media to isolate specific cells from cell mixtures, including CD34$^+$ hematopoietic progenitor cells from blood or bone marrow, nucleated fetal cells from maternal blood, specific tumor cells, dendritic cells, natural killer cells, and natural suppressor cells from various body fluids, and for enrichment or depletion of T cell lymphocytes. Also disclosed is a density adjusted cell separation technique used to augment the above apparatus and enrichment methods. The apparatus and enrichment methods are useful in various diagnostic and therapeutic regimens.

41 Claims, 19 Drawing Sheets

U.S. PATENT DOCUMENTS

| | | | |
|---|---|---|---|
| 3,849,072 | 11/1974 | Ayres | 210/789 |
| 3,862,303 | 1/1975 | Anderson | 436/531 |
| 3,937,211 | 2/1976 | Merten | 128/765 |
| 3,957,654 | 5/1976 | Ayres | 210/516 |
| 3,957,741 | 5/1976 | Rembaum et al. | 526/312 |
| 3,965,889 | 6/1976 | Sachs | 128/764 |
| 3,985,122 | 10/1976 | Topham | 128/765 |
| 4,001,122 | 1/1977 | Griffin | 210/516 |
| 4,020,831 | 5/1977 | Adler | 128/765 |
| 4,022,576 | 5/1977 | Parker | 436/177 |
| 4,035,316 | 7/1977 | Yen et al. | 521/65 |
| 4,040,959 | 8/1977 | Berman et al. | 210/782 |
| 4,055,501 | 10/1977 | Cornell | 210/516 |
| 4,066,414 | 1/1978 | Selby | 422/102 |
| 4,105,598 | 8/1978 | Yen et al. | 521/53 |
| 4,112,924 | 9/1978 | Ferrara et al. | 128/764 |
| 4,134,512 | 1/1979 | Nugent | 215/247 |
| 4,147,628 | 4/1979 | Bennett et al. | 210/789 |
| 4,152,270 | 5/1979 | Cornell | 210/516 |
| 4,181,700 | 1/1980 | Chervenka et al. | 422/102 |
| 4,213,456 | 7/1980 | Bottger | 604/226 |
| 4,256,120 | 3/1981 | Finley | 128/764 |
| 4,378,812 | 4/1983 | Sarstedt | 128/765 |
| 4,443,345 | 4/1984 | Wells | 210/782 |
| 4,459,997 | 7/1984 | Sarstedt | 128/764 |
| 4,510,244 | 4/1985 | Parks et al. | 435/172.2 |
| 4,511,349 | 4/1985 | Nielsen et al. | 494/16 |
| 4,511,662 | 4/1985 | Baran et al. | 436/513 |
| 4,533,468 | 8/1985 | Ensor et al. | 209/172 |
| 4,562,844 | 1/1986 | Carpenter et al. | 128/675 |
| 4,569,764 | 2/1986 | Satchell | 210/511 |
| 4,610,846 | 9/1986 | Martin | 422/101 |
| 4,707,276 | 11/1987 | Dodge et al. | 210/789 |
| 4,710,472 | 12/1987 | Saur et al. | 435/308.1 |
| 4,777,145 | 10/1988 | Luotola et al. | 436/526 |
| 4,824,560 | 4/1989 | Alspector | 209/208 |
| 4,828,716 | 5/1989 | McEwen et al. | 210/740 |
| 4,844,818 | 7/1989 | Smith | 210/789 |
| 4,886,071 | 12/1989 | Mehl et al. | 128/760 |
| 4,917,801 | 4/1990 | Luderer et al. | 210/516 |
| 4,927,749 | 5/1990 | Dorn | 435/2 |
| 4,927,750 | 5/1990 | Dorn | 435/2 |
| 4,954,264 | 9/1990 | Smith | 210/782 |
| 4,957,638 | 9/1990 | Smith | 210/782 |
| 4,983,369 | 1/1991 | Barder et al. | 423/338 |
| 5,030,341 | 7/1991 | McEwen et al. | 210/94 |
| 5,030,559 | 7/1991 | Nicolson et al. | 435/7.23 |
| 5,039,401 | 8/1991 | Columbus et al. | 210/177 |
| 5,045,201 | 9/1991 | Dubuois et al. | 210/502.1 |
| 5,053,134 | 10/1991 | Luderer et al. | 210/516 |
| 5,132,232 | 7/1992 | Parker | 436/177 |
| 5,236,604 | 8/1993 | Fiehler | 210/782 |
| 5,248,480 | 9/1993 | Greenfield et al. | 422/68.1 |
| 5,260,186 | 11/1993 | Cercek et al. | 435/2 |
| 5,269,927 | 12/1993 | Fiehler | 210/516 |
| 5,271,852 | 12/1993 | Luoma, II | 210/789 |
| 5,279,936 | 1/1994 | Vorpahl | 435/6 |
| 5,308,506 | 5/1994 | McEwen | 210/745 |
| 5,474,687 | 12/1995 | Van Vlasselaer | 210/782 |

OTHER PUBLICATIONS

Dicke, et al., "The Use of Stem Cell Concentrates as Bone Marrow Grafts in Man," *Transplant. Proc.* 5(1):909–912 (1973).

Korbling, et al., "Procurement of Human Blood Stem Cells by Continuous–Flow Centrifugation–Further Comment," *Blood* 50:753–754 (1977).

Korbling, et al., "In–Vitro and In–Vivo Properties of Canine Blood Mononuclear Leukocytes Separated by Discontinuous Albumin Density Gradient Centrifugation," *Biomedicine* 26:275–283 (1977).

Herzenberg, et al., "Fetal Cells in the Blood of Pregnant Women: Detection and Enrichment by Fluorescence–Activated Cell Sorting," *Proc. Natl. Acad. Sci. USA* 76:1453–1455 (1979).

Olofsson, et al., "Separation of Human Bone Marrow Cells in Density Gradients of Polyvinylpyrrolidone Coated Silica Gel (Percoll)," *Second J. Heematol.* 24:254–262 (1980).

Osborne, et al., "The Value of Estrogen and Progresterone Receptors in the Treatment of Breast Cancer," *Cancer* 46(12:2884–2888 (1980).

Westley, et al., "An Estrogen–Induced Protein Secreted by Human–Breast Cancer–Cells in Culture," *Eur. J. Cell Biol.* 22(1):397 (1980).

Gerdes, et al., "Production of a Mouse Monoclonal Antibody Reactive with a Human Nuclear," *Current Biotech Abs.* (1983).

Ellis, et al., "The Use of Discontinuous Percoll Gradients to Separate Populations of Cells from Human Bone Marrow and Peripheral Blood," *J. Immunolog. Meth.* 66:9–16 (1984).

Kufe, et al., "Differential Reactivity of a Novel Monoclonal Antibody (DF3) with Human Malignant Vs. Benign Breast Tumors," *Hybridoma* 3(3):223–232 (1984).

Lasky, et al., "Size and Density Characterization of Human Committed and Multipotent Hematopoietic Progenitors," *Exp. Hematol.* 13:680–684 (1985).

Martin, et al., "Purification of Haemopoietic Progenitor Cells from Patients with Chronic Granulocytic Leukaemia Using Percoll Density Gradients and Elutriation," *Brit. J. Haematol.* 63:183–198 (1986).

Bray, et al., "Serum Levels and Biochemical Characteristics of Cancer–Associated Antigen CA–549, a Circulating Breast Cancer Marker," *Cancer Res.* 47(22):5853–5860 (1987).

Blanchard, et al., "Infiltration of Interleukin–2–Inducible Killer Cells in Ascitic Fluid and and Plaural Effusions of Advanced Cancer Patients," *Cancer Res.* 48:6321–6327 (1988).

Bianchi, et al., "Isolation of Fetal DNA from Nucleated Erythrocytes in Maternal Blood," *Proc. Natl. Acad. Sci. USA* 87:3279–3283 (1990).

"The CD System," Dako, Inc. (1990).

Price, et al., "Prenatal Diagnosis with Fetal Cells Isolated from Maternal Blood by Multiparameter Flow Cytometry," *Am. J. Obstet. Gynecol.* 165(6, part 1):1731–1737 (1991).

Shpall, et al., "Immunomagnetic Purging of Breast Cancer from Bone Marrow for Autologous Transplantation," *Bone Marrow Transplant.* 7:145–151 (1991).

Yoshioka, et al., "Immobilization of Ultra–Thin Layer of Monoclonal Antibody on Glass Surface," *J. Chromolography* 566:361–368 (1991).

Durrant, et al., "A Rapid Method for Separating Tumour Infiltrating Cells and Tumour Cells from Colorectal Tumours," *J. Immunol. Meth.* 147:57–64 (1992).

Elias, et al., Session 12: Plenary Session, "Prenatal Diagnosis of Aneuploidy Using Fetal Cells Isolated from Maternal Blood," *Am. J. Hum. Genet.* 51:A4, Excerpt 5 (1992).

Ganshirt–Ahlert, et al., Session 34: Prenatal and Perinatal Genetics II, and Molecular Applications in Clinical Genetics III, "Noninvasive Prenatal Diagnosis," *Am. J. Hum. Genet.* 51:A48, Excerpt 182 (1992).

Ganshirt–Ahlert, et al., "Magnetic Cell Sorting and the Transferring Receptor as Potential Means of Prenatal Diagnosis from Maternal Blood," *Am. J. Obstet. Gynecol.* 166(5):1350–1355 (1992).

Hall, et al., Prenatal and Perinatal Genetics: "Isolation and Purification of CD34+ Fetal Cells from Maternal Blood," *Am. J. Hum. Genet.* 51:A257, Excerpt 1013 (1992).

Harrison, et al., Prenatal and Perinatal Genetics: "Use of Fluorescence in situ Hybridization to Detect Confined Placental Mosaicism in Trisomic Conceptions," *Am. J. Hum. Genet.* 51:A527, Excerpt 1014 (1992).

Holzgreve, et al., "Fetal Cells in the Maternal Circulation," *J. Reprod. Med.* 37(5):410–418 (1992).

Ikuta, et al., "Lymphocyte Development from Stem Cells," *Ann. Rev. Immunol.* 10:759–783 (1992).

Julien, et al., Session 34: Prenatal and Perinatal Genetics II, and Molecular Applications in Clinical Genetics III, "Fetal Cells in Maternal Blood," *Am. J. Hum. Genet.* 51:A48, Excerpt 181 (1992).

Lebkowski, et al., "Rapid Isolation of Human CD34 Hematopoietic Stem Cells Purging of Human Tumor Cells," *Transplantation* 53(5):1011–1019 (1992).

Russo, et al., *The Use of Resealed Erythrocytes as Carriers and Bioreactors* (Magnani & DeLoach, Eds.), Plenum Press, New York, NY, pp. 101–107 (1992).

Pope, et al., "New Application of Silane Coupling Agents for Covalently Binding Antbodies to Glass and Cellulose Solid Supports," *Bioconjugate Chem.* 4:166–171 (1993).

Schmitz, et al., "Optimizing Follicular Dendritic Cell Isolation by Discontinuous Gradient Centrifugation and Use of the Magnetic Cell Sorter (MACS)," *J. Immunological Meth.* 139:189–196 (1993).

Simpson, et al., "Isolating Fetal Cells from Maternal Blood, Advances in Prenatal Diagnosis Through Molecular Technology," *JAMA* 270(19):2357–2361 (1993).

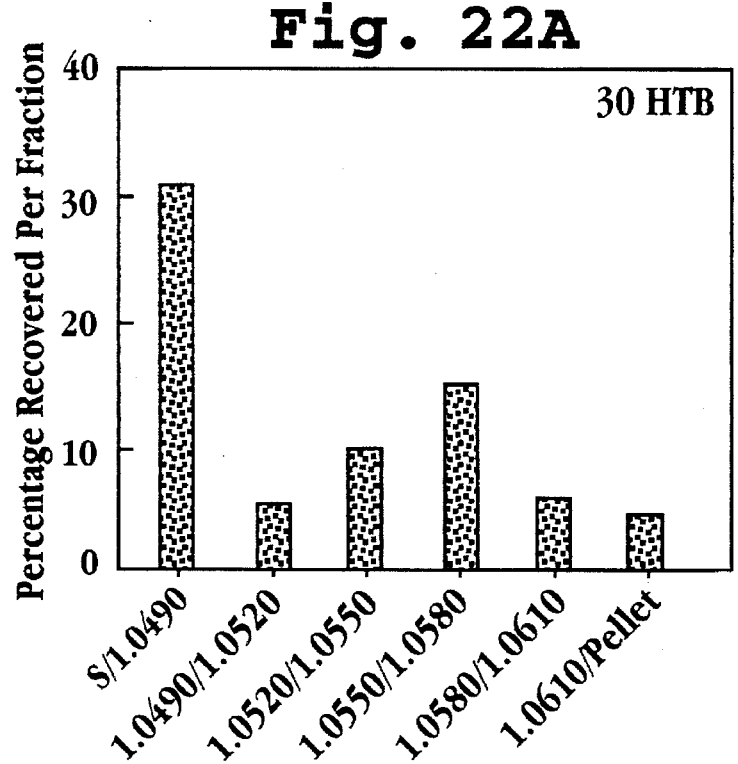
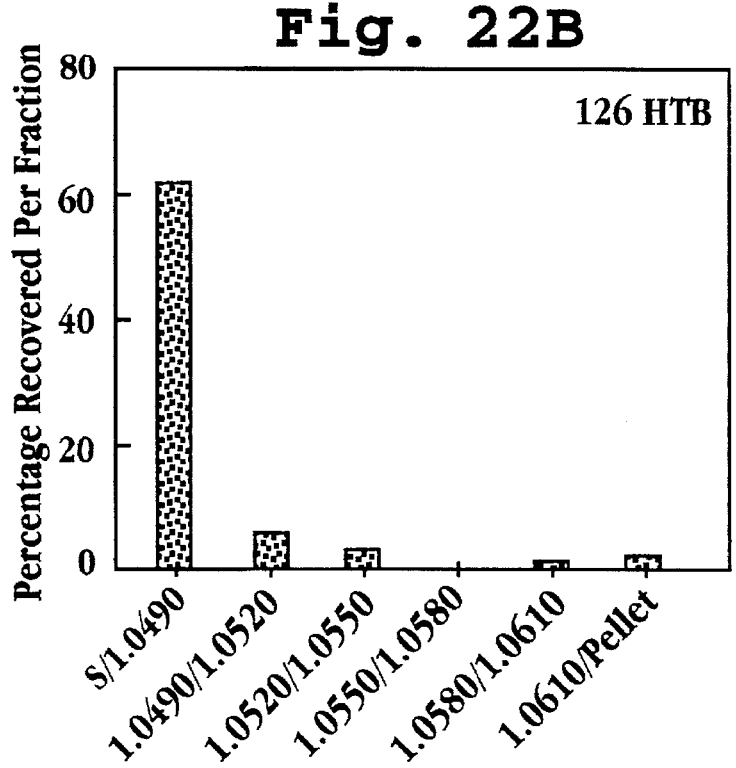

SEPARATION APPARATUS AND METHOD

This is a continuation-in-part of U.S. patent application Ser. No. 08/299,469 now U.S. Pat. No. 5,474,687, and a continuation-in-part of application Ser. No. 08/299,465, U.S. Ser. No. 08/299,467 and U.S. Ser. No. 08/299,468, all filed Aug. 31, 1994.

1. FIELD OF THE INVENTION

The present invention relates to an apparatus designed for separating cell populations. In particular, the apparatus includes a cell-trap centrifugation apparatus which contains a defined density medium for separating lower density cells from cell populations. The invention also includes a method of enriching for a desired cell population from cell sources. The method may be augmented by selectively increasing the densities of unwanted low density cells using microparticles having covalently attached cell attachment molecules.

2. BACKGROUND

Isolating specific cell types is often desirable for clinical diagnostic and therapeutic applications. In the clinical diagnostics field, there is a need, for example, for morphological analysis of tumor cells, fetal karyotyping, and tissue typing procedures. Therapeutically, there is a need, for example, for purging cells or tissues intended for use in autologous cellular or tissue transfusions or transplantations, e.g. purging tissues of viral antigens and tumor cells. There is also a need for enriching or isolating desirable cells for use in transplantations, e.g. for use in ex vivo expansion of hematopoietic cells intended for allogeneic and autologous transplantation, and for the use in adoptive immunotherapy of potent antigen presenting cells (dendritic cells), cytotoxic T lymphocytes, natural killer (NK) cells and natural suppressor cells.

Several methods are known in the art for separating desirable cells from body fluids. Such methods include separating cells based upon buoyant density in a cell separation composition (U.S. Pat. No. 4,927,750), separating serological factors on density gradients using latex beads coated with antiserological factor (U.S. Pat. No. 3,862,303), separating cells through the use of a magnetic field (U.S. Pat. No. 4,777,145), and separating T and B cells on density gradients (U.S. Pat. No. 4,511,662). Cell separation methods known in the art may have the disadvantage of cell loss due to the sticking of cells to tubes and pipettes.

There is need for rapid and efficient means of isolating relatively rare populations of cells for diagnostic and therapeutic procedures. The present invention fills this need by providing methods of isolating or enriching minor populations of desirable cells from cell sources or mixtures containing multiple cell populations. Moreover, the invention provides for collection of enriched cells in a high yield.

Specifically, it is the discovery of the present invention that by providing highly defined cell separation media having precisely measured specific densities, specific, defined populations of cells can be isolated and/or depleted. Moreover, the invention provides a cell-trap centrifugation apparatus that greatly enhances collection and allows the automation of this process. Alternatively or in addition, the process is enhanced by use of a density adjusted cell sorting (DACS) step to provide a higher level of specificity to the separation process. The invention also provides specific methods for isolation of specific cell types that are important in diagnostic and therapeutic methods—including fetal nucleated cells, hematopoietic progenitor (CD34$^+$) cells, selected tumor cells, dendritic cells, NK cells, cytotoxic T-lymphocyte (CTL) and natural suppressor cells. The invention also provides for the depletion of cell types that may interfere with a particular clinical outcome—including, in some cases CTL.

3. SUMMARY OF THE INVENTION

In one aspect, the invention is directed to a cell-separation apparatus useful in isolation of cells by density methods. The apparatus includes a centrifugation device, which may be a tube, a bucket, a bag or other centrifugable container. The device has a constricted region situated longitudinally within the device that is constructed and positioned to retain fluid in the bottom portion of the container when it is inverted. This feature permits decantation of the tube without substantial mixing of contents between compartments. The constriction preferably defines one or more downwardly sloped surfaces having lower edge regions defining an opening, which may be any shape, or which may form a plurality of openings, so long as it operates to retain fluid upon inversion. In a preferred embodiment, the constriction is an annular ring. Preferably, the annulus is constructed for forced fit into the tube for variable positioning within the tube.

The apparatus also includes a cell separation medium contained in the bottom portion of the tube. The medium is present in the tube to a level above the opening formed by the constriction. In this way, cells that are captured at an interface between the cell-separation medium and a lower density cell-loading medium can be discharged with the lower-density medium when the tube is inverted, without mixing with the contents of the bottom portion of the tube.

In a more specific embodiment, the centrifuge apparatus includes a tube with an annular member disposed therein. The annular member defines an opening having an area less than the area of a cross section of the tube. The annular member may be integrally formed in the tube, or it may be movable along the internal length of the tube, for adjustment of volumes. The tube also contains a density gradient solution which fills the lower portion and a part of the upper portion of the tube to a level at least above the opening in the annular member. For isolation of a specific cell type, the density gradient solution is isotonic with the specific cells and has a specific density within 0.0005 gr/ml of the specific density of the desired cells. In another embodiment, the density gradient material will preferably be isotonic with the cells. By isotonic is meant that the solution has an osmolality that is within the range tolerated by the cell, usually about 280–340 mOsm/kgH$_2$O, and preferably, for human cells, about 280 mOsm/kgH$_2$O, depending on the cell type and source.

Specific embodiments of the apparatus of the invention include a closed system, which may include a centrifuge bucket, as described below, a centrifuge syringe or a centrifugable bag, as discussed herein. In one preferred embodiment, the device takes the form of a centrifuge bucket having a constriction member and a closed top. Ports in the top serve as conduits for introduction of fluid into the device, which may also include a port that communicates to the bottom portion of the tube. Additionally, this embodiment is adaptable for use as a culture flask for culturing cells isolated within. Alternatively, another embodiment of the apparatus of the invention is a centrifugable syringe described herein. The syringe includes a plunger with a constricted region that forms a fluid receiving space in the syringe bottom similar to the fluid receiving space formed by the constriction in the above-described tube apparatus.

The invention also includes the above-described apparatus in specific configurations defined for isolation or enrichment of specific cell types. For isolation of specific rare blood cells, defined as cells constituting less than or equal to about 1% of a blood cell mixture, the apparatus includes cell separation medium that is characterized by a physiological osmolality and a specific density that is within at least ±0.005 gr/ml, and preferably within at least ±0.0002 gr/ml of the specific density of the desired cells. In preferred embodiments, for isolation of CD34+ hematopoietic progenitor cells from bone marrow the medium will preferably have a specific density of 1.0685±0.0005 gr/ml; for isolation of fetal nucleated cells from maternal blood the medium will preferably have a specific density of 1.0720±0.0005 gr/ml; for isolation of tumor cells, the separation medium will have a specific density selected from the range 1.0490–1.0580 gr/ml, and more preferably, 1.0580 gr/ml, for isolation of certain breast tumor cells; for the isolation of natural killer cells or natural suppressor cells, the separation medium will have a specific density of 1.0605±0.0005 gr/ml; and for the isolation of dendritic cells or cytotoxic T cells, using a three-step process described herein, the medium will have a specific density of 1.0720±0.0005, 1.0610±0.0005, or 1.0565±0.0005 gr/ml, as well as methods for isolating tumor cells for diagnostic purposes, and methods of depleting T cell lymphocytes from a cell mixture.

In a related embodiment, the invention includes methods of isolating selected cells from cell mixtures, according using the above-defined apparatus. The method includes adding a cell mixture to the apparatus, centrifuging the apparatus at a gravitational force sufficient to pellet cells having specific densities greater than the specific density of the cell separation medium in the apparatus and collecting selected cells from the upper portion of the tube. According to preferred embodiments of this aspect of the invention, the specific density of the cell separation medium present in the apparatus will be tailored to the individual cell type to be isolated, as described above.

The method of the invention further includes, in specific embodiments, methods of isolating or enriching certain rare blood cell types, exemplified by CD34+ hematopoietic progenitor cells, breast tumor cells, fetal nucleated cells, dendritic cells, natural killer cells, natural suppressor cells and T-cell lymphocytes, from cell mixtures. Based on the applicant's discovery that highly defined media can be used to isolate specific cell types, the invention includes using the specific density and osmolality conditions described above, i.e., using media defined to ±0.0005, or preferably to ±0.0002 gr/ml, to isolate cells in a single specific density medium. CD34+ cells that can be isolated include colony forming cells and cells with long term culture initiating capacity. According to this aspect of the invention, such cells are preferably isolated from bone marrow cell mixtures, but may also be isolated from fetal umbilical cord blood or from peripheral blood. Fetal nucleated cells include nucleated red blood cells and trophoblasts. In other preferred embodiments, the invention includes a method of isolating natural killer cells or natural suppressor cells using a medium having a density of 1.0605±0.0005 gr/ml.

In yet another embodiment, the various isolation methods of the invention includes incubating the cell mixture from which cells are to be isolated with cell type-specific binding agents that are linked to or that are capable of binding to carrier particles, prior to centrifuging the cells through cell separation medium. Such carrier particles may be formed of a variety of materials, but, in preferred embodiments are formed of silane-activated silica, and preferably 3-aminopropyltriethoxy silane-activated silica. In a preferred embodiment, the particles will have a specific density that is at least 0.001 gr/ml greater than the specific density of said cell separation medium, for sedimentation of unwanted cells to which the binding agents are directed. Binding agents used in this aspect of the invention may include antibodies, lectins, cytokines and the like. For example, a specific binding agent that is useful in depleting leukocytes is mouse anti-CD45 antibody. Such a binding agent can be directed to the cells, and later or simultaneously bound to a carrier particle through another linking molecule that binds the binding agent—such as an anti-mouse IgG antibody attached to the carrier particle. In the case of antibody binding or linking agents, the invention also recognizes that nonspecific binding of cells to the binding agent is reduced, when the glycosylation of the Fc portion of the antibody is prevented from contacting such cells—for example, by adding polyethylene glycol to the formulation or by using an Fab fragment of the antibody.

In preferred embodiments of this feature of the invention, cell mixtures can be depleted of selected tumor cells by using carrier particles to which appropriate tumor antigen recognizing molecules are attached. For example, B-cell lymphoma tumor cells can be depleted from a cell mixture using binding agents that bind CD-9, CD-10, CD-19 and/or CD-20 antigens; breast tumor cells can be depleted using Her2/Neu or estrogen receptor binding agents.

The foregoing cell-type specific binding agents are conveniently carried out in a kit, that forms another related aspect of the invention. The kit includes a cell-trap apparatus, as described above, in combination with cell-type specific binding agent and carrier particles.

Alternatively, the specific binding agents can be directed to the cells of interest for selective sedimentation thereof.

In a related embodiment, the invention includes a method for depleting cytotoxic T lymphocytes from a cell mixture, particularly one that also includes hematopoietic progenitor CD34+ cells. The method includes layering the cell mixture onto a cell separation medium that is isotonic with the T lymphocyte and having a specific density of less than 1.0070±0.0005 gr/ml. For depleting specific preparations, the invention recognizes that this density can be defined with more particularity—when depleting peripheral blood preparations from which hematopoietic progenitor cells are to be isolated, the preferred specific density is 1.0605±0.0005 gr/ml; when depleting bone marrow cell preparations, the preferred specific density is 1.0685±0.0005 gr/ml; and when depleting dendritic cell preparations, the preferred specific density is 1.0650±0.0005 gr/ml. It is further recognized that such depleted T lymphocytes can be isolated from the pellet of the depleted cell preparation, in accordance with the invention, for used in certain types of adoptive immunotherapy.

4. BRIEF DESCRIPTION OF THE DRAWINGS

FIGS. 1A–C show cross-sectional views of a centrifugation apparatus of the invention, illustrating the steps of isolating or separating cells according to one of the methods of the invention;

Figures 5A, 5B:
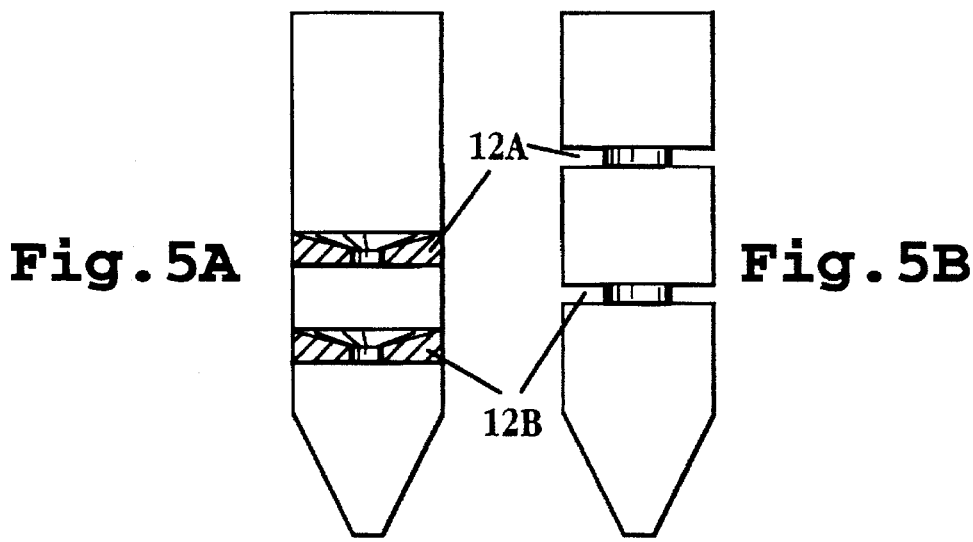
Figure 6:
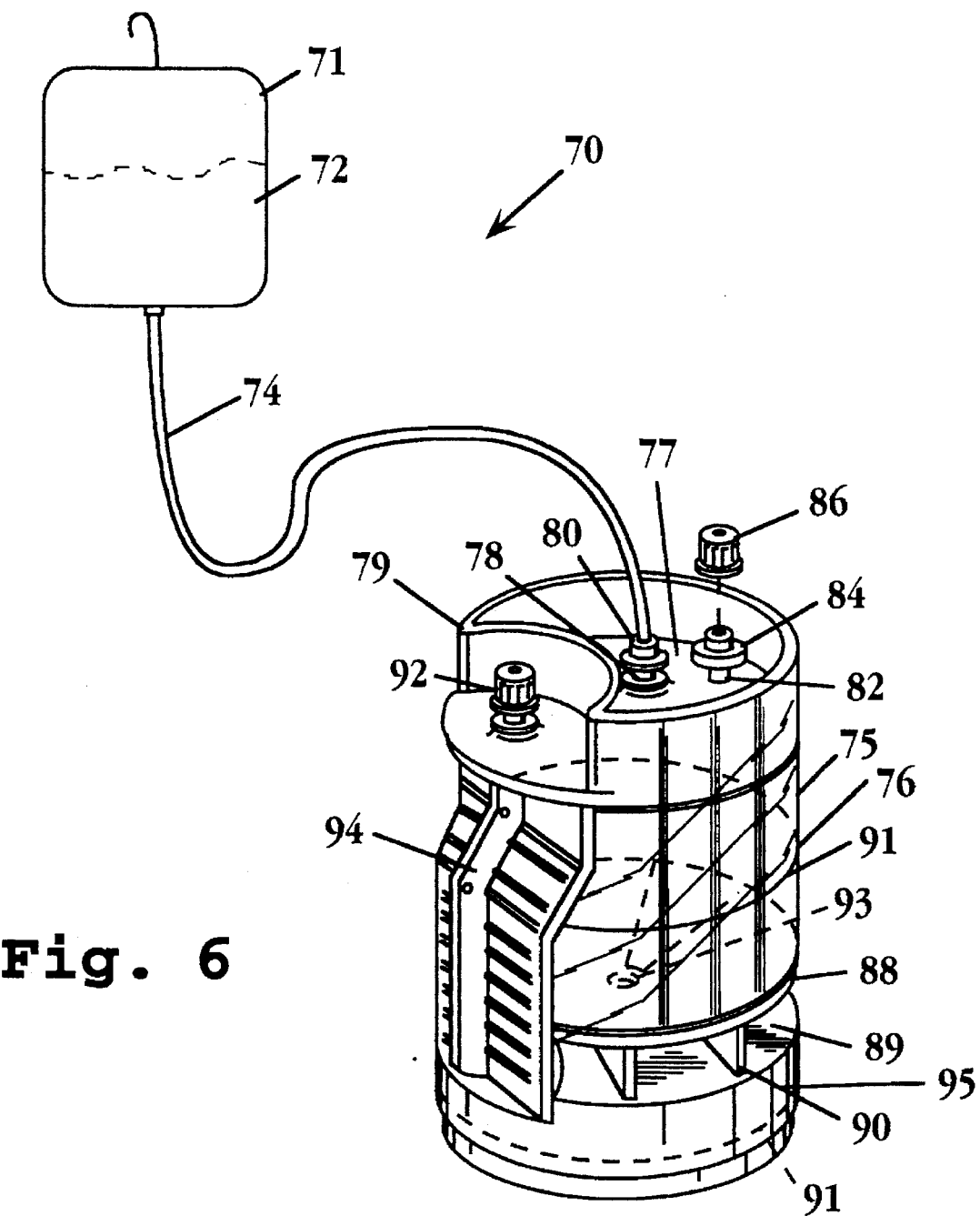
Figure 7:
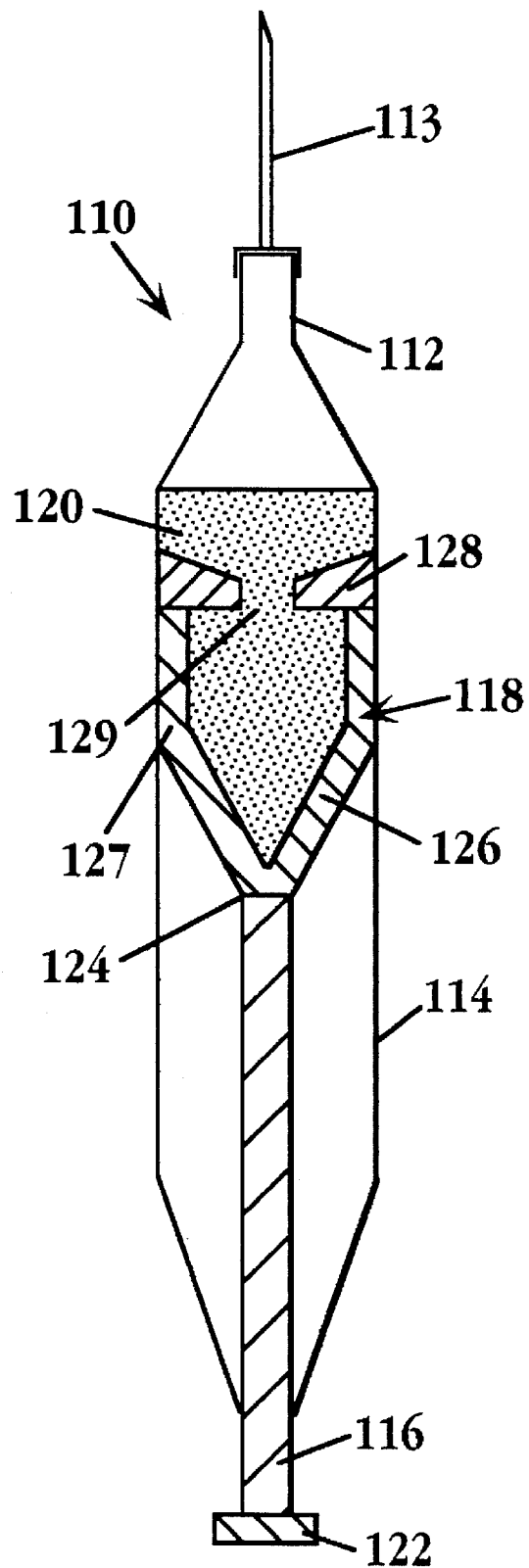
Figure 9:
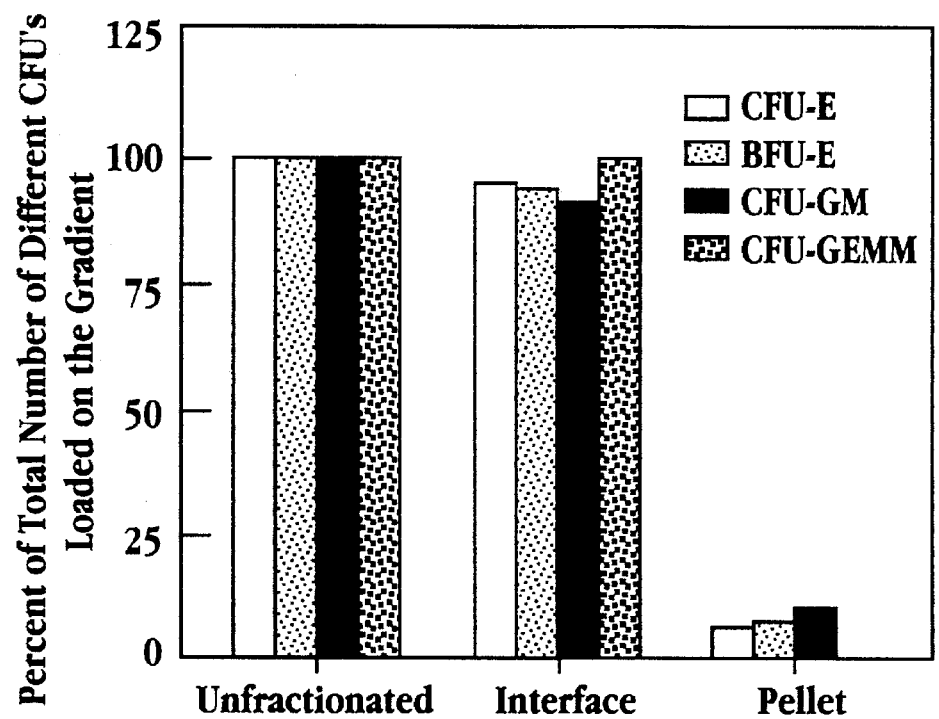
Figure 10:
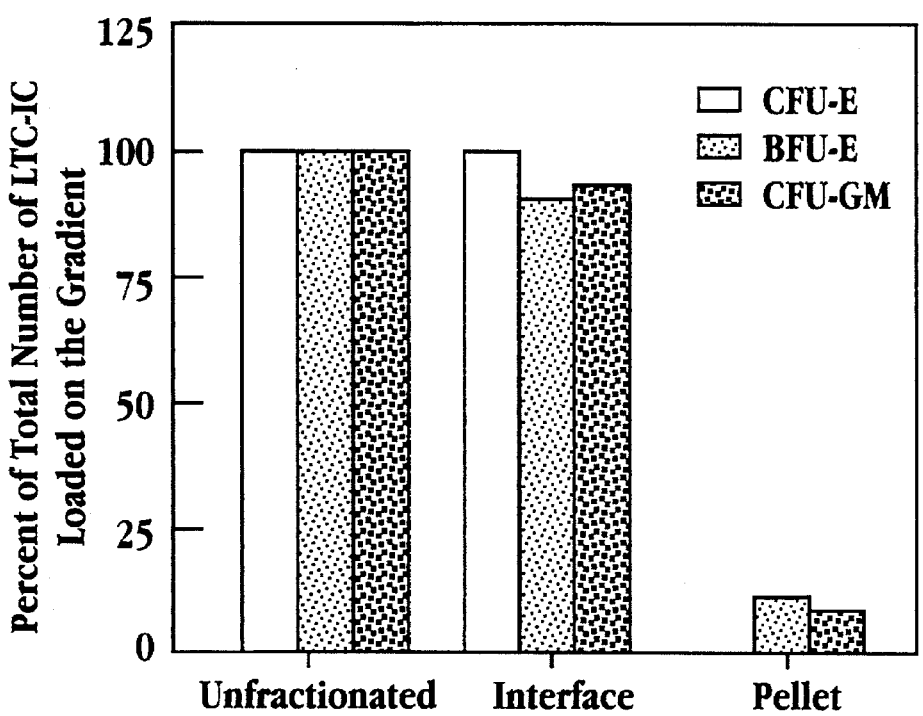
Figure 11A:
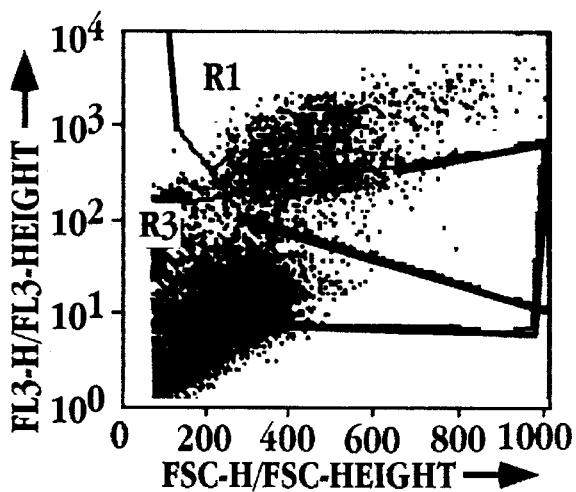
Figure 11B:
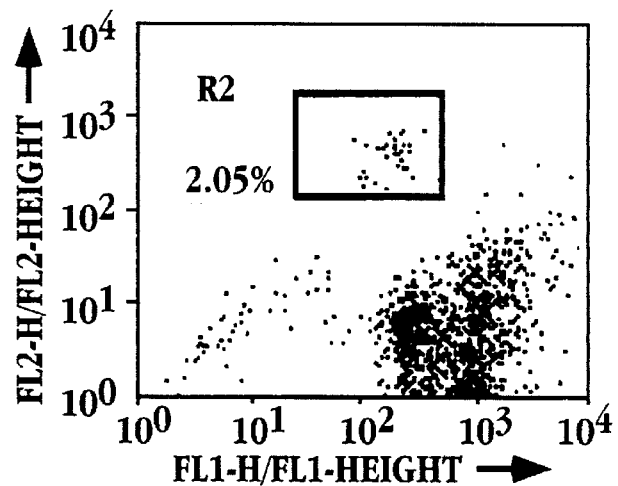
Figure 11C:
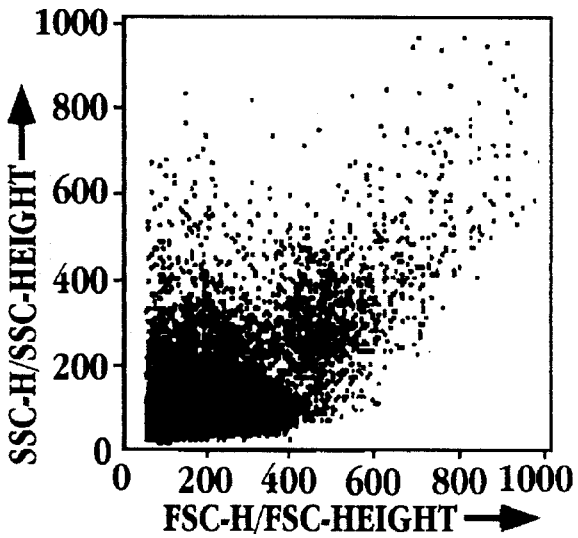
Figure 11D:
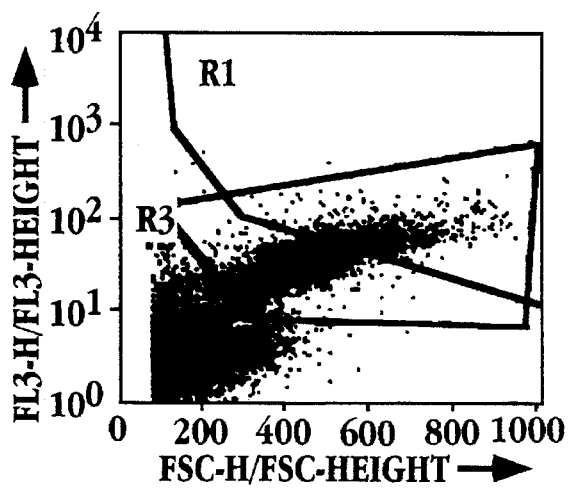
Figure 11E:
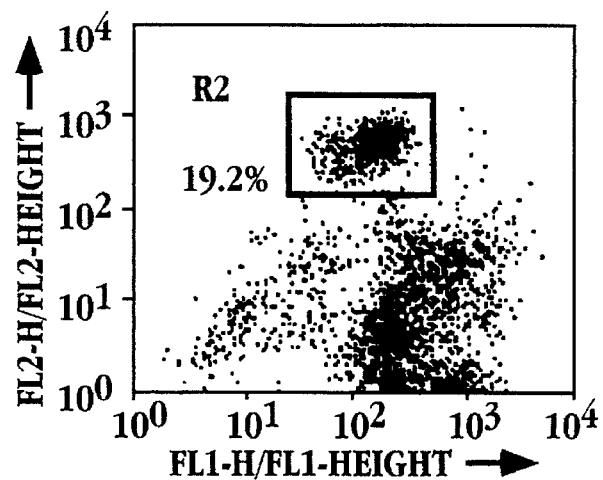
Figure 11F:
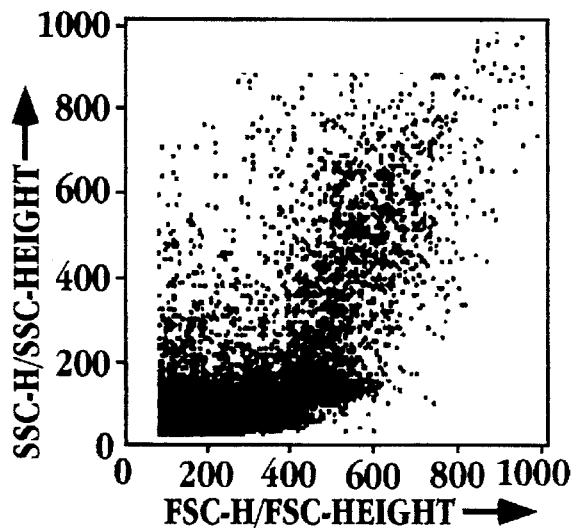
Figure 12:
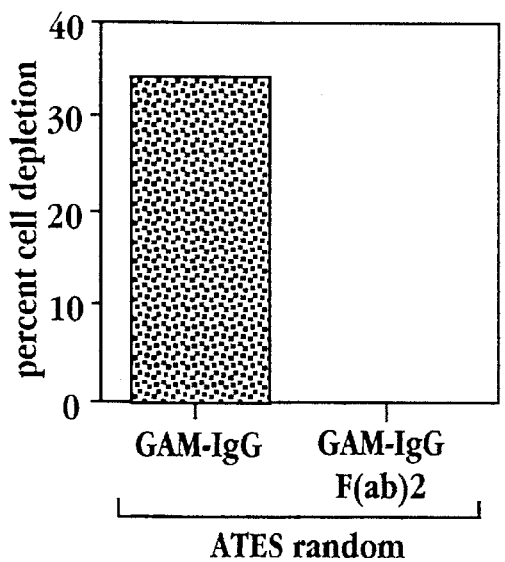
Figure 13:
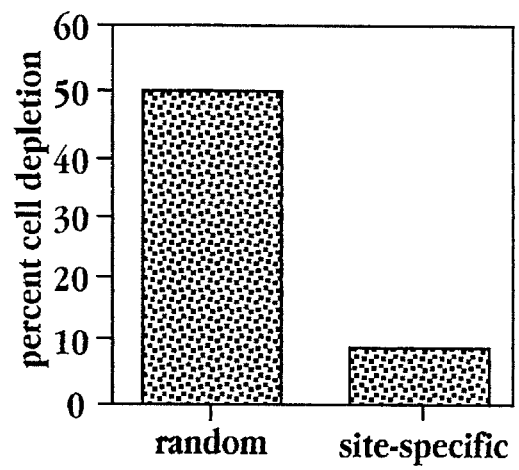
Figure 14:
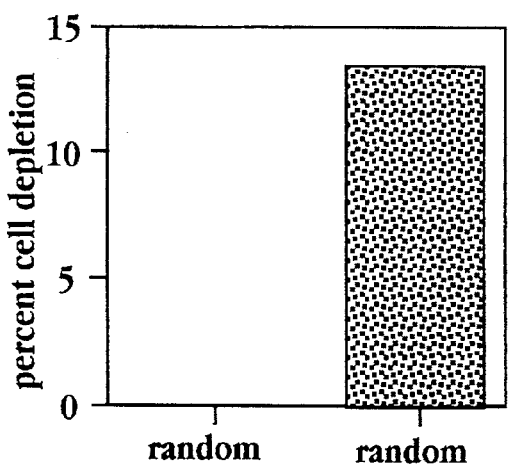
Figure 15:
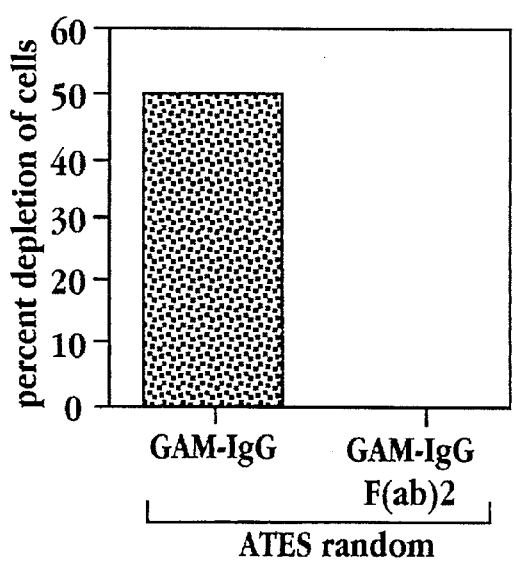
Figure 16:
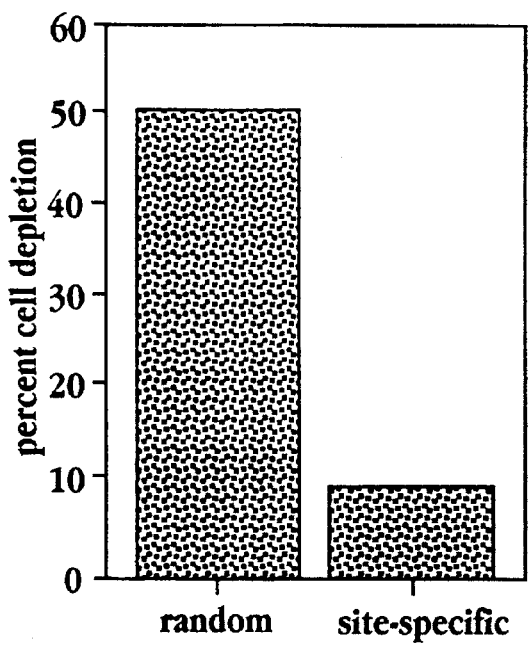
Figure 17:
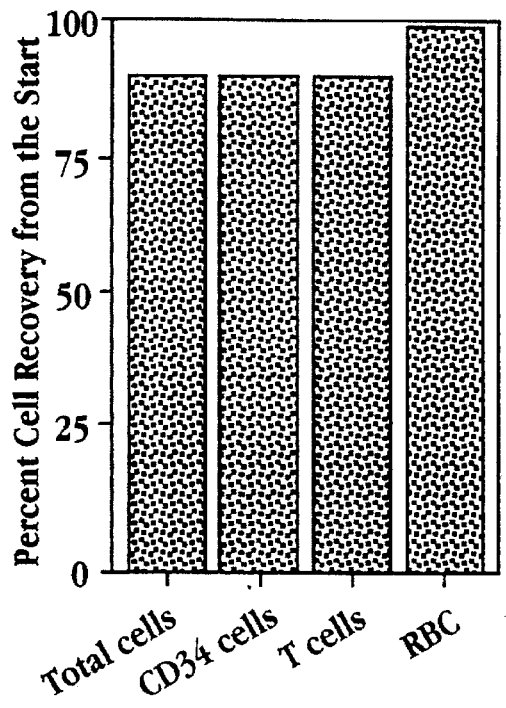
Figure 18:
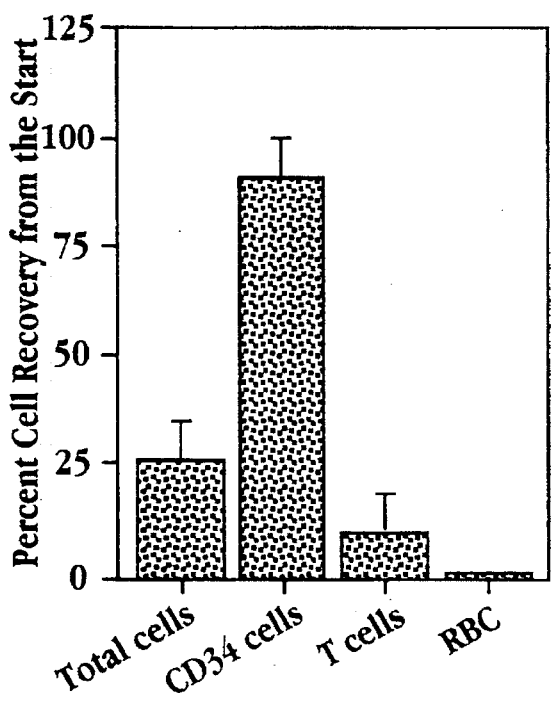
Figure 19:
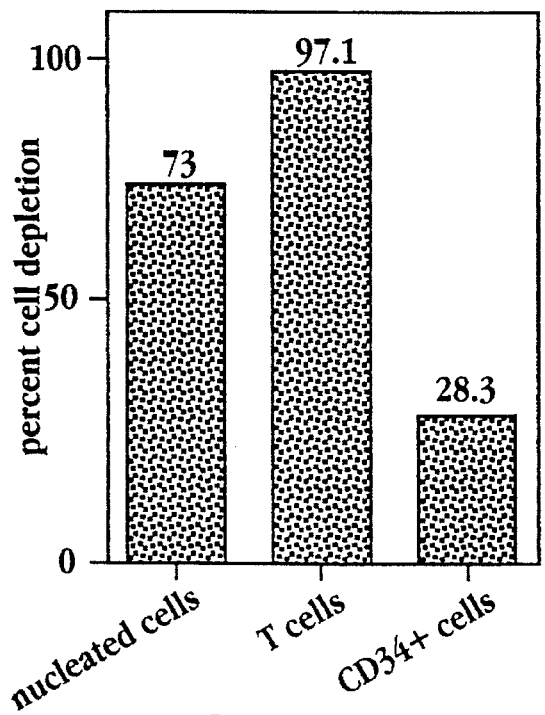
Figure 20:
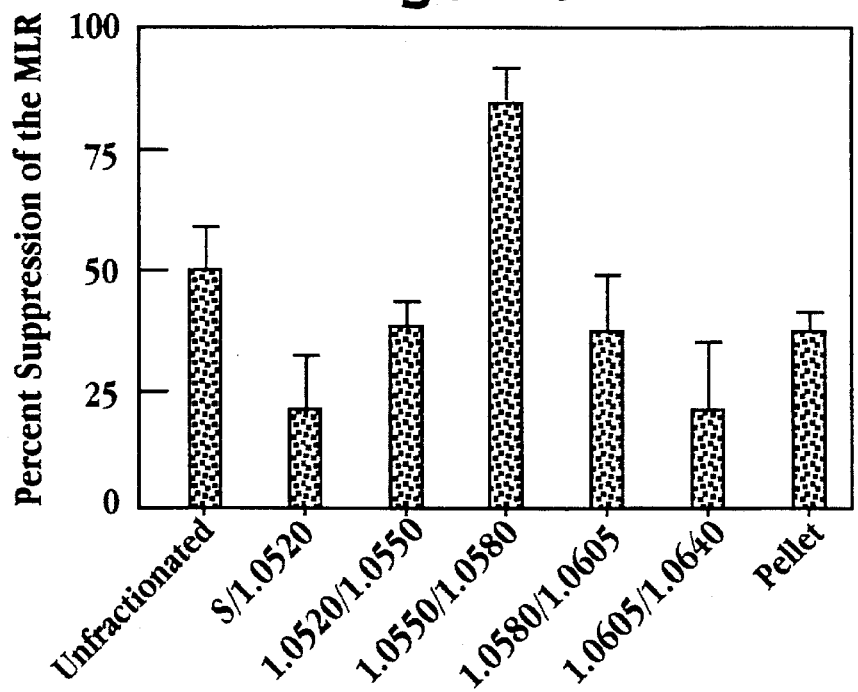
Figure 21:
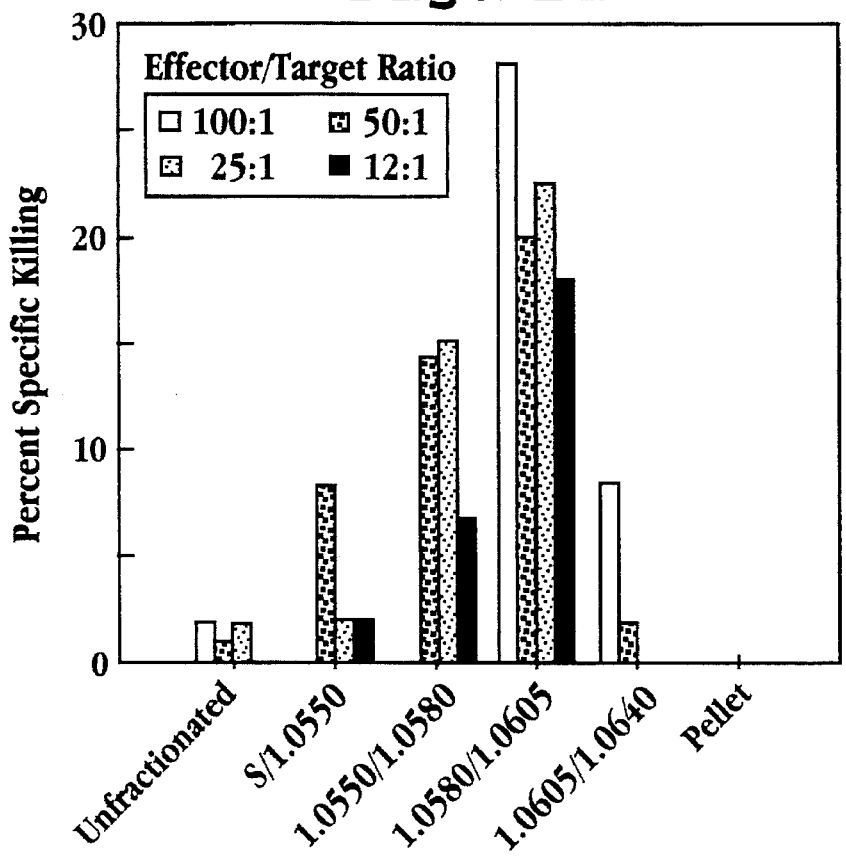
Figure 22C:
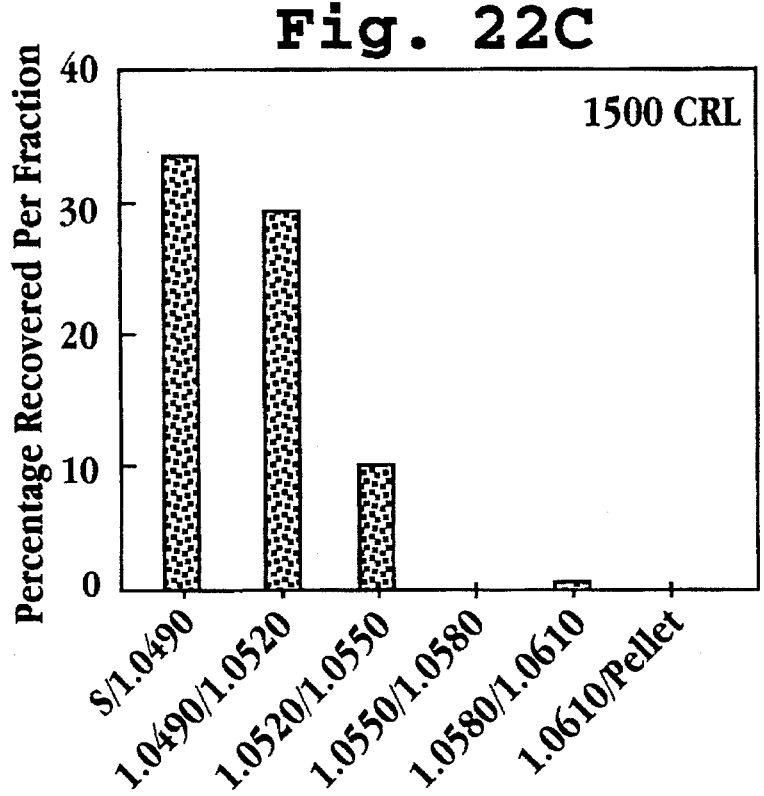
Figure 22D:
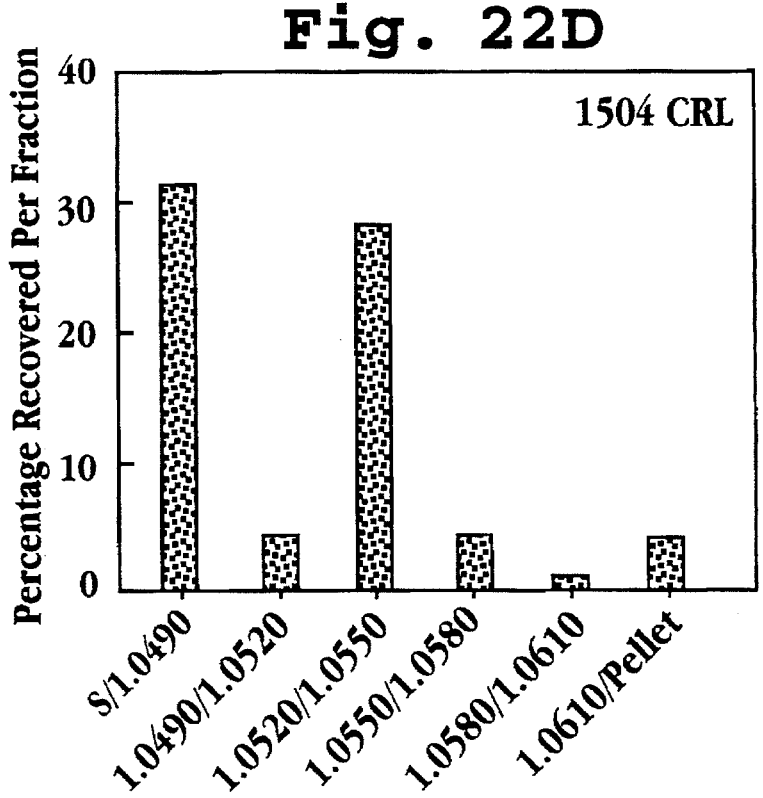
Figure 23A:
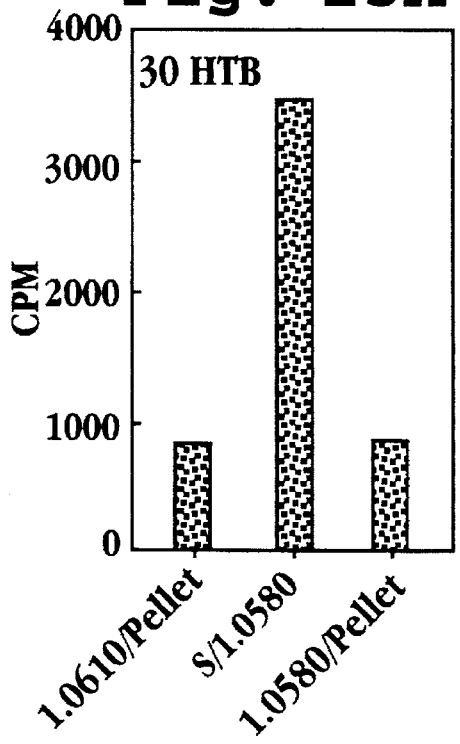
Figure 23B:
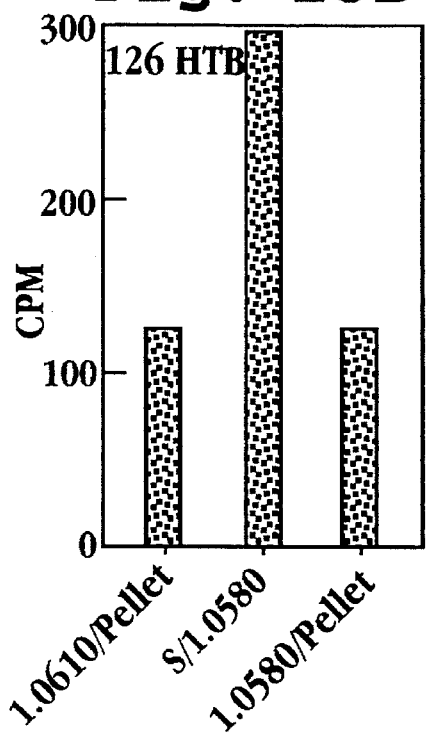
Figure 23C:
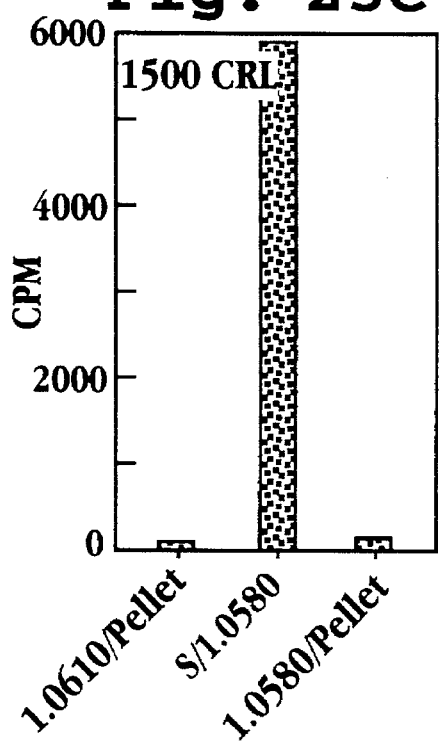
Figure 23D:
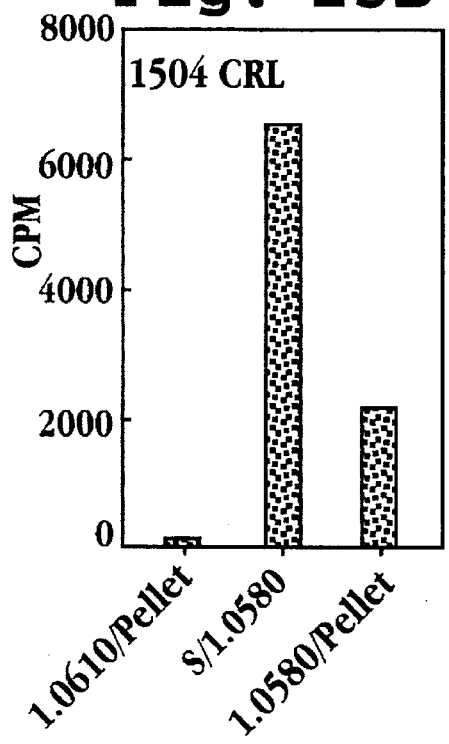

FIGS. 4A–F show cross-sectional views of alternative embodiments of the lower portion of the tube and constriction member of the invention;

FIGS. 5A and 5B show cross-sectional views of further alternative embodiments of the invention having multiple constriction members;

FIG. 6 shows an alternative embodiment of the centrifuge tube apparatus in a closed system suitable for processing of specimens under aseptic conditions;

FIG. 7 shows a centrifugable syringe embodiment of the centrifuge apparatus of the invention;

FIGS. 8(A–D) show a schematic drawings comparing conventional (8 A,B) with density adjusted cell sorting procedure (8 C,D);

FIG. 9 shows distribution of different types of CFU's in interface and pellet fractions;

FIG. 10 shows distribution of long-term culture initiating capability (LTC-IC) in interface and pellet fractions;

FIGS. 11A–11F show flow cytometric analysis of $CD34^+$ cell enrichment after density gradient centrifugation plus density adjusted cell sorting (DACS);

FIG. 12 shows a comparison of non-specific depletion of PBMC associated with DACS beads coated with two types of GAM-IgG preparations;

FIG. 13 shows non-specific depletion of PBMC by DACS beads coated with intact GAM-IgG in a random and a site-specific orientation;

FIG. 14 shows a comparison of non-specific depletion of PBMC associated with DACS beads coated of GAM-IgG in a random orientation in the absence and presence of PEG;

FIG. 15 shows non-specific loss of $CD34^+$ cells with DACS coated with intact GAM-IgG or F(ab)2 GAM-IgG;

FIG. 16 shows non-specific loss of $CD34^+$ cells with DACS beads coated with intact GAM-IgG in either a random or a site-specific orientation;

FIG. 17 shows percent recovery of total cells, $CD34^+$ cells, CTL's and red blood cells (RBC) from the combined interface+pellet after centrifugation of bone marrow cells on an OCS gradient;

FIG. 18 shows the percent recovery of total cells, $CD34^+$ cells, CTL's and red blood cells (RBC) from the interface of the gradient following centrifugation;

FIG. 19 shows depletion of nucleated cells, T lymphocytes and $CD34^+$ cells after DACS using anti-CD3, anti-CD4 and anti-CD8 mouse monoclonal antibodies;

FIG. 20 shows distribution of natural suppressor cell activity in different density fractions;

FIG. 21 shows distribution of natural killer activity in different density fractions;

FIGS. 22A–22D illustrate the enrichment of 4 types of breast tumor cells using the cell separation method of the present invention;

FIGS. 23A–23D illustrate enrichment of 4 types of breast tumor cells spiked in a cell mixture at a specific density of 1.0580 gr/ml.

Figure 24:
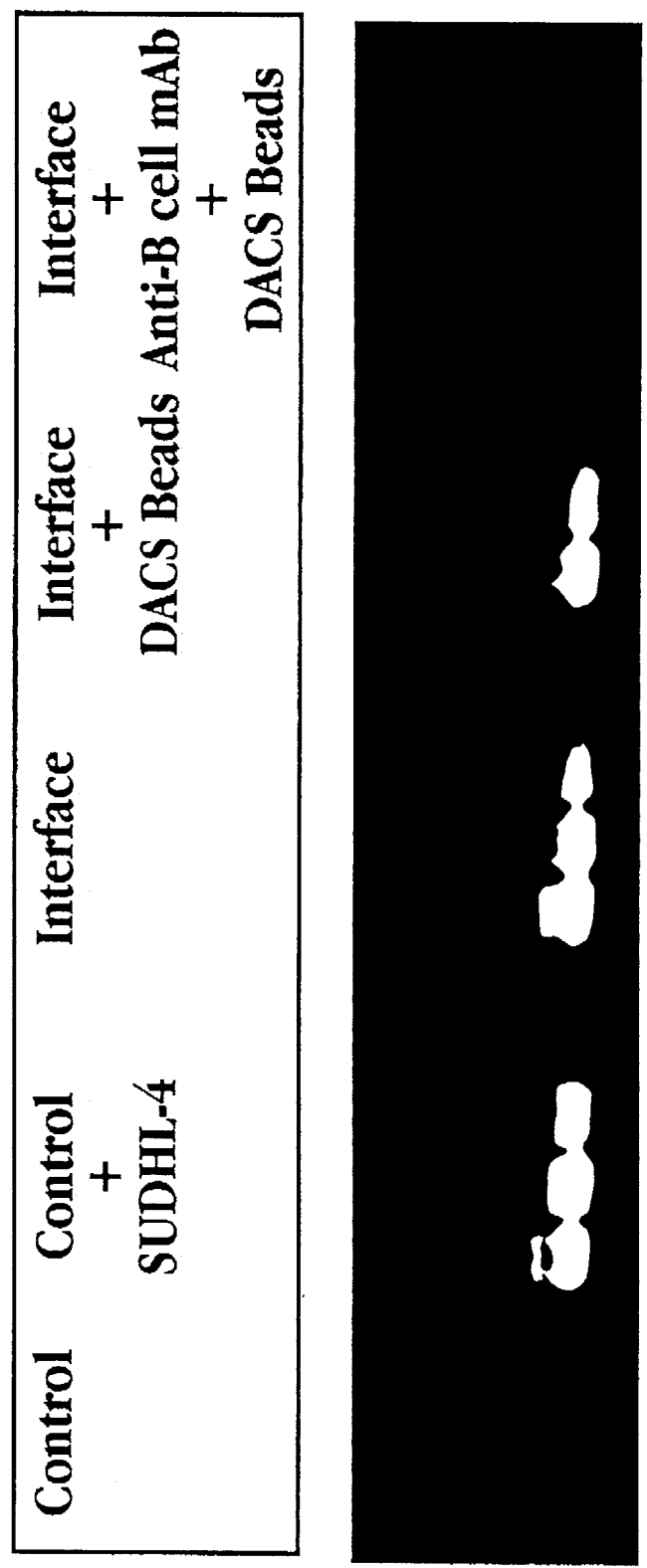
Figure 25:
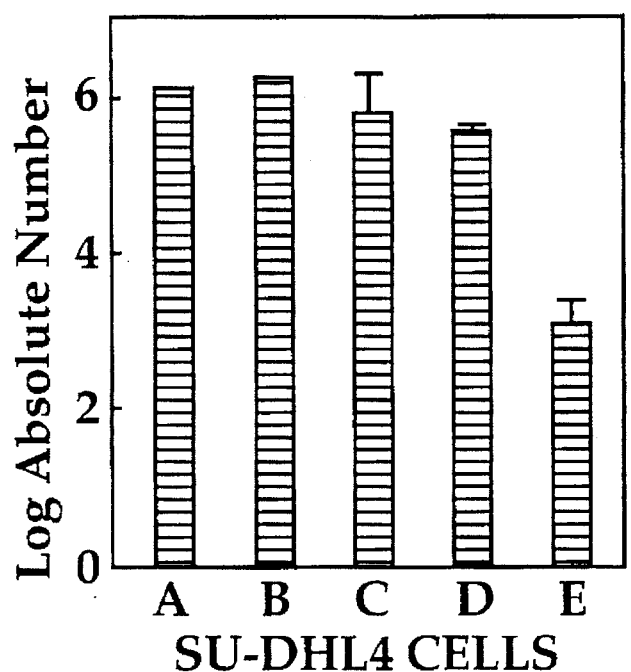
Figure 26:
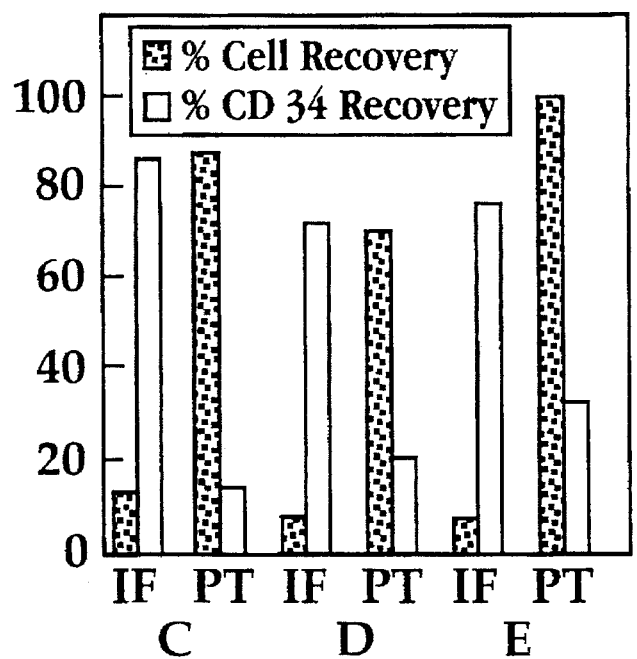
Figure 27A:
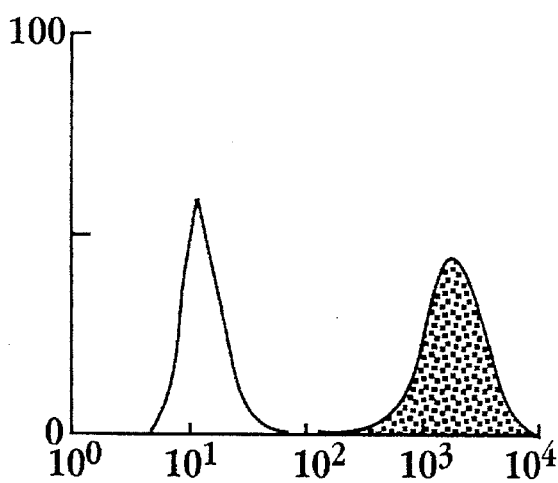
Figure 27B:
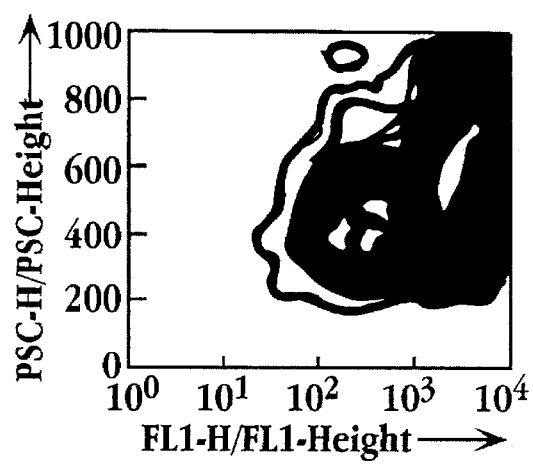
Figure 27C:
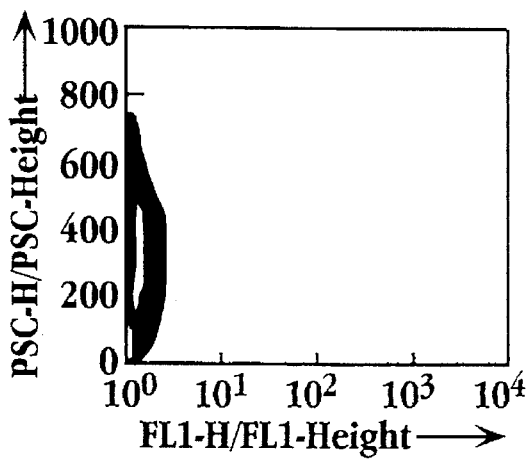
Figure 27D:
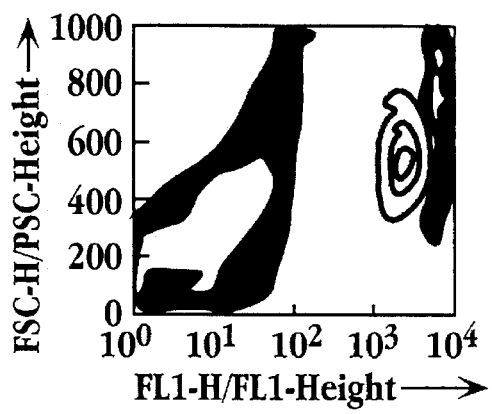
Figure 27E:
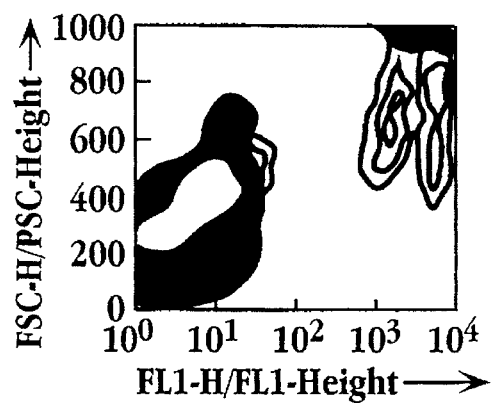
Figure 27F:
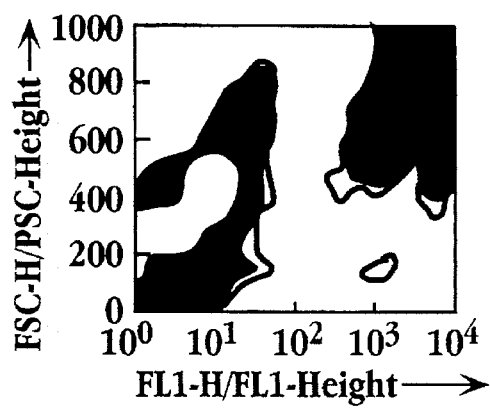
Figure 27G:
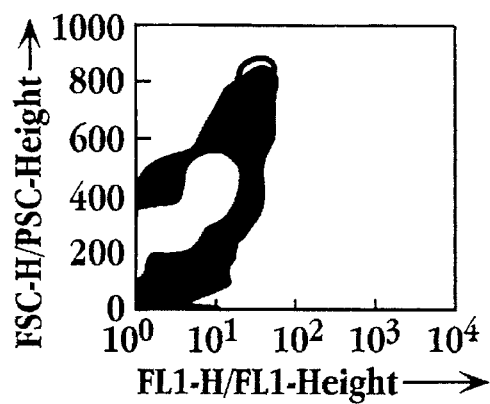

FIG. 24 shows a picture of a gel on which DNA samples extracted from a peripheral blood buffy coat containing tumor cells were analyzed by PCR, using 14;18 specific primers and following a single round of tumor purging by DACS;

FIG. 25 shows results of experiments in which peripheral blood buffy coat samples were depleted of human B lymphoma cells by DACS;

FIG. 26 shows recovery of $CD34^+$ cells in the depleted peripheral blood buffy coat samples of FIG. 25; and FIGS. 27 (A–G) show depletion of human breast cancer cells by DACS.

5. DETAILED DESCRIPTION OF THE INVENTION

Definitions

In the context of the present invention, the term "colloidal silica" refers to an aqueous suspension of colloidal particles formed by polymerization of monosilicic acid from $SiO_2$ dissolved in water.

"Organosilanized colloidal silica (OCS) particles" refers to a colloidal silica composition to which is covalently linked an organosilane coating. U.S. Pat. No. 4,927,749 is incorporated herein by reference in its entirety for its description of how to prepare such a composition.

"Rare blood cells" refers to cells that are derived from hematopoietic progenitor cells, including such cells, and which constitute less than or equal to about 1% of the total white blood cell (WBC) count in the blood of a healthy individual. Examples of rare blood cells include $CD34^+$ hematopoietic progenitor cells, which constitute about 1% of WBC's, natural killer cells, dendritic cells, cytotoxic T lymphocytes, natural suppressor cells and the like. In the context of the present invention, the term also encompasses tumor cells and nucleated fetal cells present in the blood at such abundance levels.

"Cell toxicity", "toxic to cells", and similar phrases herein refer to any diminution in cell viability or biological function that is measurable in a cell population. With reference to the hematopoietic progenitor cells described herein, the term most commonly refers to diminution in clonogenic potential, as evidenced by reduced yield of cells capable of forming hematopoietic colonies (CFU). "Dendritic cells", or "DC" are matured dendritic precursor cells, which are negative for expression of CD3, CD4, CD8, CD14, CD16 and CD20, positive for expression of HLA-DR (i.e., class II MHC). Dendritic cells typically have a dendritic cell morphology—that is, they are large veiled cells which extend dendrites when cultured in vitro.

A "tumor cell antigen" is a molecule, generally a protein, that is exposed on the surface of a particular tumor cell. Examples of tumor cell antigens include CD9, CD10, CD19 and CD20 for B cell lymphoma; tumor cell antigens that are specific for certain breast tumors include Her2/Neu and estrogen receptors.

In the context of the present invention, the term "isotonic" means having an osmolality that is within the range tolerated by the cell, usually about 280–340 mOsm/kg $H_2O$, and preferably, for human cells, about 280 mOsm/kg $H_2O$, depending on the cell type and source.

Introduction

The present invention relates to methods of rapid and high yield isolation or enrichment of a desired cell population from body fluids, dispersed tissue specimens, cultured cells and their components. The method is based on density gradient centrifugation of selected cell mixtures using highly defined density gradient media. More specifically, the present invention includes a specially designed cell-trap centrifugation tube apparatus containing density gradient solution that maximizes yield and improves efficiency of the collection process.

The general invention also includes, and is exemplified by, cell separation methods for isolation of specific cell types: nucleated fetal cells, hematopoietic progenitor $CD34^+$ cells, breast tumor cells, natural killer cells, and dendritic cells. Each of these cell types illustrates an important diagnostic and/or therapeutic use of cells isolated by the methods of the invention. For example, as described herein, nucleated fetal cells can be isolated from circulating maternal blood for the purpose of performing a variety of genetic analyses, e.g. karyotyping. Breast tumor cells can be isolated from circulating blood for the purpose of performing diagnostic tests, e.g. cytological examination, or for the purpose of purging tumor cells from a blood sample intended for subsequent re-infusion, e.g. transfusions or transplants. Hematopoietic progenitor cells can be isolated from blood or bone marrow for use as donor cells in bone marrow transplantation. Dendritic cells, natural killer cells, cytotoxic T lymphocytes and natural suppressor cells can all be isolated from blood or bone marrow for use as therapeutic agents in adoptive cell therapy.

5.1 Density Gradient Cell Separation Method

This section describes cell separation methods using specific density gradients in accordance with the invention. More specifically, the sections that follow contain descriptions of particular aspects of the invention: (1) the use of a cell-trap centrifugation device in conjunction with a defined cell separation medium to isolate specific cell types (Section 5.1.A); (2) the use of a single-step density medium with a defined density to isolate particular cell types (Section 5.1.B); and (3) the use of carrier particles coupled to specific binding agents to enhance the efficiency of the cell separation processes of the invention (Section 5.2). In addition, isolation of exemplified cell types using the methods of the invention are described in Section 5.3.

5.1.A. Cell-trap Centrifuge Apparatus and Kit

In a preferred embodiment, the present invention includes a centrifuge apparatus and its use for density separation of selected cell types. The term "cell-trap tube" refers to a centrifugation tube which forms part of the apparatus, and which includes a constriction that forms a "trap" or fluid receiving region in the bottom portion of the tube. As will be illustrated by the description and drawings of the specific embodiments that follow, an important feature of the constriction member is that it is positioned within the tube in a manner such that fluid is retained in the bottom portion of the tube below the constriction member, when the tube is inverted. The constriction member thus defines a central opening and two compartments separated from each other by an air lock created by surface tension at the central opening during inversion of the apparatus. The apparatus of the invention also includes a cell separation medium for density separation of cells.

Figure 1A:
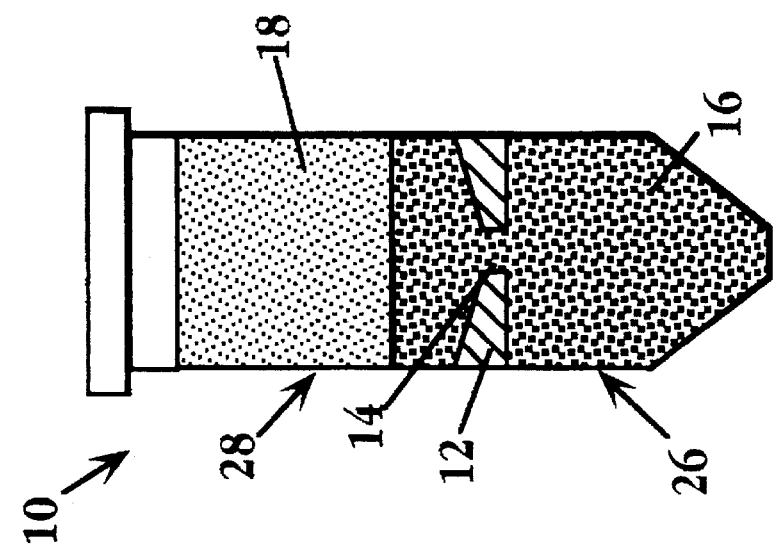
Figure 1B:
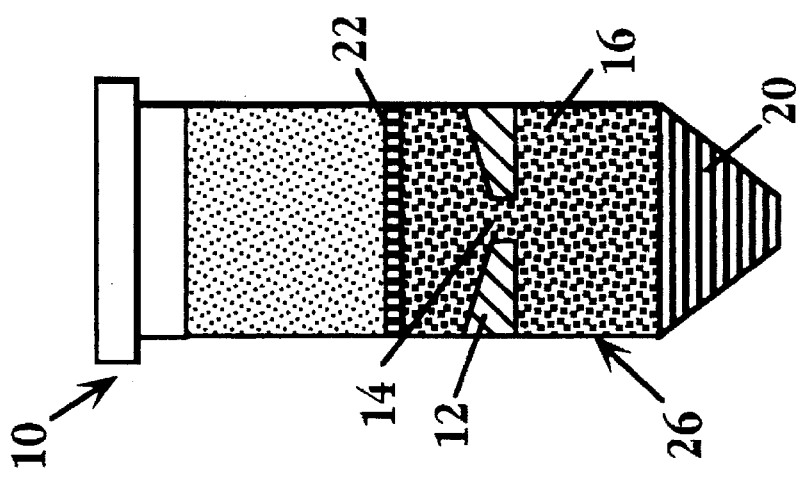
Figure 1C:
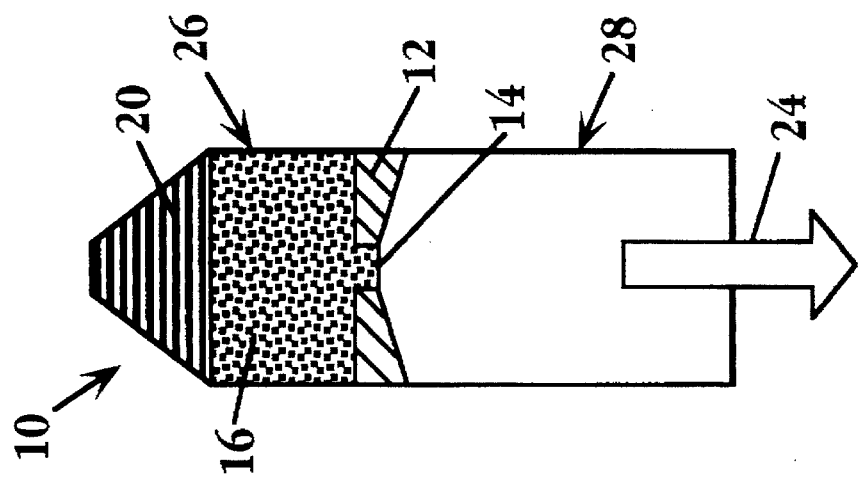

One embodiment of the centrifugation apparatus of the invention is shown in cross-section in FIGS. 1A and B. As shown, the centrifuge device is tube 10. Constriction member 12 in tube 10 defines central opening 14. Constriction member 12 preferably defines one or more downwardly sloped upper surfaces having lower edge regions defining constricted opening 14.

The bottom surface of the constriction member may also may be similarly, slightly angled (although not shown as such in the figures). In an exemplary embodiment, with a tube having an inner diameter of about 2.8 cm, the diameter of opening 14 formed by constriction member 12 is preferably about 0.5 cm. The size of opening 14 is generally not so small as to prevent heavier components of a sample, layered on top of the density gradient solution, from passing through the opening prior to actual centrifugation. Such a movement of components may occur due to normal gravitational forces. In general, the diameter of opening 14 is dictated by the ability to form an increased surface tension across the opening and thereby form an airlock that separates the upper and lower compartments. A restriction that is little more than a rim around the interior of the barrel may be sufficient to provide such a surface tension. Hence, the cross-sectional area of the aperture formed by the constriction member may be as little as about 5% or as great as about 95% of the horizontal cross-sectional surface area of the tube.

While the constriction member illustrated in FIGS. 1A–C and 2A–B are annular (e.g., ring-like), it is appreciated that the constriction member may form a number of opening shapes, or may form a plurality of openings. The shape of opening 14 is not limited to a circular shape, though in general, a funnel-shaped constriction member forming a roughly circular shape will be preferred. The opening may also be oval, rectangular, star-shaped, or any other shape that would create a restricted passage within the tube, provided that the geometry provides for creation of sufficient surface tension to impede discharge of fluid in the bottom of the tube upon inversion, as described above. In addition, the constriction member may comprise a mesh or a sieve spanning the horizontal cross-section of the tube. In this case, the annular member is also said to comprise a plurality of openings.

In addition, while the opening will preferably be centered horizontally within the tube, the opening may also be off-center and achieve substantially the same results. With respect to vertical construction and positioning in the tube, the constriction member may be formed integrally with the tube or may be constructed for a forced fit. For example, an annular constriction member may be formed from an elastomeric silicone material to be inserted into the tube by a forced fit at any position along the length of the tube.

Referring again to FIG. 1A, tube 10 is filled with cell separation density gradient solution 16 to a level above constriction member 12, or, minimally, at least above opening 14. Preferably, with reference to a standard 50 ml centrifugation tube, density gradient solution 16 is filled to a level at least about 1 mm above the constriction member, to facilitate formation of an interface above the constriction member. The fluid sample 18 to be separated is layered on the top of density gradient solution 16, and the tube. Preferably, the sample is carefully layered so that at least about 1 mm of density gradient solution remains between the sample and the top of the constriction member after layering, for the reason stated above. The tube and its contents are then subjected to centrifugation at a centrifugal force and duration to pellet cells having densities greater than the density of the gradient solution.

Referring to FIG. B, following centrifugation, components having densities greater than that of the gradient solution are found in a pellet 20 at the bottom of tube 10. Cellular components having densities less than that of the density gradient solution 16 remain floating at the top of the solution, in an interface 22 between the gradient solution and the remaining portion of the fluid sample solution. The interface portion is then removed. Such removal can be by decantation of the tube, as indicated by arrow 24 in FIG. 1C. The provision of the density gradient solution to a level above the opening as described above helps to prevent the formation of an interface portion below constriction member 12.

Without ascribing to any particular underlying theory of the operability of the tube, it is noted that constriction member 12 facilitates pouring off the upper portion by providing a support or nucleus for formation of an intermediate surface tension across the surface of opening 14, when the tube is tilted for pouring. This surface tension creates an airlock that impedes mixing of upper and lower portions of the tube when the contents of the upper portion are poured out of the tube. Constriction member 12 may be provided as an insert placed into a straight-walled tube. Alternatively, constriction member 12 may be formed as constriction of the tube wall during a molding process in the making of the tube itself. When the constriction member is provided by an insert, the insert may be movable to enable the operator to change the relative volumes of the lower portion 26 and upper portion 28 of tube 10 according to experimental conditions. The position of the constriction member in a molded tube can also be varied, during the manufacturing process, to provide tubes of differing relative upper and lower portion volumes. For example, in the isolation of cells from peripheral blood, a 20 ml sample of blood requires lower portion 26 to be about 15 ml in order to accommodate the relatively large amount of red blood cells centrifuged out. By comparison, a 20 ml sample of apheresis or buffy-coat blood would require only about 10 ml in the lower portion.

In many applications, it will be desirable to collect only the supernatant fraction containing the interface portion. In such cases, the pellet is discarded with the tube. In other cases, the pellet can be removed by mechanical manipulation/disruption. For example, the tube can be inverted and subjected to vortex mixing. Such mixing will disrupt the pellet into the adjacent liquid phase and will induce movement of this liquid phase and disrupted cells from the lower or collection portion of the tube into the upper portion of the tube.

An advantage of the present invention is that the low density material above the constriction member is separated from the material beneath the member by the simple act of pouring or decanting the contents of the upper portion of the tube. This contrasts with many conventional methods of unloading gradient separations using standard straight-wall centrifuge tubes, where materials are separated by carefully pipetting out of the tube or, alternatively, by puncturing the bottom of the tube and allowing the contents of the tube to slowly drip out into collection vessels. Thus, the present invention provides a convenient, simple means for unloading differentially separated materials.

Generally, in separating cells by density centrifugation using the tube of the invention, a solution, such as solution 18 in FIG. 1A containing cell mixture loaded onto the density gradient medium or material in the tube, will have a specific density that is less than the specific density of the density gradient or cell separation medium in the tube. During centrifugation, cells having a specific density that is less than or equal to the density of the cell separation medium will settle in the interface formed between the loading solution and the density gradient material.

Another advantage of the tube of the present invention is that, unlike conventional straight-wall tubes, if the tube is dropped or accidentally inverted, the contents of the separated upper and lower portions will not readily mix, due to the presence of the constriction member. Moreover, once separation has taken place, the solution present above the constriction member can be mixed in the tube, without disturbing (or fear of contamination by) the contents of the tube below the constriction member.

Figure 2A:
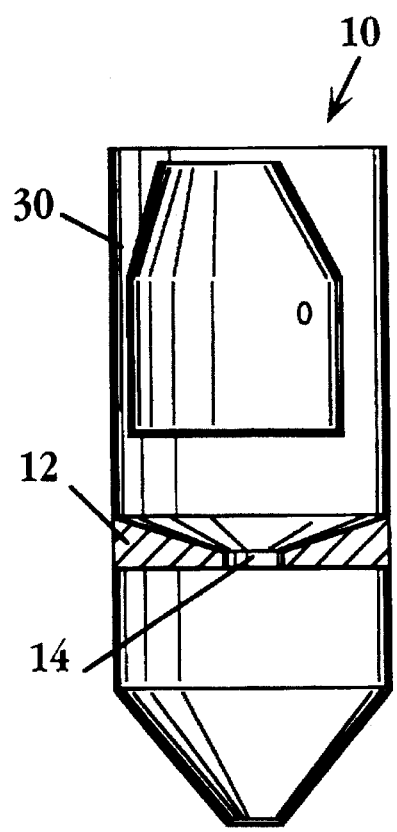
FIGS. 2A and 2B show schematic cross-sectional (2A) and perspective (2B) views of an embodiment of the centrifuge tube apparatus that includes a shield.
Figure 2B:
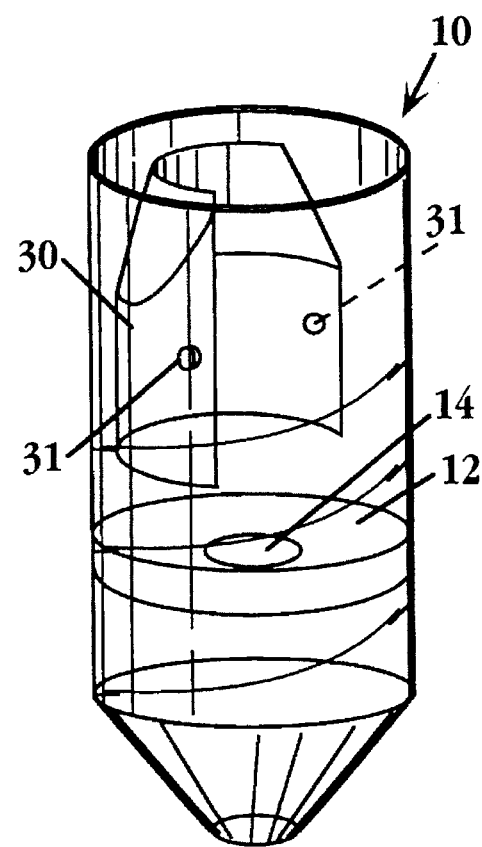

In an alternative preferred embodiment, tube 10 may be provided with insert or shield 30, as shown in FIGS. 2A and 2B. Shield 30 is provided above constriction member 12 to facilitate layering of the sample onto the gradient solution, and, more specifically, to facilitated automated loading of a sample. Shield 30 may take the form of a roughly concentric insert placed in the upper portion of the tube and extending at least partially around the tube. In use, the operator pipettes material between shield 30 and the tube wall. The shield directs the material along the side of the tube to the top of the density gradient solution, while minimizing disturbance of the solution. As shown in FIG. 2B, tube 10 is a clear plastic or glass, with constriction member 12 formed as a separate silicone insert. Shield 30 can be held in the upper portion of the tube, for example, by interference fit with spacers 31 biasing against the tube wall. Alternatively, shield 30 could be formed as a part of the tube.

Figure 3:
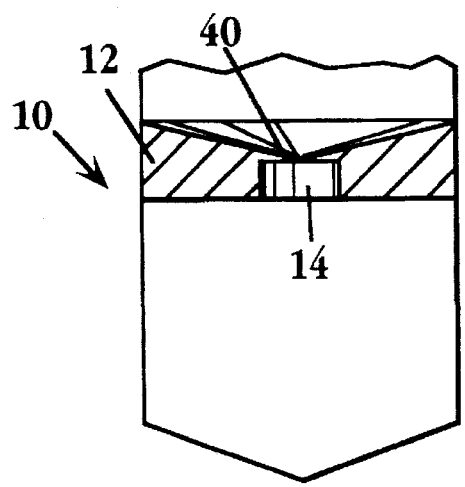
FIG. 3 shows a cross-sectional view of an alternative embodiment of the constriction member of the centrifuge apparatus with a valve.

The separation of materials may be further enhanced by the addition of valve 40 to the constriction member, as shown in FIG. 3. The valve 40 is located across opening 14. Valve 40 may be a one-way valve, or a valve that only opens upon application of a threshold centrifugal force. The valve can be formed by providing flaps of a softer material over the opening. In a preferred embodiment, the force required to open valve 40 would be about 850 times the normal force of gravity. Valve 40 thus allows heavy cells to pass through during initial centrifugation, and then keeps those cells in place, allowing for further processing of the lighter cells of interest located above the valve (such as washing or mixing of the cells). In this way complete and final manipulation of the cells can be performed in a single sterile container.

Figures 4A, 4B, 4C:
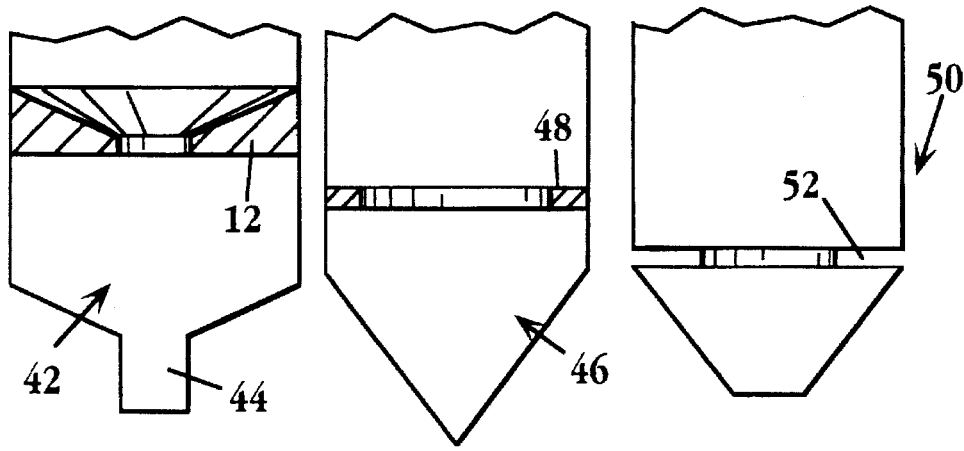
Figures 4D, 4E, 4F:
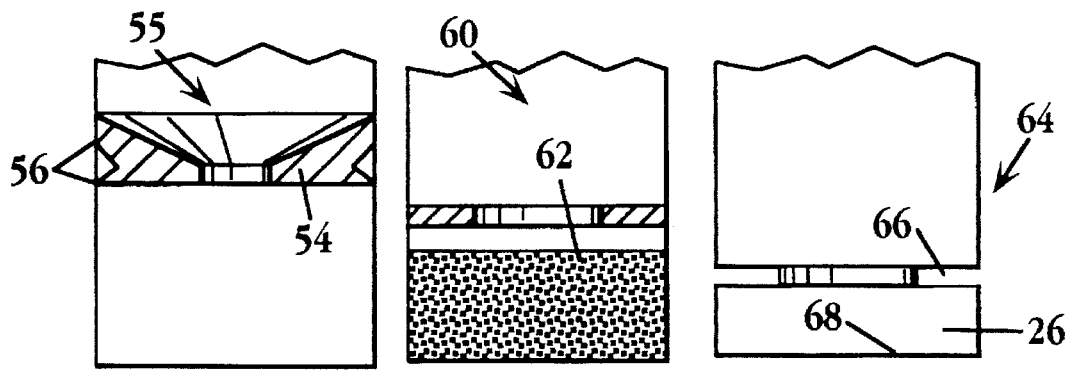

FIGS. 4A–F are illustrations of alternative shapes and designs for the tube and constriction member according to the invention. FIG. 4A shows alternative tube 42 having a separate bottom compartment 44 for receiving the pellet to provide optimal collection of cells. Constriction member 12 is as previously described; it is funnel shaped on its upper surface and formed from a separate insert of plastic or, preferably, silicone. FIG. 4B shows a tube 46 with a pointed bottom wall. Tube 46 with the pointed bottom wall also enhances cell collection by allowing the heavier cells to form a better pellet, which may be desired if the cells are to be collected. Constriction member 48 is again an insert, but with a flat upper surface and wider opening. FIG. 4C illustrates alternative tube 50 with an integrally molded constriction member 52. FIG. 4D shows an alternative constriction member 54 that facilitate movement within tube 55 to adjust the relative volumes of the upper and lower portions. For this reason constriction member 54 has annular extending contact points 56. The constriction member will only contact the tube at these points, which create a fluid tight seal, but allow for easier adjustability. Tube 55 also has a flat bottom. FIG. 4E illustrates a further alternative embodiment of the present invention, wherein tube 60 includes cell trapping material 62, such as a sponge or gel. Material 62 may contain compounds that specifically bind certain cell types or toxins that kill specific cell types. Material 62 also may be made of a magnetic material if desired. Tube 64, shown in FIG. 4F, illustrates a further example of an integrally formed constriction member 66 in a tube with a flat bottom wall 68. Construction member 66 is located such that lower portion 26 has a smaller relative volume.

FIGS. 5A and 5B illustrate further alternative embodiments of the tube according to the invention. In each, two constriction members are provided. Second constriction member 12A is located above first constriction member 12B to create more compartments to allow separation of cells of differing densities. In FIG. 5A, the constriction members are shown as separate inserts, whereas they are integrally formed with the tube in FIG. 5B. Additional constriction members could also be added if a sample of several different densities is to be separated.

FIG. 6 depicts a centrifuge apparatus of the invention incorporated into a closed system. Such a system is particularly useful for sterile processing of samples, such as, for example, blood samples or samples that are to be later infused into a patient. As illustrated, closed system 70 includes a reservoir 71, shown as a sterile bag, containing blood 72 previously collected by known techniques, connected by sterile connecting tubing 74 to centrifuge device 75, illustrated as a "bucket" style centrifuge tube 76 having a closed top 77. The closed top will have at least one, and preferably at least two entry ports, useful for introduction and removal of sample, and for venting, as described below. In the embodiment shown, solid ridge 79 protruding upward from closed top 77 is included to form a protective barrier for the entry ports, as a safety guide for accessing compartments, and as an attachment point for a protective, removable lid for the apparatus that serves to reduce potential contamination during shipping and storage.

With further reference to FIG. 6, tubing 74 is attached to tube 76 through entry port 78, adapted with fitting 80, which may be any type of locking tip adapted for sterile connection, for example, a LuerLock™ syringe connector. Alternatively, fitting 80 may be a sterile septum adapted for connection with sterile fluid bags and tubes, for example a SAFSITE™ small wire extension set with reflux valve and Spin-Lock™ adaptor available from Burron Medical Inc., Bethlehem, Pa. To facilitate fluid flow into centrifuge tube 76, the tube contains air vent entry port 82. As shown, air filter 84 is attached to entry port 82 to prevent contamination.

In accordance with the invention, tube 76 includes constriction member 88, formed as previously described, and funnel shaped on its upper surface. As illustrated, constriction member 88 is formed integrally with tube 76 forming an indentation 89 on the outer surface of the tube and is supported by supports 90 to prevent compression during centrifugation. The constriction member may also be formed as a forced fit annular insert, as described above. The tube also contains density material 91 disposed in the tube both above and below constriction member 88.

An added feature of tube device 75 is entry port 92. This entry port communicates via closed fluid channel 94 with the bottom portion 95 of tube 76. The entry port and channel are used to fill the lower portion of the tube 95, for example, with density gradient cell separation medium. In practice, cell separation medium can be introduced through fluid channel 94 to lower portion 95, first to a level just below or at the lower extent of opening 93. Sample is then added to the upper portion of the tube; then additional separation medium is added to the lower portion, through channel 94 as before, until the separation medium rises to a level above the level of opening 93, where it directly underlies the sample. Alternatively, the port and channel may be used to remove materials, including cell pellet materials, from the bottom of the tube following centrifugation. This feature of the tube is neither required by nor restricted to the closed system context in which it is illustrated.

Fluid flow from reservoir 70 into tube 76 can be initiated by applying suction on air vent entry port 82, or it may be initiated by other means known in the art, including gravity and pressure. The rate of flow is adjusted, either by altering the pressure head between the two containers or by regulating a valve positioned in the tube or at the entry port at a point between reservoir 70 and entry port 78. Flow rate is optimally regulated to fill or partially fill the upper portion of tube 76, above the level of the density gradient solution. When sufficient fluid sample has entered the tube, flow can be terminated by any of a number of means known in the art, such as regulation by a valve or roller clamp, or by lowering of pressure head. The tubing is then removed from the device, port 78 is sealed, and the device is subjected to centrifugation as described above.

In a related embodiment, the centrifuge device described above, and particularly the device in the closed bucket tube configuration, can be further adapted and used to culture isolated cells. Here, the centrifugation device will preferably be formed of a plastic suitable for cell growth, such as polystrene, polycarbonate, polytetrafluorothylene (PTFE; TEFLON), with such coatings or treatments known to promote cell growth. In this case, the cell separation medium will generally be a physiological culture medium, through which cells are centrifuged, generally in a second step of the purification. That is, in one preferred embodiment, cells enriched by density gradient centrifugation as described above are transferred to a cell-trap tube containing as cell separation medium a conventional culture medium such as Earle's complete medium, supplemented as appropriate to the cell growth requirements. The cells are then pelleted through this medium, and the entire centrifugation flask is transferred to an incubator for growth conditions.

In another preferred embodiment, the cell-trap tube may be used in the form of a centifugable syringe, such as centrifuge syringe 110 illustrated in FIG. 7. As illustrated, centrifuge syringe 100 includes a specimen container 114 with a central orifice surrounded by fitting 112 adapted for receiving a needle 113, a handle 116 and a plunger 118. Fitting 112 may be any type of locking tip adapted to hold a needle, for example, a Luer-Lock™ syringe tip. Alternatively, fitting 112 may be a sterile septum adapted for connection with sterile fluid bags and tubes, for example a SAFSITE™ small wire extension set with reflux valve and Spin-Lock™ adaptor available from Burron Medical Inc., Bethlehem, Pa.

Handle 116 further preferably comprises knob 122 and a removable connection 124 to plunger 118. As shown, plunger 118 is single piece, machined or molded from a plastic material. The plunger preferably has a funnel-shaped bottom wall 126 that is removably connected to the handle at connection 124. Side wall 127 preferably closely matches the container wall to permit sliding movement but still provide an essentially fluid-tight barrier therearound. A top wall is formed by constriction member 128, which defines central opening 129. Alternatively, the outer diameter of side wall 127 may be slightly undersized to facilitate sliding and an o-ring seal provided between side wall 127 and container 114. Removable connection 124 may take the form of, for example, a screw fitting or a snap-fit. Preferably, connection 124 also provides for reattachment of handle 116.

The plunger 118 is filled with a density gradient material 120 before the introduction of a specimen. Preferably, the density gradient material is filled to a level above the constriction member, or at least above the top of opening 129. For example, when using a standard 50 ml syringe, having an inner diameter of about 2.8 cm, the gradient material is preferably filled to a level about 1 mm or more above constriction member 128, so that the interface forms above constriction member 128.

5.1.B. Density Gradient Materials and Preparation

According to an important aspect of the invention, it has been discovered that significant enrichment of specific cells can be effected by centrifugation of a cell mixture on a single layer cell separation medium having a well defined specific density. The defined specific density is roughly the density of the desired cell type to be isolated. Importantly, the cell separation medium must be prepared to an accuracy of ±0.0005, and preferably ±0.0002, of the specific density of the desired specific cell type. Using such well defined medium, specific cell types can be isolated by centrifugation on a single density medium in a conventional centrifuge tube. However, as shown herein, use of a cell-trap tube in conjunction with such medium will generally facilitate improved handling as well as yield.

The apparatus and methods of cell separation of the present invention include use of a cell separation material, such as a density gradient material, having a specific gravity between 1.0000 gr/ml and 2.0000 gr/ml, preferably between 1.0300 gr/ml and 1.2000 gr/ml, that is accurate within ±0.0005 gr/ml, preferably ±0.0002 gr/ml of the specific gravity of the desired cell. A variety of commercially available gradient materials may be used to achieve cell isolation based on the defined density of the desired cell population, including, but not limited to, "PERCOLL", available from Pharmacia; "FICOLL HYPAQUE"; "NYCODENZ" (Nycomed); any sugar solution, e.g. sucrose; dextran; any protein solution, e.g. bovine serum albumin (BSA); iodinated low molecular weight compounds such as Metrizamide and heavy salts, e.g. cesium chloride. In a preferred embodiment an organosilanized colloidal silica particullate cell separation medium is used.

According to an important feature of the invention, the density gradient solution should be prepared and adjusted to a pre-determined density. In addition, the osmolality should be adjusted in the range of 280 to 320 mOsm/kg $H_2O$ to preserve cell integrity, and the pH should preferably be in the range from 6.8 to 7.8, and most preferably pH 7.4, for maintaining a physiologically isotonic density gradient, prior to use. The osmolality and pH may vary depending upon the particular conditions under which the density gradient separation method is performed. For example, the temperature at which the samples are maintained or centrifuged may necessitate modifications to the osmolality and/or pH of the density gradient material, in order to maintain the appropriate density. Such modifications of the osmolality and pH will be apparent to those skilled in the art.

Cell samples should generally be processed within a relatively short time after collection, because the density of the cells may change according to culture, collection or storage conditions. In order to maintain the optimal isolation of desired cells from body fluids, it is preferred that blood samples are used within 48 hours after collection. Most preferably, body fluids should be subjected to density gradient centrifugation within several hours after collection. The adjusted gradient solution should be added to a centrifugation tube in a volume sufficient to allow all the cells overlaid on it to separate during centrifugation. For example, a volume of about 20–25 ml of the solution is generally adequate for separating desired cells in 20 ml of whole blood.

A preferred density gradient material for use in separating cells in accordance with the present invention is an organosilanized colloidal silica (OCS) particle suspension, such as are disclosed in U.S. Pat. No. 4,927,749 to Dorn, incorporated herein by reference. One OCS density gradient material is prepared from colloidal silica by reacting and thus blocking the silanol groups with an alkyl trimethoxy silane reagent and has the structural formula:

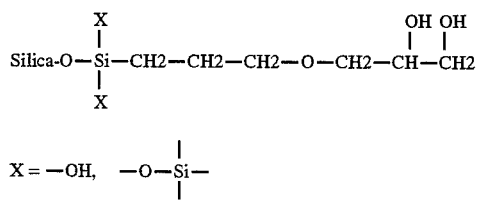

Related colloidal silicas and methods for production thereof are disclosed in U.S. Pat. No. 4,927,749 to Dorn. In a preferred embodiment, the OCS density gradient material is diluted to an appropriate specific density in a physiological salt solution supplemented with polyvinylpyrrolidone (PVP) such as PVP-10 available from Sigma Chemical Co. (St. Louis, Mo.). According to an important feature, it has been found that inclusion of at least 0.5% PVP improves the yield of functional rare blood cell types. In addition, such a concentration of PVP facilitates sterilization of the OCS density gradient material by ionizing radiation, such as E-beam or gamma irradiation. In the absence of PVP, cells exposed to the medium experience loss of functional capacity—in the case of $CD34^+$ cells, evidenced by loss of ability to form colonies (reduction of CFU). Generally, the amount of PVP to be added to an OCS cell separation suspension will depend on the subsequent purpose and treatment of the preparation. For preserving functional activity of cells exposed to the OCS preparation for relatively short periods of time, 0.5% (wt/wt) generally suffices. For longer exposures and exposure to ionizing radiation, higher concentrations of PVP may be required—as high as about 3–8% (wt/wt).

In carrying out the methods of cell separation of the present invention, it is generally preferred that the specific density of the cell separation material be within about ±0.0005 gr/ml, preferably ±0.0002 gr/ml of the specific density of the cells to be collected. The specific density of the stock solution up to the fourth digit may be determined using appropriate equipment, for example, a high precision digital density meter such as DMA 48 (Anton PAAR USA, Ashland, Va.) which measures density with an accuracy of ±0.0002 gr/ml. In addition, a physiological osmolality is preferred. In general, animal cells have a fairly wide tolerance for osmotic pressures, as evidenced by survival in media ranging from about 280–340 mOsm/kg $H_2O$, though a preferred solution osmolality for human cells is about 280 mOsm/kg $H_2O$. Osmolality of a solution is usually measured by freezing point depression of the solution, such as by a Roebling osmometer (Camlab, Cambridge, Great Britain), or by elevation of vapor pressure. These aspects of the invention are discussed further in Section 5.3, below.

An OCS particle-based density gradient medium is prepared by suspending OCS particles (U.S. Pat. No. 4,927,749) in a quantity of water sufficient to achieve near the specified density, as calculated. Dry powders of PVP and physiological salt components (generally, phosphate salts and sodium chloride) are then added according to the PVP concentration and osmolality desired, respectively. The pH of the solution is then adjusted according to standard methods, preferably to pH 7.4, and the volume is adjusted to the final desired volume. Specific density and osmolality can then be verified according to the methods discussed above.

A "PERCOLL" stock solution having osmolality of 280–320 mOsm/kg $H_2O$ can be made by adding 12 parts of "PERCOLU" with 1 part 10× Ca and Mg free PBS or 1.5M NaCl, for human cells, or adding 9 parts of "PERCOLL"

with 1 part 10× Ca and Mg free PBS or with 1 part 1.5M NaCl, for human or non-human animal cells. The osmolality of the stock solution may be adjusted appropriately, for example, to 280 mOsm/kg $H_2O$+10 for human use or 320 mOsm/kg $H_2O$+10 for animal use, according to methods known in the art, and measured as discussed above. The pH may be adjusted appropriately, preferentially to pH 7.4 if a physiologically isotonic solution is desired.

An appropriate amount of cell separation material, prepared as described above, is placed in a centrifuge tube which is preferably, but not necessarily, a cell-trap tube. The cell mixture to be separated is layered on separation medium in the tube, and the tube is subjected to centrifugation at low speed—generally about 500–1500×g. Cells having densities greater than the specific density of the cell separation material move to the lower portion of the tube, while those having densities less than that of the material remain at the interface between the cell diluent and the cell separation medium. Generally, the method of the invention is directed to collecting the lighter fraction of cells present at the interface.

5.2. Density Adjusted Cell Separation

According to a further aspect of the invention the density separation methods described herein can be augmented by adding to the cell mixture to be separated, microparticle carriers to which are attached cell specific binding molecules effective to bind selected cells in the mixture. In a preferred method, such binding molecules will be used remove from the mixture during centrifugation contaminating cells having densities approximately equal to or lighter than the cells of interest. This process, referred to herein as "Density Adjusted Cell Separation" (DACS) is described in the sections that follow.

5.2.A. Isolation of Cells using Density Adjusted Cell Sorting (DACS)

Figure 8A:
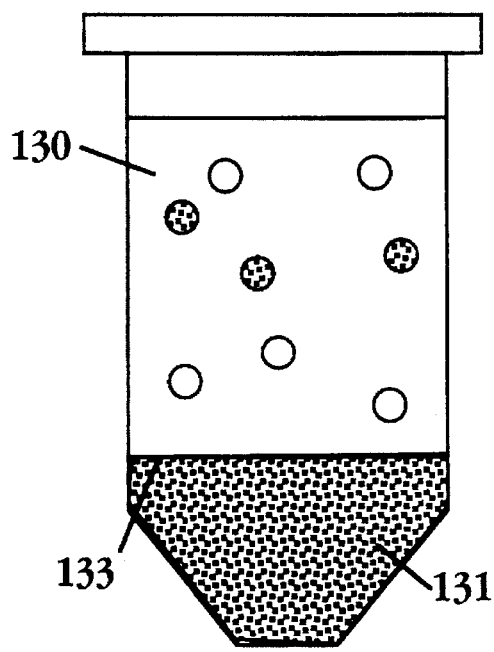
Figure 8B:
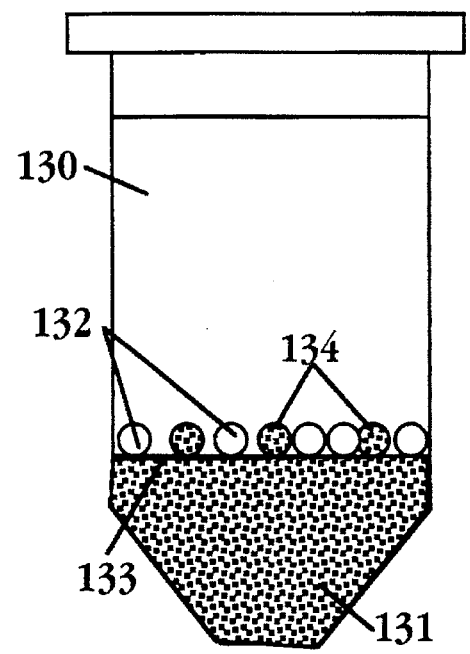

FIGS. 8 (A–D) compare density adjusted cell sorting (FIGS. 8C and 8D) to conventional density gradient centrifugation (FIGS. 8A and 8B). In both methods, solution 130 containing undesired cells 132 and desired cells 134 is layered on a density gradient material 131, forming interface 133 between solution 130 and density gradient material 131. With reference to FIG. 8B, following centrifugation, with conventional gradient centrifugation, there are still a relatively large number of undesired cell types 132 trapped at the interface with the cells of interest 134 (FIG. 8B).

Figure 8C:
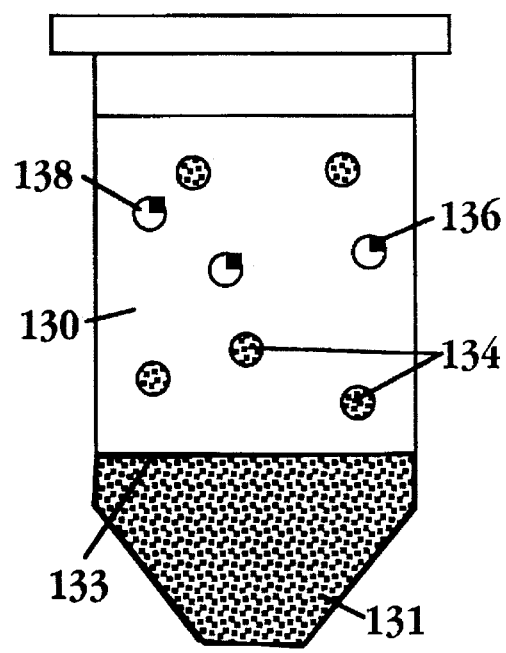
Figure 8D:
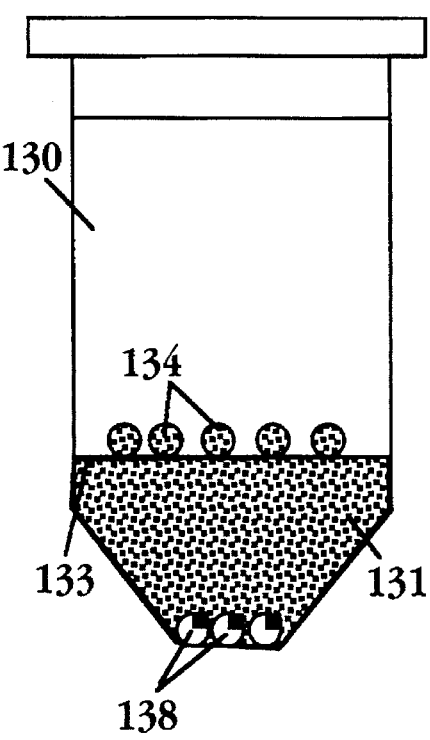

Using DACS, affinity modified carrier particles, described in Section 5.B.2 below, are added to the cell mixture to bind to undesired cells. As shown in FIG. 8C carriers 136 bind to undesired cells to form density adjusted cells 138. These cells are rendered denser and thus able to sediment during centrifugation (FIGS. 8FD). Alternatively, for cells which are heavier than the gradient density, a lighter density may be imparted to them by use of lighter carrier particles, e.g. highly porous silica particles which are rendered cell type-specific by the direct or indirect binding of cell type-specific binding agents.

When carrier particles specific for unwanted cells are mixed with a cell or tissue sample which is then overlaid onto a customized density gradient according to the methods of the invention described herein, a single centrifugation step allows for substantial enrichment of a cell type of interest from the sample. The foregoing is an example of density adjusted cell sorting applied in a negative affinity manner, i.e., to purge undesired cells, e.g. tumor cells, from a sample by using a modified carrier particle having specificity for the undesired cell population. Alternatively, density adjusted cell sorting may be applied in a positive affinity manner, i.e., to collect desired cells from a sample by using a modified carrier particle having specificity for the desired cell population. The beads may be removed from desired cells by enzymatic or chemical cleavage, or by mechanical force. For example, papain may be used to cleave a desired cell from immunoglobulins. After the first round of centrifugation and collection of enriched cells, a second round of centrifugation including density adjusted cell sorting may be performed to further enrich for the desired cell population. It can be further appreciated that another advantage of DACS is that it makes somewhat less critical the precise matching of specific densities of cells of interest and the cell separation material discussed above, since unwanted cells having similar densities can be efficiently eliminated by this procedure. Studies carried out in support of the present invention, discussed in Section 5.3.A and detailed in Example 1D, demonstrate that when complete blood from pregnant females was incubated with carrier particle-coated-anti-CD45 most leukocytes were depleted from the sample. Further studies detailed in Example 2 demonstrate that, for isolation of $CD34^+$ cells, apheresed blood from cancer patients can be directly incubated with carrier particle-coated-anti-CD45 antibodies can also provide desired leukocyte depletion. Similarly, as detailed in Example 5, this method has been used to remove ("purge") tumor cells from peripheral blood preparations.

It can be appreciated that a variety of cell type-specific binding agents may be used to target specific cell types in the blood. The selection of such binding agents will be apparent to skilled practitioners, based on the type of cell to be collected and the cell composition of the cell mixture. Useful agents include antibodies such as the leukocyte-specific antibodies, e.g., anti-CD3, anti-CD4, anti-CD5 and anti-CD8 specific for cytotoxic T lymphocytes, anti-CD12, anti-CD19 and anti-CD20 specific for B cells; anti-CD14 specific for monocytes; anti-CD16 and anti-CD56 specific for natural killer cells; and anti-CD41 for platelets. Many of these antibodies are commercially available in a form already conjugated to various types of particles (AMAC, DYNAL). In addition, cell type-specific binding agents include lectins such as wheat germ agglutinin and soy bean agglutinin, growth factors and cytokines.

Alternatively, with reference to the method of isolation of hematopoietic stem $CD34^+$ cells described herein, a positive selection procedure may also be used to cause the cells to be denser, so that they are pelleted during centrifugation. In this case, antibodies directed to CD34 coated on carrier particles are used to pellet all remaining $CD34^+$ cells. Furthermore, antibodies directed to any cell surface marker may be directly linked to heavy particles for use in density adjusted cell sorting, following conjugation methods well known in the art. It is noteworthy that when density adjusted cell sorting is applied, the specific density of the gradient is less critical, as long as the undesired cells are all rendered heavier.

5.2.B. DACS Carrier Particles

A number of commercially available carrier particles may be used in the present invention and include, for example, organic polymers, e.g. polyethylene; polypropylene; polyvinyl compounds e.g. polyvinylchloride, polyacrylonitrile, polyacrylate, polymethacrylate, polycarbonate and copolymers thereof; polystyrene latex; nylon; polyterephthlate; and the like, or inorganic polymers, e.g. glass or silica particles; cellulose, Dextrans, polysaccharides, e.g. agarose, cellulose, Sepharose, Sephadex, etc., or combinations thereof. The carrier particles may be from naturally occurring polymers, modified naturally occurring polymers and synthetic addition and condensation polymers.

A preferred carrier particle of the present invention is a silica particle between 0.1–5.0 microns coupled to an aminopropyl group and having a density of greater than 1.08 gr/ml. U.S. Pat. Nos. 4,927,750 and 4,927,749, issued May 22, 1990, describe examples of modified silanes which may be used in the present invention as carrier particles. Various silica carrier particles are commercially available from, for example, Bangs Laboratories, Inc., Carmel, Ind., Pharmacia, Sigma Chemical Company, Bio-Rad, AMAC, Inc., etc.

A preferred heavy carrier particle of the present invention is a silica bead having a density greater than the density of the density gradient material selected according to methods described infra and a particle size of 0.1 micron to 5.0 micron such that the carrier particles will be pelleted upon centrifugation. Such a particle may additionally be silanized, as detailed in Example 4B herein. The preferred particle will also have the capability of binding, either directly or indirectly, to cell type-specific binding agents, or may be derivatized to such agents.

It has been found that, particularly in the case of organosilanized colloidal silica particles, such as those described by Dorn U.S. Pat. No. 4,927,749, it is useful to supplement such particles with at least 0.5% polyvinylpyrrolidone (PVP), to reduce cell toxicity, as discussed with reference to OCS particle-based cell separation media, above.

A preferred lighter carrier particle useful in the present invention is one having a density less than 1.0 and a particle size of 0.1 to 5.0 microns, such that the particles will float above the density gradient upon centrifugation as well as one having the capability of binding, either directly or indirectly to cell type-specific binding agents. Such low density carrier particles can be obtained from 3M, St. Paul, Minn. catalog no. H50/1000, termed "Scotchlite microbeads".

Polystyrene latex particles (available from Sigma Chemical Company), may also be used as low density particles; however, due to surface hydrophobicity, such particles characteristically exhibit non-specific binding. Such non-specific binding may be reduced by treatment methods, such as pre-absorption with protein or addition of methacrylic acid groups, known in the art. Latex particles may be transformed into high density particles by addition of a metal group.

Also available for use in the invention are polyacrylamide carrier particles, such as Bio-Rad polyacrylamide beads coupled to either primary amino functional groups (Affi-Gel 701 beads) or carboxyl functional groups (Affi-Gel 702 beads or Immunobead Reagent).

The preparation of small, stable, spherical particles which are bio-compatible and/or biodegradable, i.e., do not interact non-specifically with cells or other biological components and which contain functional groups to which specific proteins and other bio-chemical molecules can be covalently bonded, is disclosed in U.S. Pat. No. 3,957,741, issued May 19, 1976. The hydroxyl or amino groups can be activated by cyanogen bromide for covalent bonding of protein and other chemicals containing amino groups to the polystyrene latex.

U.S. Pat. No. 4,035,316, issued Jul. 12, 1977, describes the method for making cell specific, variable density, polymeric microspheres derivatized with amine-, hydroxyl- and/or carboxyl-functional groups and having a density of at least 1.30 gr/ml preferably above 1.40 gr/ml or a density below 1.15 gr/ml and preferably below 1.08 gr/ml.

A process for forming highly uniform silica spheres is described in U.S. Pat No. 4,983,369, issued Jan. 8, 1991.

Also included within the scope of the present invention are carrier particles or carrier particles to which are attached a magnetic substance allowing for enhanced separation of cells through use of a magnetic field. U.S. Pat. No. 4,777,145, issued Oct. 11, 1988 describes an immunological assay method using magnetic particles. AMAC, Inc., subsidiary of IMMUNOTECH, S.A. (France) provides magnetic microspheres coated with monoclonal antibody, e.g. anti-CD4, anti-CD8, anti-CD19, anti-CD45, etc.

5.2.C. Cell Type-Specific Binding Agents

The cell separation methods of the present invention may include the use of cell type-specific binding agents having specificity for either the desired or undesired cell populations which may be bound either directly or indirectly to a carrier particle, as described in the previous section. As defined herein, "cell type-specific binding agents" include, for example, antibodies or antigens; peptides or polypeptides; growth factors or cytokines; lectins and agglutinins or other affinity molecules known in the art to have specificity for either the desired cell populations or the undesired cell populations. Many of these agents are commercially available or can be produced according to well known methods.

Commercially available cell type-specific binding agents that may be used in the present invention, include, but are not limited to, antibodies, antigens, polypeptides, peptides, growth factors, membrane bound receptors, small organic molecules, lectins, and agglutinins.

A variety of antibodies known to those of skill in the art, commercially available or available through cell culture depositories, e.g. the ATCC, Rockville, Md. or the NRLL, Peoria, Ill., may be used in the present invention as cell type-specific binding agents depending upon the cell type desired to be isolated or enriched. These include, but are not limited to, antibodies specific to hematopoietic and lymphoid antigens such as, anti-CD2, anti-CD2R, anti-CD3, anti-CD4, anti-CD5 and anti-CD8 specific for CTL's, anti-CDw17 specific for granulocytes, monocytes and platelets, anti-CD18 specific for leucocytes, anti-CD71 specific for activated T- and B-cells, macrophages, proliferating cells, antibodies to cytokines and growth factors (e.g. IL1–IL13, EGF, IGF I and II, TGF-$\alpha$ and $\beta$, TNF-$\alpha$ and $\beta$, FGF, NGF, CIF, IFN-$\alpha$ and $\beta$, CSF's), hormones, cellular or tumor associated antigens or markers, adhesion molecules, hemostasis molecules, and endothelial cells. The precise agents to be used will depend upon the antigenicity of the desired cell and the composition of the cell mixture from which it is to be isolated. According to an important feature of the present invention, tumor cells may be depleted from a cell sample using DACS. Here, a tumor antigen is selected that is specific for the tumor cell type or types to be depleted from the sample. As exemplified herein, tumor cell antigens that are specific for B cell lymphoma include CD9, CD10, CD19 and CD20; tumor cell antigens that are specific for certain breast tumors include Her2/Neu and estrogen receptors. Additional exemplary tumor antigens are described in Section 5.3.C, below. Skilled practitioners will be able to determine optimal carrier agent composition, based on knowledge of the characteristics of the particular cell to be bound by the carrier particles and the factors discussed above.

Antibodies useful as affinity molecules can be produced according to standard polyclonal or monoclonal production methods known in the art. Useful antibodies include, but are not limited to, polyclonal, monoclonal, chimeric, single chain, Fab fragments and fragments produced by a Fab expression library and phage display expression library.

According to an important feature recognized by the invention, discussed in Section 5.2.D and detailed in Example 2.D.2, undesirable non-specific binding of cells to antibody-based preparations is greatly diminished by use of either Fab fragments or polyethylene coatings. Without ascribing to a particular theory, it is observed that both the Fc preparation reduces exposure of the cells to the carbohydrate-rich Fc fragment of immunoglobulins. It is appreciated that other manipulations, such as deglycosylation of the immunoglobulin, may achieve the same result. It is noted that PEG treatment may reduce ionic interactions between the cell proteins and charged surfaces.

Commercially available agglutinins may be used in the present invention. These include, but not limited to, wheat germ agglutinin, peanut agglutinin, soy bean agglutinin, phytohaemagglutinin, and leucoagglutinin, and are commercially available, for example, from Pharmacia Fine Chemicals (Piscataway, N.J.).

5.2.D. Coupling of Cell Type-Specific Binding Agents to Carrier Particle

Immobilization of the cell type-specific binding agent to the carrier particles can be achieved by a variety of techniques known to those of skill in the art. Such techniques are described in, for example Bangs (*The Latex Course* (1992), available from Bangs Laboratories, Inc. Carmel, Ind.); Yoshioka et al., 1991, *Journal of Chromatography* 566:361–368; Pope et al., 1993, *Bioconjugate Chem.* 4:166–171); Harlow and Lane, 1988, *Antibodies: A Laboratory Manual*, Colorado Spring Harbor Laboratory; *Avidin-Biotin Chemistry: A Handbook*, 1992, ed. Savage et al., pub. PIERCE; Hermanson et al., *Immobilized Affinity Ligand Techniques*, 1992, pub. Academic Press, Inc. The foregoing references are incorporated herein by reference for these teachings.

Binding techniques include, for example, simple physical absorption or adsorption where the cell type-specific binding agent is bound directly to the carrier protein without the use of functional groups; complex adsorption where a second binding agent, e.g. BSA, is co-adsorbed to the carrier particle and forms the basis for binding functional groups; and covalent bonding of the binding agent to the carrier particle. The biotin-strepavidin affinity system may also be used in the present invention to bind cell type-specific binding agents to the carrier particles. Various particle surface chemical reactions for covalent coupling are known to those of skill in the art and include, but not limited to, carboxylic acid, primary or aliphatic amine, aromatic amine or aniline, chloromethyl (vinyl benzyl chloride), amide, aldehyde, hydroxyl, thio, hydrazide, epoxy, sulfate and sulfonate. Other coupling chemical reactions are described in Bangs, Uniform Latex Particles (1984).

For use in the present invention, it is preferred that the direct or indirect binding of the cell type-specific binding agent to the carrier particle be performed in excess binding agent to allow for maximum coverage of the surface of the carrier particle, thereby reducing the potential for non-specific binding and bead clumping. Carrier particles may also be subjected to blocking agents, e.g. casein, gelatin and TWEEN detergent to fill any unoccupied sites on the carrier particle in order to reduce non-specific binding.

In one illustrative example, carboxyl groups on the carrier particle surface can be made reactive with the available amino groups on the cell type-specific binding agent. Other means of binding cell type-specific binding agent to particle surfaces include employing activated carboxylic acids, carbodiimides, i.e., (1-ethyl-3-(3-dimethylaminopropyl) carbodiimide or EDAC, imido esters, active alkyl halides, etc., to form amido, amidine or amino linkages.

A preferred carrier particle of the present invention is an aminopropyl silica particle wherein the amino groups have been coupled to the silica particle through a glutaraldehyde linkage, see Example 4.

In experiments carried out in support of the present invention, several different procedures were tested, in order to maximize specific depletion and minimize non-specific depletion during DACS. As detailed in Example 2, Section D.2, DACS beads were covalently coated either with GAM-IgG or F(ab)$_2$ GAM-IgG (East Coast Biologicals) in a random orientation or GAM-IgG in a specific orientation to maximize the availability of the Ig binding sites to attach to antigen. Polyethylene glycol (PEG) (Shearwater) was used to coat the beads in certain cases to reduce the non-specific affinity of the beads for protein or cells.

As described in Section 5.3.B. below, manipulations that resulted in removing or blocking the $F_c$ region of the antibodies bound to the beads reduced non-specific depletion of cells from the interface. More specifically, reduced non-specific depletion was observed using beads that were coated with polyethylene glycol (PEG).

5.3. Isolating Selected Cell Types

The present invention provides methods for isolation or enrichment of a desired cell type from an in vivo or in vitro mixture, when the specific density of the cell type is known. Exemplary specific cell types isolated by this method are discussed below.

Preferably, the method includes loading one of the embodiments of the cell-trap cell separation apparatus described in Section 5.1.A., with a cell separation medium having a specific density that is within ±0.0005 gr/ml of the specific density of the, then centrifuging the apparatus. The desired cells are then collected from the upper portion of the centrifugation tube.

While use of the cell-trap centrifugation apparatus aids in the convenience and efficiency of the method of the invention, it should be noted that the invention is based, in part, on the specificity and accuracy of the density gradients used. That is, the density gradients must be prepared such that their densities are accurate to within at least ±0.0005 gr/ml, and preferably within ±0.0002 gr/ml, of the specific density of the desired cell, at a defined osmolality. Thus the invention may be practiced using a standard centrifugation tube, as well as a cell-trap tube, so long as the density is well defined. Examples 1–3 herein describe use of specific density cell separation media with and without the cell-trap.

Following centrifugation, the desired cell will be found at the interface between the gradient material and the cell sample solution. Material at the interface can be collected, then centrifuged to concentrate it, if desired. Alternatively, when it is preferable to retain the desired cell material in a closed system, the centrifugation can be carried out in a closed system or in a centrifugation syringe having a cell-trap configuration, such as described in Section 5.1.A.

If desired, improved purity of the desired cell type can be achieved by adding to the above procedure a density-adjusted cell sorting procedure, as described in Section 5.2. As described therein, prior to centrifugation, the cell sample containing the desired cell is exposed to carrier particles having bound thereto cell type-specific binding agents effective to bind and remove unwanted cells.

For therapeutic applications, it is generally preferred that the desired cell population remain in the interface between the gradient material and the cell sample solution. Alternatively, if the desired cells are attached to beads in the pellet, they may be cleaved enzymatically, chemically or mechanically from the beads by methods known to those of skill in the art, including the use of proteolytic enzymes, e.g. papain.

Cells isolated or enriched by the cell separation methods described herein may be used for a variety of diagnostic and therapeutic uses. The isolated or enriched cells may be cultured under sterile conditions and subjected to cytogenetic analysis, e.g. the detection of chromosomal abnormalities and gender determination. The isolated or enriched cells may be reacted with molecular probes for more sensitive detection using PCR and FISH. The isolated or enriched cells may also be used therapeutically, for example, for allogeneic and autologous transplantation.

The following sections provide specific guidance for isolation of several therapeutically and/or diagnostically useful cell types that are isolated in accordance with the principles of the present invention.

5.3.A Isolation of Fetal Cells from Maternal Blood

It has now been established that a small number of fetal cells circulate in maternal blood, including lymphocytes, trophoblasts, and nucleated red blood cells. These cells provide an alternative source of genetic materials for prenatal testing (Simpson and Elias, 1993, JAMA 270:2357). However, the rarity of such cells in maternal blood (estimated 1 in $10^7$–$10^8$ maternal blood cells) dictates the need for enhanced methods of isolation and detection (Holzgreve et al., 1992, J. Reprod. Med. 37:410). While several detection methods have been made available through recent advances, including polymerase chain reaction (PCR) and fluorescence in situ hydribization (FISH), the major difficulty in the routine use of maternal blood for prenatal diagnosis is the inability to enrich the small number of fetal cells in a mixture of maternal cells to yield reliable diagnostic results.

Several techniques have been proposed to meet this need, including fluorescence-activated cell sorting (Herzenberg et al., 1979, Proc. Natl. Aca. Sci. U.S.A. 76:1453), magnetic-activated cell sorting (Ganshirt-Ahlert et al., 1992, Am. J. Obstet. Gynecol. 166:1350) or a combination of these procedures (Ganshirt-Ahlert et al., 1992, Am. J. Hum. Genet. 51:A48). While these procedures have been able to partially enrich fetal cells, they are both costly, because of the need for sophisticated instrumentation, and cumbersome, due to multiple steps involved. More importantly, such methods result in substantial cell loss, thereby reducing the number of fetal cells available for subsequent analysis.

Of the fetal cell types known to be present in maternal blood during pregnancy, nucleated red blood cells are the most attractive candidates for enrichment and detection. The nuclei of these cells provide a source of genetic material for the application of techniques such as PCR and FISH. There are also several well-known commercially available antibodies that may be used to characterize the cells, such as anti-CD71 and anti-glycophorin A. Another major advantage for targeting fetal cells in the erythroid lineage is their relatively short life span. Unlike lymphocytes, these cells should not persist from prior pregnancies to interfere with the analysis of maternal blood.

The apparatus and methods of the invention can be used to isolate fetal cells from cell mixtures. In particular, the method can be used to isolate rare fetal cells from maternal blood for purposes of prenatal diagnosis by genetic testing.

This aspect of the invention is based, in part, on Applicant's discovery that colloidal silica (PERCOLL) solution adjusted to a density of 1.0720±0.0005 gr/ml, an osmolality of 280 mOsm/kg $H_2O$, and pH 7.4 efficiently separates fetal cells from the majority of adult blood cells when complete blood without prior separation or dilution is overlaid on the gradient solution. In addition, the method is improved by using cell-trap centrifugation tubes described herein which contain a constriction to allow the cells in the upper portion (i.e., above the constriction) to be decanted as opposed to using a pipette to collect the cells which results in increased cell loss.

In practice, peripheral blood may be collected from pregnant females in anti-coagulant-containing tubes or by apheresis or leukopheresis. Complete blood does not need to be processed or diluted prior to centrifugation. However, since the methods enrich fetal cells based on their specific buoyant density, it is important that the cells are subject to separation within a relatively short time after collection, because the density of the cells changes according to their culture or storage conditions. Therefore, in order to obtain optimal enrichment of fetal cells from maternal blood, it is preferred that the blood samples are used within 48 hours after their collection. Most preferably, blood samples should be subjected to density gradient centrifugation within several hours of collection.

The present invention may be practiced by overlaying whole blood on a defined density gradient in a cell-trap centrifugation tube. After centrifugation the cells in the interface are collected and pelleted by another centrifugation step to remove cell debris, platelets, and the remainder of the density material. Thereafter, the cells are depleted of the majority of leukocytes by their reactivity with an antibody, such as anti-CD45; the remaining red blood cells analyzed by flow cytometry, and the fetal cells within this population identified by FISH using specific molecular probes.

The efficiency of the method is can be further improved when it is combined with density adjusted cell sorting, described in Section 5.2, above. Thus, this specific embodiment of the invention provides for a rapid and high yield procedure to enrich for fetal cells from a large blood volume. The increased number of fetal cells in the resultant cell population enhances the sensitivity and accuracy of techniques commonly applied to genetic testing.

In an effort to further minimize cell loss, but achieve platelet removal, a second centrifugation step for pelleting the fetal nucleated red blood cells may also be carried out in a cell-trap tube.

Example 1 details materials and methods for isolating nucleated fetal cells according to the methods of the invention. Table 1 presents results from an experiment in which "PERCOLL" was used as the density gradient material in a one-step gradient separation according to the present invention. "PERCOLL" was prepared and adjusted to physiologic osmolality of 280 mOsm/kg $H_2O$ and physiologic pH of 7.4, as described in Example 1.

Summarizing the results of the experiments detailed in Example 1, the specific density of the cell separation medium was adjusted to ±0.0002 gr/ml of the target density, as described. Cells were harvested from the interface, and percent fetal and pellet and interface and tested for yield by marker antigen characterization. According to the discovery of the present invention, a density of 1.0720 gr/ml or above produced at least about 50% recovery of nucleated cells from the total nucleated cell population prior to centrifugation; there was a substantial contamination of the interface with mature red blood cells when the gradient was adjusted to a density of 1.0750 gr/ml or above.

From the foregoing it will be appreciated that in order to recover a high percentage of total nucleated cells from the starting cell mixture, but reduce mature red blood cell contamination a density of 1.0720 gr/ml is optimal. Moreover, this density should be defined with a precision ±0.0005 gr/ml, and preferably, of ±0.0002 gr/ml.

When four cell separation methods were compared for nucleated red blood cell yield, the two methods of the present invention produced substantially higher percentages of nucleated red blood cells than the conventional method. Table 1 shows results of experiments in which cells were isolated by four different methods. In all but the DACS treated sample, centrifuged samples were depleted with anti-CD45 antibodies coupled to magnetic beads, according to methods known in the art. From these results, it can be seen that cell-trap tubes containing "PERCOLL" at a density of 1.0720±0.0002 gr/ml produced about an 8-fold higher number of nucleated fetal blood cells than the conventional method using stock "FICOLL" at a density of 1.077±0.001 gr/ml and 320 mOsm/kg $H_2O$. Thus, this method resulted in a statistically significant increase the total number of fetal nucleated red blood cells available for subsequent genetic testing, compared to conventional methods. In addition, the procedure also enriched for fetal trophoblast cells. Further inspection revealed fetal cells at different stages of differentiation present in the enriched fractions. Furthermore, the DACS method produced comparable results to the method requiring magnetic field depletion of $CD45^+$ undesired cell populations.

Any tubes suitable for use in centrifugation may be used for the practice of the invention. In a preferred embodiment, the present invention is directed to a cell-trap tube for the density separation of fetal cells. For the purpose of the present invention, a cell-trap tube refers to a centrifugation tube which contains within it a constriction or a trap and a properly adjusted density gradient material filled to a level above the constriction so that cells having a certain density pass through the opening of the constriction to form a cell pellet in the compartment below the constriction during centrifugation.

ral killer cells; and anti-CD41 for platelets. Many of these antibodies are commercially available in a form already conjugated to various types of particles (AMAC, DYNAL). Alternatively, for positive selection of nucleated red blood cells, mature red blood cells may be removed from the sample and antibodies directed to glycophorin A or CD71 coated on carrier particles may be used to pellet all remaining nucleated red blood cells.

The nucleated red blood cells enriched by the methods described above were subsequently examined for the presence of fetal cells. The enriched cell preparations obtained from donors who were known to be carrying a male fetus were selected for use in FISH analysis. The cells were incubated with an X-chromosome-specific probe linked to a green fluorescence dye and a Y-chromosome-specific probe linked to a red fluorescence dye. Fetal nucleated red blood cells were identified as cells with nuclei that contained a red spot and a green spot under a fluorescence microscope, while other cells were of maternal origin. The far right column of Table 2 shows that there was an eight fold increase in the number of XY (fetal) chromosomes in the cell populations prepared by one method of the invention over that by the conventional method (e.g., FICOLL isolation method). It is of further interest to note that the method of using cell-trap and "FICOLL" also increased the number of fetal nucleated red blood cells to the detection threshold over the same gradient practiced without cell-trap tubes, indicating that the cell-trap itself was useful in increasing cell yield.

It should be noted that in order to obtain reliable diagnostic results involving techniques such as FISH, it is generally necessary to enrich the fetal cells to at least 0.1% of the final cell preparation in order for the enrichment method to be used as a routine procedure. The method of the invention is shown herein to have clearly exceeded this limit by demonstrating enrichment of fetal cells to a level of 41 cells/10,000 total cells analyzed.

5.3.B Isolation of Hematopoietic Progenitor $CD34^+$ Cells

Transplantation of bone marrow and peripheral blood-derived hematopoietic progenitor cells is performed in the

TABLE 1

| | Cell Number Before Separation | After Density Centrifugation | After Anti-CD45 Depletion | Percentage of Nucleated Red Blood Cells | Percentage of Nucleated Fetal Red Blood Cells |
|---|---|---|---|---|---|
| Conventional Method Using "FICOLL" | $10^7$ | 14% | 0.2% | 0.01% | Undetectable |
| "FICOLL" plus Cell-trap | $10^7$ | 16% | 0.17% | 0.01% | 0.05% |
| "PERCOLL" Plus Cell-trap | $10^7$ | 54% | 1.7% | 0.21% | 0.41% |
| "PERCOLL" Plus Cell-trap Plus Density Adjusted Cell Sorting | $10^7$ | 3.3% | Not Applicable | 0.23% | Not Done |

Percentage of Nucleated Cells Recovered from Interface

In the foregoing experiments, DACS treatment of the maternal samples used anti-CD45 as an agent to deplete unwanted blood cells from the interface of the density gradient. A variety of other cell type-specific binding agents may be used to target specific cell types in the blood. These agents encompass antibodies such as anti-CD3, anti-CD4, anti-CD5 and anti-CD8 specific for CTL's anti-CD12, anti-CD19 and anti-CD20 specific for B cells; anti-CD14 specific for monocytes; anti-CD16 and anti-CD56 specific for natuclinic for the treatment of cancer and hematopoietic disorders. Hematopoietic progenitor cells migrate to and reconstitute the bone marrow microenvironment after transfusion. Depending on their degree of differentiation these progenitor cells either contribute to short term engraftment or to long term engraftment of the bone marrow microenvironment.

In general, there are two major types of cells that are considered to be necessary for successful transplantation and engraftment—colony forming unit cells (CFU), that provide short term bone marrow engraftment preventing infection in the patient during the time immediately following the radio- and chemotherapy, and long term culture initiating cells (LTC-IC), that establish a long lasting, self-renewing myeloid and lymphoid system in the patient. The hematopoietic progenitor cell population expressing the CD34 surface antigen contains both CFU and LTC-IC. Hence, the present invention relates to methods for enriching total $CD34^+$ cells.

In addition, when the bone marrow cells or other progenitor cell source contain contaminating tumor cells that must be purged prior to re-infusion in an autologous setting, the large number of total cells with a low percentage of $CD34^+$ cells makes it technically difficult to perform adequate purging of tumor cells. Thus, there remains a need for a simple method for enriching $CD34^+$ progenitor cells from a cell mixture containing higher numbers of these cells that are amenable to efficient purging of residual tumor cells for use in subsequent transplantation.

In an effort to address these problems, investigators have focused on the use of anti-CD34 antibodies. Such procedures involve positive selection, such as the passage of white blood cells over a column containing anti-CD34 antibodies or binding of cells to magnetic bead-conjugated anti-CD34 antibodies or by panning on anti-CD34-coated plates, and collecting the bound cells. However, the affinity based methods have limitations in terms of practical utility in that they are costly and time-consuming.

Alternative methods for enriching hematopoietic progenitor cells have been reported which utilize various forms of density gradient centrifugation (Olofsson et al., 1980, Scan. J. Haematol. 24:254; Ellis et al., 1984, J. Immunol. Meth. 66:9; Lasky and Zanjani, 1985, Exp. Hematol. 13:680; Martin et al., 1986, Brit. J. Haematol. 63:187). However, all reported methods use agar colony assays to identify hematopoietic progenitor cells after enrichment. It is known that the progenitor assays only detect committed precursor cells which occupy less than 1% of the $CD34^+$ population. It is therefore uncertain whether these methods can in fact enrich for the early progenitor cells or stem cells which can permanently engraft and reconstitute a lymphohematopoietic system, as they have not been tested clinically. Furthermore, there is no indication from the published reports that any of these procedures are able to obtain adequate numbers of cells for clinical use.

The present invention provides methods of rapid and high yield enrichment of progenitor cells based on density gradient centrifugation. More specifically, the invention utilizes a precisely determined density of a density gradient solution, preferably contained within a specially designed cell-trap centrifugation tube to maximize cell yield.

A major advantage of the methods described herein is that a large volume of apheresed blood may be directly placed on the density gradient. Peripheral blood may be collected in anti-coagulant-containing tubes or by apheresis or leukopheresis. In addition, the single step process reduces the total volume of infusate by 70-90%, thereby reducing the amount of cryopreservative required. After enrichment, the final cell preparation represents between 10% to 30% of the starting cell number, but contains between 70% and 100% of the starting number of $CD34^+$ cells and colony-forming CFU's. Due to this high yield (70% to 100%) of $CD34^+$ cells, a single peripheral blood collection may yield sufficient $CD34^+$ cells to reconstitute the hematopoietic and immune system of patients undergoing ablative chemotherapy. This cell population also contains a reduced number of T lymphocytes, but a substantial number of natural killer cells and natural suppressor cells. Additionally, the procedure is rapid, convenient and cost effective. Processing of a complete sample requires no specialized instrumentation and can be performed by one person in a time frame of one hour.

The present invention also provides for purging from the bone marrow cells or other progenitor cell source contaminating tumor cells, prior to re-infusion of the progenitor cells in an autologous setting for use in subsequent transplantation.

For purposes of purging, the density of a given tumor cell is determined by centrifuging a tumor containing sample on a discontinuous density gradient ranging from 1.0490 to 1.0640 gr/ml. The majority of undesirable, non-tumor cells represent cells of the immune and hematopoietic system and have a density in the range of 1.0610 to 1.0770. The density of tumor cells generally falls within the 1.0490 to 1.0580 gr/ml density range. The density of the cell separation medium is determined to an accuracy of within ±0.0005 gr/ml, preferably ±0.0002 gr/ml of the specific gravity of the desired progenitor cells. Thus tumor purging can be accomplished by a two step process, in which the progenitor cells are first pelleted through a cell separation medium capable of retaining tumor cells. Alternatively, the DACS technique can be used to remove tumor cells in a one-step process, according to the methods described below.

For enrichment of $CD34^+$ cells from blood, such as peripheral or umbilical cord blood, the cell separation medium should be adjusted to a density of 1.0605±0.0005 gr/ml, a physiologic osmolality of 270–290 mOsm/kg $H_2O$ and physiologic pH 6.8–7.8. More preferably, the density will be 1.0605±0.0002 gr/ml, and the osmolality will be 280 mOsm/kg $H_2O$, at pH 7.4.

In illustrative examples, apheresed blood from a cancer patient treated with G-CSF has been directly loaded into cell-trap centrifugation tubes containing either an OCS particle-based cell separation solution or a PERCOLL solution filled to a level above the constriction. In each case, the solution was adjusted to the preferred density of 1.0605±0.0005 gr/ml, osmolality of 280 mOsm/kg $H_2O$ and pH 7.4. The density of the cell separation solution may be adjusted on a densitometer to precisely define its accuracy up to at least the fourth decimal place. It should be noted that a variety of other gradient materials may be used to achieve progenitor cell enrichment, and they include, but are not limited to, "FICOLL", "FICOLL-HYPAQUE", cesium chloride, any protein solution such as albumin or any sugar solution such as sucrose and dextran. However, the density gradient solution should be prepared and adjusted to the appropriate density, osmolality and pH according to that disclosed herein, prior to its use. The gradient solution should be added to a centrifugation tube in a volume sufficient to allow all the cells having a higher density to pass through the gradient during centrifugation. For example, a volume of about 20–25 ml of the solution is generally adequate for separating cells in 20 ml of apheresed blood samples.

Any tubes suitable for use in centrifugation may be used for the practice of the invention. In a preferred embodiment of the present invention, the cell-trap centrifugation apparatus described in Section 5.1.A. will be used for the density separation of $CD34^+$ cells.

Isolation of $CD34^+$ cells from Peripheral Blood

Co-owned parent patent application U.S. Ser. No. 08/299, 469, incorporated herein by reference, describes studies in which "PERCOLL" was used at physiologic osmolality of 280±10 mOsm/kg $H_2O$ and pH of 7.4 as the density gradient material to isolate $CD34^+$ cells from apheresed blood. According to the invention described therein, at this osmolality, $CD34^+$ cell recovery was optimal at a specific density of 1.0605 gr/ml. It was further determined that an accuracy of within ±0.0005 gr/ml was preferable to ensure high yield enrichment of $CD34^+$ cells. Further it was shown that these conditions resulted in a 2-fold increase in $CD34^+$ yield, as compared to isolation by conventional methods. Moreover, the cell separation procedure by the 1.0605 gr/ml density gradient did not change the functional potential of hematopoietic progenitor cells to form colonies.

In addition, as part of the foregoing studies, the quantitative distribution of the CFU over the gradient was determined. Only minor numbers of CFU were observed in the pellet fractions, and approximately 90–100% of the CFU were present in the interface of 1.0605 gr/ml "PERCOLL". Also, it was observed that 100% of the CFU-GEMM were present in the interface (FIG. 9). LTC-IC assays showed that between 90–100% of the uncommitted hematopoietic stem cells were present in the interface (FIG. 10).

The foregoing data demonstrate that centrifugation of apheresed blood on a single-layer gradient adjusted to 1.0605±0.0005 gr/ml resulted in a minor non-specific loss (10% or less) of the total cell product. However, while the interface represented approximately 30% of the total cell number, this cell population contained 70–90% of the $CD34^+$ cells and more than 90% of the CFU's. The interface contained 100% of the CFU-GEMM, and since CFU-GEMM represented progenitor cells with a low degree of hematopoietic commitment and a limited degree of self renewal, the interface also contained the uncommitted hematopoietic stem cells. The results obtained with the LTC-IC assays further support this conclusion. This simplified procedure allows the automation of $CD34^+$ cell enrichment in a completely closed system. Furthermore, experiments performed in cell-trap tubes produced similar results with an even greater degree of consistency.

Density Adjusted Cell Sorting: $CD34^+$ enrichment

FIGS. 11(A–F) shows the result of a representative experiment in which $CD34^+$ cells were enriched using the DACS procedure in conjunction with the density method of the invention, by removing contaminating cells with an anti-CD45 mAb coupled to a heavy carrier (such as magnetic beads or aminopropyl glass beads). As shown, the total cell number was reduced 82% and the CD34 yield was around 40%. CD34 purity was increased from 2% to approximately 20%. Since the anti-CD45 antibody removed also some of the $CD34^+$ cells, it is appreciated that this method could be improved by using a mixture of other antibodies to deplete non-stem cells.

To examine non-specific cell losses during DACS, experiments were performed using buffy coat peripheral blood mononuclear cells (PBM) and DACS beads in the absence of monoclonal antibodies. As detailed in Example 2 (Section E.2), DACS beads were made using either intact GAM-IgG or $F(ab)_2$ GAM-IgG to test the theory that Fc receptor mediated binding of cells to IgG-coated DACS beads contributed to non-specific depletion. The results in FIG. 12 demonstrate that there was no non-specific depletion of cells when GAM-IgG $F(ab)_2$ coated DACS beads were used compared to DACS beads with intact GAM-IgG. DACS beads coated with GAM-IgG, linked via the glycosylated site on the Fc region, also demonstrated reduced non-specific depletion of cells when compared with DACS beads with GAM-IgG in a random orientation (FIG. 13). These results demonstrate that removing or blocking the Fc region of the GAM-IgG leads to a reduction in non-specific depletion of cells.

The foregoing results show that Fc Receptor (FcR) mediated binding of cells to DACS beads may be responsible for some of the non-specific depletion of $CD34^+$ cells observed during DACS treatment. This is further illustrated by the site-specific coupling which results in a reduction of non-specific loss of cells due to blocking of the glycosylated areas of the Fc portion of the immunoglobulin molecule, as described above. However the use of BSA-coated DACS beads has demonstrated that FcR-mediated binding is not usually responsible for all the non-specific depletion of cells. Ionic interactions between the cell and the bead surface are also likely to be involved. To investigate this possibility, DACS beads coated with PEG sandwiched between the bead surface and the GAM-IgG were made. This was done to exploit the ability of PEG to reduce ionic interactions between proteins and charged surfaces. The results in FIG. 14 from an experiment comparing PEG-GAM-IgG-coated DACS beads with DACS beads with GAM-IgG in the absence of PEG demonstrated that the use of PEG is associated with a reduction in non-specific depletion of cells.

Non-specific depletion of $CD34^+$ cells during DACS

Reduction in non-specific depletion by modification of the DACS bead coating is particularly important in the context of the negative enrichment of rare cells such as $CD34^+$ cells, NK cells, natural suppressor cells, dendritic cells, fetal nucleated cells, and the like, where it is important to maximize the yield of cells. For example, experiments to define the non-specific loss of $CD34^+$ cells demonstrated that the use of $F(ab)_2$ coated DACS beads lead to a reduction in the non-specific loss of $CD34^+$ cells (FIG. 15). Likewise using DACS beads coated with GAM-IgG1 bound via the glycosylation site of the Fc region also reduced non-specific depletion of $CD34^+$ cells when compared with DACS beads with GAM-IgG in a random orientation (FIG. 16).

Isolation of $CD34^+$ cells from Bone Marrow

In studies carried out in support of the present invention, bone marrow cells collected by aspiration, according to standard clinical procedures, from healthy donors were obtained from the Bone Marrow Transplantation Laboratory of the Stanford University School of Medicine, Palo Alto, Calif. $CD34^+$ cells were enriched from the bone marrow cell fraction by centrifugation over an OCS gradient having a specific density of 1.0685 gr/ml at 280 mOsm/kg $H_2O$, pH 7.4, prepared and formed in accordance with the methods of the present invention, as described in Example 2C.

FIGS. 17 and 18 summarize results of isolation studies on bone marrow cells processed on the 1.0685 gr/ml OCS suspension. FIG. 17 shows percent recovery of total cells, $CD34^+$ cells, T lymphcytes and red blood cells (RBC) from the entire gradient (interface+pellet). FIG. 18 shows the percent recovery of the same cell fractions from the interface of the gradient following centrifugation. Data presented in both figures were calculated by dividing each fraction by the total number of cells initially loaded on the gradient.

From FIG. 17, it can be seen that over 90% of cells initially loaded on the gradient were recovered from the interface and pellet. Since the loss of $CD34^+$ cells was comparable to the approximate loss of total cells (10%), no preferential loss of these cells was observed in the system.

FIG. 18 shows that while only 26±10% of total cells was recovered from the interface, this fraction contained 91±9% of the $CD34^+$ cells, 10% of T lymphocytes, and essentially no red blood cells. These studies demonstrate substantial enrichment of CD34$^+$ cells, coupled with depletion of T lymphocytes, by the density gradient procedure of the present invention. As discussed in the following section, these characteristics recommend the preparation for use in allogeneic stem cell transplantation.

Additional indications for CD34$^+$ cells Graft versus Host Disease (GvHD):T lymphocyte purging of PBSC transplantation material Graft versus host disease (GvHD) is induced by T lymphocytes that are present in donor allografts, though complete removal of such cells also results in failure of the graft and tumor relapse. Thus the presence of a limited number of T lymphocytes may be required for successful allogeneic transplant. In experiments carried out in support of the present invention, DACS beads were used to deplete T lymphocytes from apheresed PBSC preparations from G-CSF mobilized donors. FIG. 19 shows results of a study in which T lymphocytes were depleted from a mobilized PBSC preparation by adding to the preparation of mixture of anti-CD3, anti-CD4 and anti-CD8 mouse monoclonal antibodies, followed by goat anti-mouse-IgG DACS beads, and centrifugation through an OCS gradient having a density of 1.0605 gr/ml at 280 mOsm, pH 7.4, according to the methods described in Example 2. T lymphocytes were monitored by reaction with anti-CD2 monoclonal antibodies, in order to avoid possible artifacts associated with using antibodies that recognize the same epitopes on the differentiation antigens.

As shown in FIG. 19, using this DACS T lymphocyte depletion method, about a 97% reduction in T lymphocytes was achieved with only a 70% reduction in the yield of CD34$^+$ cells. Sixty percent of the CD34$^+$ cells were retained in the interface after DACS treatment. The results demonstrate that the combined cell enrichment and DACS method specifically reduces T lymphocyte content of allograft material by 97% with less than 40% loss of CD34$^+$ cells. Such a preparation is suitable for preventing GVHD in transplant material.

Natural Suppressor Cells

In vitro studies have shown that human bone marrow contains low density cells that block in vitro alloresponses in the mixed lymphocyte reactions (MLR). Based on the fact that this suppressive activity was HLA non-restricted, it was referred to in the literature as natural suppressor (NS) activity. A "PERCOLL" density gradient was adjusted to a density of 1.0605±0.0005 gr/ml to test for its ability to enrich cells with NS activity. Apheresed blood samples from lymphoma patients and from normal individuals that received G-CSF treatment were centrifuged on a discontinuous five layer gradient, and the interfaces and pellet were screened for their potential to suppress the mixed lymphocyte culture. FIG. 20 shows that cells with NS activity had a density equal or lighter than 1.0605 gr/ml. Consequently, more than 90% of the NS activity was present in the final cell preparation after centrifugation on a 1.0605 gr/ml gradient.

Natural Killer Cells

Natural Killer (NK) cells have been shown to kill autologous tumor cells. From a clinical perspective, it may be beneficial to have increased numbers of NK cells in the transplant to reduce tumor relapse. In experiments carried out in support of the present invention the density of the NK cells was determined on a discontinuous five-layer "PERCOLL" gradient. NK cells also showed a density equal to or lighter than 1.0605 gr/ml. Consequently, more than 90% of NK cells was present in the final cell preparation after centrifugation on a 1.0605 gr/ml gradient, as shown in FIG. 21.

5.3.C. Enrichment and Purging of Tumor Cells

It is established that tumor cells and tumor emboli spread directly to the bloodstream providing an alternative and desirable source of breast tumor cells for diagnostic purposes. In order to successfully utilize circulating bodily fluids for cancer diagnosis, the small number of circulating tumor cells must first be enriched, and highly sensitive and specific techniques must be employed for detection of tumor cells. This can be accomplished by application of the methods of the present invention to detection of metastatic tumor cells from such fluids.

In experiments carried out in support of the present invention, it has been shown that the methods of the present invention are effective to enrich breast tumor cell populations from cell sources or cell mixtures, based on density gradient centrifugation, and more specifically, by using the cell-trap centrifugation tube containing a precisely determined density of a density gradient solution as discussed above. In combination with tumor-specific antibodies and density adjusted cell sorting, the methods of the invention also facilitate purging of tumor cells from a bone marrow or peripheral blood stem cell graft.

Enrichment of Tumor Cells for Diagnosis

Breast tumor cells are used to exemplify the enrichment methods of the present invention. To enrich for such cells, a gradient should be adjusted to a density of 1.0490 to 1.0580±0.0005 gr/ml, depending upon the specific type of breast tumor cell, a physiologic osmolality of 270–290 mOsm/kg $H_2O$ and physiologic pH 6.8–7.8. In a specific embodiment by way of examples, breast tumor cells are directly loaded into a cell-trap centrifugation tube containing an appropriate cell separation medium, such as OCS-particle-based cell separation medium or "PERCOLL" solution filled to a level above the constriction.

In the specific examples described herein, successful enrichment of tumor cells was carried out on "PERCOLL" density gradient material which had been adjusted to the specific density of between 1.0490 to 1.0580±0.0002 gr/ml, depending upon the specific type of breast tumor cell, osmolality of 280 mOsm/kg $H_2O$ and pH 7.4. The density of the "PERCOLL" solution may be adjusted on a densitometer to precisely define its accuracy, as described in Section 5.1.B.

The cells enriched by the methods described in Example 3 may subsequently be examined for the presence of breast tumor cells. The resultant yield of isolated or enriched cells from the cell separation methods of the present invention may be used for diagnostic purposes, e.g. morphological, molecular, biochemical or immunophenotypic assays. For example, DNA may be prepared from the collected cells and subjected to polymerase chain reaction (PCR), as described under the tumor cell purging section below, or the collected cells may be assessed morphologically thereby avoiding the use of invasive and expensive surgical procedures heretofore relied upon for such a determination.

Various breast tumor antigens and breast tumor markers are known to those of skill in the art or are commercially available including but not limited to cathepsin D (Westley et al., 1980), EGF-R (Osborne et al., 1980), estrogen receptor (Gorski et al., 1966), Ki-67 (Gerdes et al., 1983), progesterone receptor (Horowitz et al., 1983), and TGF-α, associated with breast cancer. Antibodies directed to these antigens or markers may be used to assess the tumor type of collected cells.

A major advantage of the methods described herein is that a large volume of complete blood may be directly placed on the density gradient. Peripheral blood may be collected in anti-coagulant-containing tubes or by apheresis or leukopheresis. Complete blood does not need to be processed or diluted prior to centrifugation. However, since the methods enrich breast tumor cells based on their specific buoyant density, it is important that the cells are subject to separation within a relatively short time after their collection from an in vivo source because the density of the cells changes according to their culture or storage conditions. Therefore, in order to obtain optimal enrichment of breast tumor cells from blood, it is preferred that the blood samples are used within 48 hours after their collection. Most preferably, blood samples should be subjected to density gradient centrifugation within several hours of collection.

The densities of four breast tumor cell types, derived from tumor cell lines, were determined using "PERCOLL" discontinuous density gradient system (FIGS. 22A–22D). The cells were collected from each of the interfaces and counted in a hemocytometer. The results showed that 30 to 60% of the tumor cells have a density equal to or higher than 1.0580 g/ml (FIGS. 23A–23D). This implies that the fraction containing tumor cells was between 10 and 80% pure. Of the cells collected in a specific density of 1.0580, approximately 75 to 85% of the total cells were tumor cells, while approximately 10% of the total cell volume was a contaminant. This implies that the detection limit of the assay is improved approximately 10 times from $1/10^6$ to $1/10^5$.

Purging of Tumor Cells

Tumor cell purging is conveniently carried out using the tumor cell enrichment methods discussed above, or more preferably, the DACS augmented cell separation methods described above. By way of example, when radioactively labeled breast tumor cells were mixed with a peripheral blood buffy coat, up to 80% of were retained by centrifuging the mixture on a gradient having a specific density of 1.0580 gr/ml and an osmolality of 280 mOsm/kg $H_2O$. In addition, only a small fraction (<10% of initial cell number) of non-tumor cells were found in the collected tumor fraction.

The density ranges shown in FIGS. 22A–22D and 23A–23D, obtained from using cultured breast tumor cells, may be used as guidelines for breast tumor cells from in vivo sources. It will be apparent to those of skill in the art that slight variations in the densities of various breast tumor cells from in vivo sources may necessitate refinement of the exact density necessary to achieve optimum enrichment. Methods for determining specific densities with an accuracy of ±0.0002 gr/ml are disclosed herein.

The foregoing method may also be used in conjunction with the DACS procedure described herein. For example, complete blood can be directly incubated with carrier particle-coated-anti-CD45 antibodies which react with most leukocytes. Since breast tumor cells do not react with anti-CD45 to any significant degree, the vast majority of the non-red blood cells, leukocytes, and other cells are rendered heavier than the density material and pellet during centrifugation, while the breast tumor cells remain in the upper compartment. A variety of other cell type-specific binding agents may be used to target specific cell types in the blood, as discussed in the previous sections.

Alternatively, according to a preferred purging procedure, the positive selection DACS procedure may be used to cause tumor cells to be heavier than their normal densities, so that they are pelleted during centrifugation. Cell type-specific binding agents useful in the positive selection procedure include, but are not limited to antibodies to breast tumor antigens and antibodies to breast tumor markers, e.g. HER2/Neu, CA 15-3 (Kufe et al., 1984), CA 549 (Bray et al., 1987), cathepsin D (Westley et al., 1980), EGF-R (Osborne et al., 1980), estrogen receptor (Gorski et al., 1966), Ki-67 (Gerdes et al., 1983), progesterone receptor (Horowitz et al., 1983), and TGF-α, associated with breast cancer. Many of these antibodies are commercially available.

The cells enriched by the methods described herein can subsequently be examined for the presence of breast tumor cells. The resultant yield of isolated or enriched cells from the cell separation methods of the present invention may be used for diagnostic purposes, e.g. morphological, molecular, biochemical or immunophenotypic assays. For example, DNA may be prepared from the collected cells and subjected to polymerase chain reaction (PCR) or the collected cells may be assessed morphologically thereby avoiding the use of invasive and expensive surgical procedures heretofore relied upon for such a determination. Alternatively, tumor cells can be identified by the presence of tumor cell markers known to those of skill in the art, including but not limited to cathepsin D (Westley et al., 1980), EGF-R (Osborne et al., 1980), estrogen receptor (Gorski et al., 1966), Ki-67 (Gerdes et al., 1983), progesterone receptor (Horowitz et al., 1983), and TGF-α, associated with breast cancer. Antibodies directed to these antigens or markers may be used to assess the tumor type of collected cells.

Tumor Purging of Peripheral Blood Samples

The presence of tumor cells in stem cell grafts and the inability to specifically deplete tumor cells from the bone marrow of non-Hodgkins lymphoma patients may be an important indicator in predicting disease relapse after autologous transplantation. Cell separation methods in accordance with the present invention can be applied to remove tumor cells from peripheral blood products prior to re-introduction of such products into the patient.

In studies carried out in support of the present invention, the human B-cell lymphoma cell line SU-DHL4 was used to model tumor cell contamination of peripheral blood. This cell line contains a reciprocal translocation between the long arms of human chromosomes 14 and 18, resulting in a juxtaposition of the bcl-2 proto-oncogene to the joining region of the immunoglobulin (Ig) heavy chain gene. This translocation, which leads to elevated levels of the bcl-2 gene product, is found in 85% of follicular small cleaved cell lymphomas and 25% of diffuse large cell lymphomas. The translocation breakpoint in the bcl-2 gene is located in either the major breakpoint region (MBR) spanning approximately 150 bp in the 3' untranslated region (UTR) of the bcl-2 gene or the 500 bp minor cluster region (MCR) located approximately 20 kb downstream of the bcl-2 gene. Using translocation-specific primer pairs and quantitative PCR by limiting dilution analysis techniques known in the art, depletion of SU-DHL4 cells in DACS purging experiments was monitored.

Likewise, human SK-BR3 adenocarcinoma cell line is used to model breast cancer cell infiltration of peripheral blood. This cell line reacts with the mouse anti-human Her2/Neu monoclonal antibody. Prior to being spiked into normal buffy coats, the SK-BR3 cells were pre-loaded with calcein AM, a fluorogenic substrate so that they could be enumerated by FACS analysis. Details of the experimental methods used in carrying out tumor purging experiments are provided in Example 5.

A PCR assay, detailed in Example 5, was used to monitor tumor cell levels in the blood cell mixtures. Initially, mixtures of genomic DNA from SU-DHL4 and a (14;18) translocation-negative human cell line (K562) were used as starting templates to assess the level of sensitivity of the PCR assay. Agarose gel electrophoresis was used to separate PCR products from either one round or from two-rounds of amplification, as shown in. PCR products specifically derived from SU-DHL4 DNA were identified on the gel. The results of these preliminary tests showed that a nested PCR assay can detect approximately 1 SU-DHL4 cell per 150,000 cells.

In addition, genomic DNA was prepared from frozen aliquots of apheresed blood of 24 NHL patients who received chemotherapy and G-CSF, according to standard methods known in the art. Nested PCR products using primer-pairs specific for the major breakpoint region (MBR) translocation were found in 4 patients, demonstrating that this assay can detect cells carrying the (14;18) translocation from authentic clinical samples.

Further experiments were carried out to validate the use of PCR analysis under conditions of limiting dilution for quantitation of tumor cell frequency in a sample. Replicate PCR reactions were performed using known amounts of input SU-DHL4 genomic DNA. Nested PCR primer-pairs for t (14;18) (a target sequence present once per SU-DHL4 cell) and p53 (a target sequence present twice per SU-DHL4 cell) were used. The observed frequency of positive PCR reactions demonstrated that experimental frequencies are similar to frequencies expected based on Poisson statistics. Thus, PCR using limiting dilution analysis was demonstrated to provide an accurate, quantitative method for monitoring tumor cells.

To model tumor cell contamination of PBPC, samples of apheresed blood from G-CSF mobilized patients were seeded with a known number of SU-DHL4 cells. This spiked material was used to assess tumor cell removal by DACS. This method involves incubation of the blood with mouse monoclonal antibodies specific to surface antigens expressed on the target cell (CD9, CD10, CD19, CD20). This step was then followed by incubation with goat anti-mouse Ig coated high-density microspheres (DACS beads). The sub-population of cells bound to these microparticles was then separated from unbound cells by centrifugation through an OCS suspension supplemented with 0.5% PVP at a specific density of 1.0605 gr/ml and sterilized by gamma irradiation. Cells were recovered from the interface (IF) and from the pellet (PT) after gradient centrifugation and were quantitated by gel electrophoresis, as detailed in Example 5 and illustrated in FIG. 24. The results of a representative purging experiment are shown in FIG. 25 and FIG. 26.

FIG. 25 shows the number of spiked SU-DHL4 cells in the; A) unfractionated sample (determined by visual count), B) unfractionated sample, C) interface without DACS, D) interface after using GAM-IgG DACS beads, and E) interface after using GAM-IgG DACS beads and a cocktail of anti-B cell mAbs. The number of SU-DHL4 cells in B, C, D and E was determined by quantitative-PCR.

FIG. 26 represents the recovery of CD34$^+$ cells in the interface (IF) and pellet (PT) of C, D and E. Tumor cell depletion was quantitated by PCR limiting dilution analysis for samples B–E, as illustrated. The recovery of CD34$^+$ hematopoietic stem cells was monitored by three-color flow cytometry. Recovery of total cells and stem cells are shown relative to the recovery of cells from the interface. A single purging cycle using an antibody cocktail resulted in specific 2–3 log depletion of SU-DHL4 cells. The recovery of CD34$^+$ cells after DACS was greater than 70% and comparable to the number of CD34$^+$ cells recovered from the interface in the absence of DACS. Peripheral blood mononuclear cells are reduced by 70–80% by the density centrifugation with or without DACS.

In another model for tumor cell contamination, SK-BR3 cells were seeded into normal buffy coats at a frequency of 2%. The calcein AM labeled cells tumor cells were removed from the cell suspension by centrifugation on an OCS density suspension having a specific density of 1.0605 gr/ml with DACS using anti-human Her-2/Neu Mabs. The depletion vas determined by FACS analysis, as illustrated in FIG. 27. The calcein AM labeled cells were gated and their percentage determined using the LYSYS II program. The different figures represent; A) Staining of SK-BR3 cells with anti Her2/Neu (black) versus unstained cell control, B) Staining of SK-BR3 cells with calcein AM, C) Isotype control of cells, D) Calcein AM spiked SK-BR3 cells (1.8%) in buffycoat, E) Cell fractionation on 1.0605 gr/ml OCS, F) Same as E but in the presence of goat anti-mouse coated DACS beads and G) Depletion of SK-BR3 cells by DACS using an anti-human Her2/Neu mAb. Whereas the SK-BR3 cells were not depleted from the buffy coat after processing on OCS suspension in the presence (FIG. 27F) or absence (FIG. 27E) of DACS beads, they were almost completely removed from the cell mixture when using DACS beads in combination with the breast cancer specific anti-Her2/Neu mAb. The data in FIG. 27G demonstrate DACS treatment reduces tumor cell contamination by 1 to 2 logs (10–100-fold) when the FACS percentage is back calculated to the initial tumor cell number spiked in the sample.

In summary, the foregoing exemplary model experiments using a human B-cell lymphoma cells and quantitative PCR demonstrate that a 2–3 log reduction in tumor cells can be achieved in one round of DACS while retaining the majority of CD34$^+$ hematopoietic stem cells. Using a human adenocarcinoma cell line SK-BR3 and FACS analysis, a 1–2 log reduction in tumor cells was achieved.

More generally, it is the discovery of the present invention that this method can be used to purge blood or therapeutic enriched cell populations of unwanted tumor cells.

5.3.D. Enrichment of Dendritic Cells and Cytotoxic T Lymphocytes

Dendritic cells (antigen presenting cells) are cells that are derived from blood fractions. These cells act in vivo to present antigen to T lymphocytes to induce a primary cytotoxic T lymphocyte (CTL) response. These cells have clinical utility for use in inducing or enhancing cellular immune responses.

According to another aspect of the present invention, dendritic cells and cytotoxic lymphocytes are isolated using defined density gradients, in a three step process. This process includes centrifugation through three different density gradient solutions, as detailed in Example 6, below. In accordance with the present invention OCS density gradient material having densities of 1.0720, 1.0610, and 1.0565 gr/ml, each at pH 7.4 and an osmolality of 280 mOsm/kg H$_2$O are used in the three described steps, which are conveniently, but not necessarily carried out in a cell-trap tube. Practitioners will recognize that equivalent densities of other media can be used as well. For example, step one can be carried out in Lymphoprep (Nycomed Laboratories, Oslo, Norway) or in Ficoll equivalent PERCOLL (density 1.0770, 310 mOsm/kg H$_2$O, pH 7.4); step two can be carried out in a PERCOLL solution (density 1.0650, pH 7.4, 300 mOsm/kg H$_2$O; and step three can be carried out in a PERCOLL solution having a density of 1.0800 gr/ml, pH 7.4, 540 mOsm/kg H$_2$O, or in a PERCOLL solution having a density of 1.0550 gr/ml, 290 mOsm/kg H$_2$O, pH 7.4). However, the foregoing densities determined using OCS-particle based cell separation and the enrichment methods of the present invention, are advantageous in that they are carried out at physiological osmolalities, rather than under the hyperosmotic conditions previously reported.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

EXAMPLES

Example 1

Isolation of Nucleated Red Blood Cells from Material Blood

A. Preparation of Density Gradients

"PERCOLL" solution was purchased from Pharmacia Biotech (Uppsala, Sweden) and stored at 4° C. according to the recommendation of the vendor. A stock solution was prepared by mixing 12 parts of "PERCOLL" with 1 part of 10×calcium and magnesium-free phosphate buffered saline (PBS). The pH of the solution was adjusted to 7.4 and the osmolality to 280±10 mOsm/Kg $H_2O$. For use in separating fetal nucleated red blood cells in a blood sample, the stock solution was further diluted with calcium and magnesium-free PBS to a density of 1.0720±0.0005 gr/ml and used at room temperature. It was important to adjust the density of the gradient to an accuracy within ±0.0005 gr/ml, preferably within 0.0002 gr/ml of 1.0720 gr/ml in order to ensure reproducibility and accuracy of cell separation. This was done by a high precision digital density meter such as DMA 48 (Anton PAAR USA, Ashland, Va.). All procedures were performed under sterile conditions and at room temperature.

B. Collection and Processing of Blood Samples

Peripheral blood was collected from pregnant females in anti-coagulant-containing tubes. The collection was performed before week 20 of pregnancy because the number of fetal cells circulating in maternal blood generally began to decline after week 17 of pregnancy. An optimal collection time is week 13. After collection, the blood samples were processed within 48 hours.

C.1. Density Gradient Centrifugation of Peripheral Blood

Complete blood samples were layered on a "PERCOLL" cell separation medium previously adjusted to a density of 1.0720±0.0002 gr/ml, an osmolality of 280 mOsm/Kg $H_2O$, and a pH of 7.4 in a 50 ml conical cell-trap tube. The tube contained a constriction in a location so that approximately 15 ml of "PERCOLL" was in the lower compartment and 5 ml of "PERCOLL" was above the constriction. Generally, 20 ml of blood samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet and associated liquid in the region below the constriction remained therein when the tube was inverted. After centrifugation at 650×g for 10 minutes at room temperature, the fluid on top of the pellet was removed with a pipette, and the cells in the pellet resuspended in PBS. Since this low speed centrifugation step was primarily used to concentrate the cells of interest into a pellet, while removing cell debris and platelets in the upper region, a cell-trap could also be used to facilitate this step. In this alternative embodiment, a modified 50 ml cell-trap tube was used in which the constriction was placed near the bottom of the tube so that a small volume of about 0.5 ml was below it. This design would protect the pellet and reduce cell loss during removal of the fluid above the pellet after centrifugation. This specific feature would also allow the method of the invention to be used in an automated fashion without the need for a subsequent cell sorting step, which was performed to reduce contaminating cells, particularly platelets.

The cell separation method described above was compared with conventional methods, and the following procedure was also carried out as a control. This procedure was similar to previously published methods known in the art (Bianchi et al., 1990, *Proc. Natl. Acad. Sci. U.S.A.* 47:3279).

The blood sample was collected as described above and diluted 1:4 in PBS. The diluted blood was layered on "FICOLL-HYPAQUE" (Pharmacia) in 4 different 15 ml tubes. The density of the stock "FICOLL" solution was at 1.077±0.001 gr/ml and the osmolality at 320 mOsm/kg$H_2O$ as published by Pharmacia. The tubes were centrifuged at 850×g for 20 minutes at room temperature. The cells at the interface above the "FICOLL" were collected with a pipette and transferred to two 15 ml tubes. The tubes were filled to the top with PBS and spun at 650×g for 10 minutes at room temperature. The fluid on top of the pellet was aspirated with a pipette, and the pellet resuspended in PBS. In addition, experiments were also performed using cell-trap tubes with "FICOLL" solution in an effort to increase cell yield.

C.2 Affinity Separation by a Magnetic Field

The fetal nucleated red blood cells resuspended in PBS after density gradient centrifugation described above were further enriched through removal of $CD45^+$ leukocytes by incubating the cells with an anti-CD45 monoclonal antibody (clone ALB-12) (Biodesign International, Kennebunk, Me.) for 30 minutes at 4° C. The unbound antibodies were removed by washing the cells in PBS. A goat-anti-mouse antibody conjugated to magnetic particles (Immunocon) was added to the cells for 30 minutes at 4° C. The cells were washed in PBS and exposed to a magnetic field which attracted the magnetic particle-coated $CD45^+$ leukocytes, while the fetal nucleated erythroid and trophoblast cells remained in solution. The fetal cells were collected with a pipette and washed once in PBS. The cells were then tested by antibody staining and flow cytometric analysis to determine the number of nucleated red blood cells.

D.1 Density Adjusted Cell Sorting

Complete blood collected from pregnant females was incubated with 1.4µ aminopropyl glass beads (Bangs Laboratories Inc., Carmel, Ind.) that were glutaraldehyde coated with an anti-CD45 antibody (ALB-12) for 45 minutes at room temperature. The entire blood cell mixture was layered on "PERCOLL" (1.0720±0.0002 gr/ml, 280 mOsm/Kg $H_2O$, pH 7.4) in a 50 ml cell-trap tube. The tube contained about 15 ml of "PERCOLL" below the constriction and about 5 ml above it. It was critical to completely fill the volume under the constriction with "PERCOLL" to prevent the formation of air bubbles. The tube was centrifuged at 850×g for 30 minutes at room temperature. The leukocyte-depleted cell population was collected from the interface above the "PERCOLL" by pouring off the entire upper region of the tube into a 50 ml tube. The cells were spun at 650×g for 10 minutes at room temperature, and the fluid on top of the pellet removed with a pipette. The cells in the pellet were resuspended in PBS.

Alternatively, the second centrifugation step can be carried out in a modified cell-trap tube as described in Section 5.2 supra. Additionally, a second density adjusted cell sorting could also be performed using antibodies such as anti-CD41 to specifically remove platelets.

D.2. Antibody Staining and Flow Cytometric Analysis

The leukocyte-depleted cell population in PBS were treated with the DNA dye LDS 751 (Exciton, Inc., Dayton, Ohio) and erythroid lineage specific FITC-conjugated monoclonal antibodies such as anti-glycophorin A and anti-CD71 (Becton Dickinson, Inc., San Jose, Calif.). The LDS 751 dye distinguished between nucleated and a nucleated cell. One million cells were incubated with 10 µl antibodies for 30 minutes at 4° C. in the presence of 5% rabbit serum and LDS 751. The cells were washed twice with PBS and fixed in 1% paraformaldehyde. The antibody-bound cells were analyzed by flow cytometry for which statistical analysis was performed on $10^4$ flow events using a FACSScan system equipped with a LYSYS II program.

Example 2

Enrichment of $CD34^+$ Cells from Cell Mixtures

A. Preparation of Density Gradients

A.1. Percoll Density Gradient

"PERCOLL" solution was purchased from Pharmacia Biotech (Uppsala, Sweden) and stored at 4° C. according to the recommendation of the vendor. A stock solution was prepared by mixing 12 parts of "PERCOLL" with 1 part of 10×calcium and magnesium-free phosphate buffered saline (PBS). The pH of the solution was adjusted to 7.4 and the osmolality to 280 mOsm/Kg $H_2O$. For use in separating $CD34^+$ cells in a cell mixture, the stock solution was further diluted with calcium and magnesium-free PBS to a density of 1.0605±0.0005 gr/ml and used at room temperature. It was crucial to adjust the density of the gradient to an accuracy of within ±0.0005 gr/ml of 1.0605 gr/ml in order to ensure reproducibility and accuracy of cell separation. This was done by a high precision digital density meter such as DMA 48 (Anton PAAR USA, Ashland, Va.). All procedures were performed under sterile conditions and at room temperature.

A.2. Organosilanized Colloidal Silica (OCS) Density Gradient

An OCS particle suspension is an organosilanized colloidal silica particulate suspension prepared as described by Dorn (U.S. Pat. No. 4,927,749). OCS particles ranging in size from 3–22 nm, and particularly from 13–18 nm, form a stable suspension that acts as a density gradient medium for separating heterogeneous mixtures of cells on the basis of buoyant density. Unless otherwise indicated, the OCS particle suspension was prepared in a physiological saline solution to have a density of 1.0605 gr/ml at an osmolality of 280 mOsm/kg $H_2O$, as defined for the enrichment of $CD34^+$ cells from PBSC samples. The suspension was produced under GMP conditions and is sterilized by gamma irradiation in the presence of at least 0.05% polyvinylpyrrolidone (PVP-10; Sigma Chemical Co., St. Louis, Mo.). The PVP was added as a dry powder to a suspension of OCS particles preadjusted to the approximate final desired specific density. PVP concentrations of at least 0.05% and as high as 10% are preferred for use in the methods, apparatus and kit of the invention. Inclusion of PVP, and more generally, a polylactam exemplified by PVP, provides improved functional yields of rare blood cells.

The OCS suspension was preferably contained in an embodiment of the above-described cell-trap centrifugation tube. The particular shape of this tube allows the collection of cells from the interface after centrifugation by simple decantation rather than by pipetting.

B. Collection of Blood and Bone Marrow

Patients were hydrated and treated with cyclophosphamide (4 gm/m²) administered by intravenous (IV) infusion over two hours through a central venous catheter. Twenty-four hours after the completion of the cyclophosphamide infusion, patients were treated with G-CSF (Neupogen, Amgen, Thousand Oaks, Calif.) administered by subcutaneous (SC) injection at a dose of approximately 10 µg/kg/d. Apheresis was initiated upon recovery of the white blood cell count (WBC) to equal or more than $1 \times 10^9$/L. Apheresis was performed using a Cobe Spectra Cell Separator (Lakewood, Colo.) at a rate of 80 ml/mln for 200 min (total volume of 16 L). Peripheral blood buffy coats from healthy donors prepared by conventional methods were obtained from Stanford University Hospital Blood Bank, Palo Alto, Calif.

C. Density Gradient Centrifugation of Blood and Bone Marrow Buffy Coats

Apheresed peripheral blood was applied directly onto the density gradient. However, unless otherwise indicated, complete blood and bone marrow aspirates were processed to a buffy coat (removal of red cells), according to standard methods, before they were applied onto the density gradient.

Apheresed blood samples were layered on a "PERCOLL" gradient previously adjusted to a density of 1.0605±0.0005 gr/ml, an osmolality of 280 mOsm/Kg $H_2O$, and a pH of 7.4 in a 50 ml conical cell-trap tube or a commercially available tube. The cell-trap tube contained a constriction in a location so that approximately 15 ml of "PERCOLL" was in the lower compartment and 5 ml of "PERCOLL" was above the constriction. It was critical to completely fill the volume under the constriction with "PERCOLL" to prevent the formation of air bubbles. Generally, 20 ml of apheresed blood samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the region below the constriction were prevented from pouring off when the tube was inverted.

In order to compare the cell separation method described in the preceding paragraph with conventional methods of separation, the test samples were also was layered on "FICOLL-HYPAQUE" (Pharmacia). The density of the stock "FICOLL" solution was at 1.077±0.001 gr/ml and the osmolality at 320 mOsm/kg $H_2O$ as published by the vendor.

Bone marrow aspirate (complete cell fraction) was layered slowly on an OCS suspension prepared as described above to a density of 1.0685 gr/ml at an osmolality of 280 mOsm/kg$H_2O$. A maximum of $2 \times 10^9$ cells was layered and processed per centrifuge tube. The tube was centrifuged for 30 minutes at 850×g, at room temperature. Cells from the interface and pellet were collected separately from a cell-trap tube, in accordance with the present invention. Cell fractions were characterized by FACS analysis using FITC- and PE-conjugated anti-CD34 (anti-HPCA-2), anti-CD45 (anti-HLe-1), anti-CD3 (Leu-4) and IgG1 antibodies, obtained from Becton Dickinson, Inc. (San Jose, Calif.). For analysis, cells were labeled with the nuclear dye LDS 751 (Exciton, Inc., Dayton, Ohio). Statistical analysis was performed on $10^4$ flow events using a FACSCAN system equipped with a LYSYS II program (Becton Dickinson, Inc. (San Jose, Calif.).

D. Density Adjusted Cell Sorting

D.1. Anti-CD45-coated Beads

Apheresed blood product was incubated with 1.4µ aminopropyl glass beads (Bangs Laboratories Inc., Carmel, Ind.) that were glutaraldehyde coated with an anti-CD45 antibody (clone ALB-12, Biodesign International, Kennebunk, Me.) for 45 minutes at room temperature. The entire blood cell mixture was layered on OCS+0.5% PVP (1.0605±0.0005 gr/ml, 280 mOsm/Kg $H_2O$, pH 7.4) in a 50 ml tube.

D.2. Goat Anti-Mouse IgG (GAM-IgG)-coated Beads

Cells from the PBSC sample were counted by trypan blue exclusion, washed and resuspended in PBS supplemented with 0.1% bovine serum albumen (BSA) at a concentration of $10^7$ cells/ml. Anti-CD3, CD4 and CD8 mAbs were added to give a final concentration of 3–10 µg/ml. The cells were incubated for 30 minutes on ice and then centrifuged. The cell pellet was resuspended in 0.1% BSA in PBS at a cell concentration of $10^7$ cells/ml. Goat anti-mouse IgG (GAM-IgG) coated DACS beads were counted and added to the cells to give bead:cell ratios of between 4:1 and 8:1. The beads and calls were incubated for 15 minutes. During the incubation the cell:bead mixture was gently resuspended every 5 minutes. The cell-bead mixture was then layered onto OCS density gradient suspension and centrifuged at room temperature at 850×g for 30 minutes. The cells at the interface were harvested by decanting the centrifugation tube, counted and prepared for FACS analysis. To examine non-specific depletion, a similar procedure was used but the incubation with the monoclonal antibodies was omitted.

Experiments to examine the efficacy of DACS for T lymphocyte and anti-CD3, CD4 and CD8 mAbs. The yield of T lymphocytes was monitored using an anti-CD2 mAb in order to avoid artifacts associated with mAbs recognizing the same epitopes on the differentiation antigens.

E. Conjugation of Cell Attachment Molecules to Carrier Particles

E.1. Monoclonal Antibodies

Phycoerythrin-conjugated (PE-CD34) anti-CD34 monoclonal antibodies (hematopoietic progenitor cell marker) and fluorescein isothiocyanate-conjugated (FITC-CD45) anti-CD45 monoclonal antibodies (pan-leukocyte marker) were obtained from Becton Dickinson, Inc. (San Jose, Calif.). Unconjugated antibodies directed to CD45, CD16 (granulocytes, monocytes), CD3 (T lymphocytes), CD14 (monocytes) were prepared in the laboratory, according to methods well known in the art.

The anti-CD3 (clone Leu4), CD4 and CD8 mAbs were obtained from Dr. E. Engleman of Stanford University Hospital Blood Bank. In addition, FITC-CD2, PE-CD34 and FITC-CD45 were purchased from the same vendor.

Antibodies were conjugated to either goat anti-mouse coated magnetic beads or to goat anti-mouse coated aminopropyl glass beads by overnight incubation at room temperature. Alternatively, the antibodies could be bound directly to these beads without the goat anti-mouse bridge or could be bound via an avidin-biotin coupling reaction. In addition the antibodies could be cleaved into Fab2 fragments in order to reduce non-specific binding of cells to the beads via their Fc portion.

E.2. Goat Anti-mouse IgG (GAM-IgG)

Mouse IgG1 conjugated with either FITC ar PE were purchased from Becton Dickinson (San Jose, Calif.) and used as isotype control.

Several different procedures were used to prepare DACS beads coated with goat anti-mouse IgG (GAM-IgG) (Biodesign International). The goal was to maximize specific depletion and minimize non-specific depletion during DACS. DACS beads were covalently coated either with GAM-IgG or F(ab)$_2$ GAM-IgG (East Coast Biologicals) in a random orientation or GAM-IgG in a specific orientation to maximize the availability of the Ig binding sites to attach to antigen. In addition, some preparations of beads were coated with polyethylene glycol (PEG) (Shearwater) to reduce the non-specific affinity of the beads for protein or cells. The different chemistries are outlined below.

Random GAM-IgG or F(ab)$_2$ GAM-IgG

Silica beads were coated with aminopropyltriethoxysilane (Sigma) which has —NH$_2$ groups available to be conjugated to the —CHO of glutaraldehyde (Sigma). According to the chemistry employed, glutaraldehyde then forms a bridge and binds to the —NH$_2$ group on lysines throughout the GAM-IgG or F(ab)$_2$ GAM-IgG molecules, when both antibody and glutaraldehyde were added to the preparation. The orientation of the protein molecule relative to the bead was considered to be random, on the grounds that any lysine with an —NH$_2$ side-chain will potentially conjugate to the —CHO of the glutaraldehyde. This gives an ATES-GLUT-IgG chain with the IgG or IgG-F(ab)$_2$ in a random orientation.

GAM-IgG in a Specific Orientation

Silica beads were coated with aminopropyltriethoxysilane having —NH$_2$ groups available to be conjugated to the —CHO group of the carbohydrate on the glycosylated region of the Fc portion of the GAM-IgG molecule. The GAM-IgG molecule is only glycosylated on the Fc portion so that linking GAM-IgG to the bead surface through this region will have the effect of orienting the IgG molecule with the Fc portion next to the bead surface and the IgG binding sites away from the surface. This treatment theoretically increases the number of binding sites available to bind antigen and decreases the availability of the FC portion to bind Fc receptors. This gives an ATES-CHO-IgG chain with the IgG in a specific orientation.

PEG-aldehyde Random GAM-IgG

Silica beads were coated with aminopropyltriethoxysilane which has —NH$_2$ groups available to be conjugated to one —CHO group of an aldehyde-PEG-aldehyde molecule where PEG is sandwiched between two aldehyde residues. GAM-IgG then bound to the other —CHO residue to give an ATES-CHO-PEG-CHO-IGg chain with the IgG in a random orientation.

F. Antibody Staining and Flow Cytometric Analysis

Cells were washed one time with PBS, then incubated with 10 µL of monoclonal antibody/$10^6$ cells, 5% rabbit serum and the DNA dye LDS 751 (0.025%; Exciton Inc., Dayton Ohio.) for 30 min. on ice. Rabbit serum was used to reduce non-specific binding to the cells. The cells were washed twice with PBS and subsequently fixed with 1% paraformaldehyde. Statistical analysis was performed on $10^4$ flow events using a FACSScan flow cytometry system equipped with a LYSYS II program (Becton Dickinson, San Jose, Calif.).

G. Colony Forming (CFU) Assay/Functional Determination of Committed CD34$^+$ Cells The functional characteristics of the CD34$^+$ cells in a cell sample was determined by the colony formation assay (CFU). This assay allowed the quantification of the number of committed hematopoietic progenitor cells in the cell solution. $10^5$ cells were mixed in 2 mL semi-solid methyl cellulose containing different colony stimulating factors and erythropoietin (Terry Fox Laboratories, Vancouver). The entire mixture was incubated for 14 days at 37° C. The number of erythroid (CFU-E, BFU-E), granulocyte/macrophage (CFU-GM) and mixed (CFU-GEMM) colonies were counted under an inverted microscope (40×).

H. Long Term Culture Initiating Cell (LTC-IC) Assay/Functional Determination of Uncommitted CD34$^+$ Cells The number of uncommitted hematopoietic progenitor cells in a cell mixture was determined by the long term culture initiating culture. The cells were seeded on an irradiated stroma feeder layer and a determination of CFU's was made in function of time. Hematopoietic stem cells were able to self-renew and gave rise to CFU's in this system for a period that exceeded 5 weeks. Long term bone marrow stromal cultures were initiated in 96 well plates ($10^6$ cells in 200 µl per well) in α-MEM medium supplemented with 12.5% horse serum, 12.5% fetal calf serum, 2 mM L-glutamine, 0.2 mM i-inositol, 20 µM folic acid, $10^{-4}$M 2-mercaptoethanol and were kept at 33° C. in a humidified atmosphere. At weekly intervals, half the medium was removed and replaced by an equal volume of fresh medium. After 2 weeks of culture, the confluent stroma layers were gamma irradiated (2000 rad) to kill endogenous hematopoietic cells. Unfractionated samples and cell preparations after separation were seeded onto the irradiated stroma layers in the same medium supplemented with $10^{-6}$M hydrocortisone. After five weeks of culture the adherent and non-adherent cells were collected and screened in the CFU assay as in Part G, above.

I. Natural Killer (NK) Cell Assay

K562 target cells were labeled with 100 µCi $^{51}$Cr for 1 hour at 37° C. and then washed four times and counted. The target cells were co-cultured for 4 hours in V-bottom 96 well multiwell plates with unfractionated apheresed blood and cells from the different fractions after cell separation. Effector and target cells were mixed at different ratios, 100:1, 50:1, 25:1 and 12:1. For example, the 100:1 ratio contained $5\times10^5$ effector cells and $5\times10^3$ target cells. After the incubation period, 100 µl of the supernatant was harvested and counted in a scintillation counter. Maximal and spontaneous $^{51}$Cr release was measured counting either 50 µl of the stock target solution and supernatant from the effectors by themselves, respectively. The percent cytotoxicity was determined according to formula:

$$\text{Percent Cytotoxicity} = \frac{\text{cpm experiment} - \text{cpm spontaneous release}}{\text{cpm maximal release} - \text{cpm spontaneous release}}$$

J. Mixed Lymphocyte Culture and Natural Suppressor Cell Activity

Cells from two different buffy coats were mixed in a flat bottom 96 well multiwell plate at $10^5$ cells of each. One of the buffy coats received 3000 rad and was referred to as the "stimulators". The other buffy coat was used untreated and referred to as "responders." Unfractionated apheresed peripheral blood products (APBL) or cells from the different density fractions were added to these co-cultures at $10^5$ cells per well. These cells were referred to as "suppressors" and received 1500 rad prior to being added to the MLR. The cells were cultured for 5 days and then pulsed with [$^3$H]-thymidine (1 µCi/well). 18 hours later, the cells were harvested and the amount of thymidine incorporated determined in a scintillation counter. The percent suppression induced by the suppressor cells was determined by the formula:

$$\text{Percent Suppression} = \frac{\text{cpm control} - \text{cpm experiment}}{\text{cpm experiment}}$$

Example 3

Determination of Density of Breast Tumor Cell Density and Their Enrichment by Density Gradient Centrifugation Cells were incubated with $^3$H thymidine for 24 hours under standard culture conditions according to methods known in the art. The cells were mixed with buffy coat from peripheral blood.

A. Preparation of Density Gradients

"PERCOLL" solution was purchased from Pharmacia Biotech (Uppsala, Sweden) and stored at 4° C. according to the recommendation of the vendor. A stock solution was prepared by mixing 12 parts of "PERCOLL" with 1 part of 10×calcium and magnesium-free phosphate buffered saline (PBS). The pH of the solution was adjusted to 7.4 and the osmolality to 280 mOsm/KgH$_2$O. For use in enriching breast tumor cells obtained from in vitro cell lines in a cell mixture, the stock solution was further diluted with calcium and magnesium-free PBS into five different fractions with respective densities of 1.0490, 1.0520, 1.0550, 1.0580, and 1.0610 and used at room temperature. It was crucial to adjust the density of the gradient with an accuracy of ±0.0002 gr/ml point in order to ensure reproducibility and accuracy of cell separation. This was done by a high precision digital density meter such as DMA 48 (Anton PAAR U.S.A., Ashland, Va.). All procedures were performed under sterile conditions and at room temperature.

B. Density Gradient Centrifugation

Radioactively labeled breast cancer cells were mixed with a buffy coat from a healthy donor and centrifuged on the discontinuous gradient. Cell mixtures containing the breast tumor cells from cell lines 30 HTB, 126 HTB, 1500 CRL and 1504 CRL were layered on a "PERCOLL" gradients previously adjusted to densities in the range of 1.0490–1.0610,±0.0002 gr/ml, at osmolalities of 280 mOsm/KgH$_2$O, and a pH of 7.4 in a 50 ml conical cell-trap tube. The tube contained a constriction in a location so that approximately 15 ml of "PERCOLL" was in the lower compartment and 50 ml of "PERCOLL" was above the constriction. It was critical to completely fill the volume under the constriction with "PERCOLL" to prevent the formation of air bubbles. Generally, 20 ml of cell samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the compartment below the constriction were prevented from pouring off when the tube was inverted. After centrifugation at 650×g for 10 minutes at room temperature, the fluid on top of the pellet was removed with a pipette, and the cells in the pellet resuspended in PBS. Since this low speed centrifugation step was primarily used to concentrate the cells of interest into a pellet, while removing cell debris and platelets in the fluid, a cell-trap could also be used to facilitate this step. In this alternative embodiment, a modified 50 ml cell-trap tube was used in which the constriction was placed near the bottom of the tube so that a small volume of about 0.5 ml was below it. This design protects the pellet and reduces cell loss during removal of the fluid above the pellet after centrifugation. This specific feature would allow the method of the invention to be automated without the need for cell sorting.

Example 4

Preparation of Carrier Particles

A. Preparation of Beads

Silica beads (1.4 microns) obtained from Bangs Laboratories, Carmel, Ind. were washed with concentrated HCl for 2 hours at room temperature and vortexed intensely every 15 minutes to break up bead clumps. After washing, the beads were centrifuged at 850 g for 5 minutes. The HCl containing supernatant was decanted and the beads were washed with deionized H$_2$O with intensive vortexing to break up the clumps.

The beads were incubated at room temperature overnight in concentrated nitric acid with constant stirring using a magnetic stirrer. The beads were then centrifuged at 850 g for 5 minutes and washed 3 times with deionized water, using 50 ml of deionized H$_2$O at each step. The beads were vortexed intensely in between each wash to avoid bead clumping. To prevent microbacterial contamination, the beads were stored at 0–4 degrees centigrade in deionized H$_2$O until further use.

B. Silanization of the Beads

To silanize the beads, either 3-aminopropyltriethoxysilane, (3-iodopropyl) trimethoxysilane or [1-9trimethoxysilyl)-2(m-(or p) chloromethyl)phenyl] ethane were used. Forty mls of silane solution (a 10% solution in 95% ethanol/deionized H$_2$O) was added per 4 gr of beads. The bead mixture was rotated end over end for 1 hour at room temperature. The beads were centrifuged at 850 g for 5 minutes and the excess silane was washed off using 95% ethanol/deionized H$_2$O in a volume of 100 ml. The beads were vortexed intensely in between each wash step to avoid bead clumping. After the washing step, the beads can be dried and stored. Alternatively the beads can be stored in 95% ethanol/deionized H$_2$O in the cold which prevents clumping of the beads.

C. Antibody Coupling to the Aminopropyl Glass

The silanized beads were incubated overnight in 2.5% glutaraldehyde at room temperature. The next day, the beads were centrifuged at 850 g for 5 minutes and the free glutaraldehyde was washed off with deionized H$_2$O in a volume of 100 ml per 5 gr beads. The beads were vortexed intensely in between each wash step to avoid bead clumping.

The antibody was added to the aminopropyl beads in an excess, at least 3 mg/m$^2$ total bead surface and rotated end over end overnight at room temperature. The next day, the beads were centrifuged at 850 g for 5 minutes and the free protein was washed off with 100 ml of deionized H$_2$O. The beads were vortexed intensely in between each wash step to avoid bead clumping. The beads were stored in deionized H$_2$O containing 0.1 sodium azide in the cold. The final bead suspension should contain 70–90% single beads and 10–30% predominantly duplet and triplet beads.

The binding efficiency of the antibody conjugated beads (in terms of the percent of beads that are coated) can be determined using flow cytometric analysis and a fluoresceinated antibody directed to the coupled antibody. Alternatively, the antibody may be added to the silanized beads directly without the glutaraldehyde linking.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

Example 5

Purging Tumor Cells from Peripheral Blood

The human B-cell lymphoma cell line SU-DHL4 (Stanford University Blook Bank, Stanford, Calif.) was used as a standard experimental model to model tumor cell contamination of peripheral blood. This cell line contains a reciprocal translocation between the long arms of human chromosomes 14 and 18, resulting in a juxtaposition of the bcl-2 proto-oncogene to the joining region of the immunoglobulin (Ig) heavy chain gene. This translocation, which leads to elevated levels of the bcl-2 gene product, is found in 85% of follicular small cleaved cell lymphomas and 25% of diffuse large cell lymphomas. The translocation breakpoint in the bcl-2 gene is located in either the major breakpoint region (MBR) spanning approximately 150 bp in the 3' untranslated region (UTR) of the bcl-2 gene or the 500 bp minor cluster region (MCR) located approximately 20 kb downstream of the bcl-2 gene. Using translocation-specific primer pairs and quantitative PCR by limiting dilution analysis, depletion of SU-DHL4 cells in DACS purging experiments can be monitored.

The human SK-BR3 adenocarcinoma cell line (American Type Culture Collection (ATTC), Rockville, Md.) was used as a standard experimental model to model breast cancer cell infiltration of peripheral blood. These cells react with the mouse anti-human Her2/Neu monoclonal antibody, indicating they possess a Her2/Neu antigen. Prior to being spiked into normal buffy coats, the SK-BR3 cells were pre-loaded with calcein AM, a fluorogenic substrate so that they can be enumerated by FACS analysis. @@@Alternatively or in addition breast tumor cells contain estrogen receptors and react with antibodies to such receptors and other receptor binding molecules, such as estrogen and estrogen agonists. For purposes of the present invention, such cells can be captured, as in the tumor cell purging methods described herein, by any molecule that binds with sufficient affinity to such a tumor cell antigen, including, but not limited to antibodies, estrogen- or estrogen agonists. In this context, a sufficient affinity of binding is an affinity approximately equal to or within 2 log binding affinity units of the mouse anti-human Her2/Neu monoclonal antibody (HB 8694, 520C9; ATCC, Rockville, Md.)

PCR Analysis

High molecular weight genomic DNA was prepared using the QIAamp Blood Kit (Qiagen, Chatsworth, Calif.) and quantitated by optical density at 260 nm. PCR reactions were done using a Perkin-Elmer model 9600 thermocycler for 35 cycles. Each amplification cycle consisted of 94° C. (15"), 55° C. (60"), and 72° C. (15"), with a 72° C. (6 min.) extension after the final cycle. For nested reactions, 1 ml of the first-round reaction was used as template. The following oligonucleotides were used for analysis of samples:

(i) 5-CAGCCTTGAAACATT-GATGG-3 (MBR)

(ii) 5-ACCTGAGGAGACGGTGACC-3 (J$_H$ Consensus)

(iii) 5-ATGCTGTGGTTGATATTTCG-3 (MBR nested)

(iv) 5-ACCTGAGGAGACGGTGACC-3 (J$_H$ nested Consensus).

Amplification products were visualized by agarose gel electrophoresis.

FACS Analysis

SK-BR3 cells were pre-loaded by incubating them in calcein AM and then seeded into normal peripheral blood mononuclear cells at a final frequency of 2%. DACS was performed as described below using the mouse monoclonal antibody to human Her-2/Neu. Aliquots of the experimental samples were analyzed by FACS analysis using the LYSYS II program. For the analysis 100,000 events were collected for each sample.

Density Adjusted Cell Sorting

Peripheral blood progenitor cells (PBPC) and buffy coats were obtained from the Bone Marrow Transplantation Laboratory at the Stanford University School of Medicine, Palo Alto, Calif. and from the Stanford University Blood Bank, Palo Alto, Calif. Monoclonal antibodies to CD9, CD10, CD19 and CD20 were obtained from Caltag Laboratories (So. San Francisco, Calif.). The anti-CD20 mAb (clone IF5) and the anti-human Her2/Neu mAb (HB 8694, 520C9) and the SK-BR3 adenocarcinoma cell line were obtained from the ATCC (Rockville, Md.). Fluorescein isothiocyanate (FITC) conjugated mouse IgG1 and mouse anti-human CD45 as well as phycoerythrin (PE) conjugated mouse IgG1 and mouse anti-human CD34 antibodies were obtained from Becton Dickinson, Inc (San Jose, Calif.). The DACS procedure and flow cytometric analysis of samples was performed as described in Example 2, above.

Purging and Electrophoretic Analysis of Peripheral Blood Cells

A Peripheral blood buffy coat, spiked (5%) with the t(14;18)+ B cell lymphoma cell line SUDHL-4, was incubated with an anti-B cell mAb cocktail specific for CD9, CD10, CD19 and CD20 cells. After washing, the cell mixture was incubated with GAM-IgG coated DACS beads at a 8:1 bead:cell ratio and then loaded onto OCS suspension at densities ranging from 1.0605 to 1.0720, with comparable results. Following centrifugation for 30 minutes at 850 g, DNA was prepared from the cells at the interface and analysed by standard gel electrophoretic methods at different concentrations (0.1 mg, 0.1 mg, 0.01 mg, 0.001 mg) by two rounds of PCR using t(14;18) specific primers, as shown in FIG. 24 (Lane 5). The number of t(14;18) translocations was furthermore determined by limiting dilution PCR. As control, the same protocol was implied on un-spiked cells (Lane 1), SUDHL-4 spiked sample (Lane 2) and SUDHL-4 spiked sample treated with DACS beads without prior incubation with the anti-B cell mAbs cocktail (Lane 4).

Centrifugation of the cell mixture over OCS suspension did not result in a reduction of the PCR signal (Lane 3). Whereas the DACS beads alone appear to induce a small reduction of the PCR signal (Lane 4), the PCR signal was completely absent in the SUDHL-4 spiked sample that was treated with both the anti-B cell mAb cocktail and the DACS beads (Lane 5). The determination of the number of t(14;18) translocations by limiting dilition PCR, showed that in the latter experimental group the number of SUDHL-4 cells was reduced by 2–3 logs (100–1000-fold). Preliminary experiments indicate that an additional round of DACS in this context further decreases the number of SUDHL-4 cells by approximately an additional log (data not shown).

All publications cited herein are incorporated by reference in their entirety. While the invention has been described with reference to specific methods and embodiments, it will be appreciated that various modifications and changes may be made without departing from the invention.

Example 6

Isolation of Dendritic Cells

Buffy coats prepared from one unit of blood from HLA-A0201 positive volunteer healthy donors are obtained from the Stanford University Blood Center (Stanford, Calif.). Cells are harvested from the leukopacs, diluted to 60 mL using $Ca^{++}/Mg^{++}$ free phosphate buffered saline (D-PBS; Gibco Laboratories, Grand Island, N.Y.) and layered over two 15 mL columns of OCS separation medium (density 1.0720 gr/ml, pH 7.4, 280 mOsm/kg $H_2O$) in 50 mL centrifuge tubes, preferably cell-trap tubes. The tubes are centrifuged at 1000×g for 35 minutes at room temperature. The centrifuge run is allowed to stop without braking and the peripheral blood mononuclear cells (PBMC), present at the interface, are harvested.

PBMC are resuspended in D-PBS, centrifuged once at 650×g for 10 minutes and twice more at 200×g for 5 minutes to remove platelets. Platelet-depleted PBMC are resuspended in 60 mL of D-PBS, layered on top of two columns of 15 mL of OCS (density 1.0610 gr/ml, 280 mOsm/kg $H_2O$) in a cell-trap tube of the present invention and centrifuged at 650×g for 25 minutes at 4° C. without braking. The resulting interface (primarily monocytes) and pellet cells (primarily lymphocytes) are harvested and washed with D-PBS by centrifugation at room temperature (once at 650×g for 10 minutes and twice thereafter at 200×g for 5 minutes).

In instances where the dendritic cells are used to generate peptide-specific cytotoxic T lymphocytes (CTL) for purposes of elucidating their antigen presentation function, the interface fraction (mostly monocytes) is resuspended in cold pooled human AB serum (Irvine Scientific, Santa Ana, Calif.) to which an equal volume of 80% AB serum 20% dimethyl sulfoxide (DMSO) (Sigma Chemical Company, St. Louis, Mo.) is added dropwise. The resulting cell suspension is aliquoted into cryovials and frozen in liquid nitrogen. The monocytes can be used for restimulation of CTL for expansion.

The pellet fraction is resuspended in 100 mL of AB Culture Medium, inoculated into two T-75 tissue culture flasks and cultured in a humidified 5% $CO_2$ incubator for 40 hours. Following the incubation, the non adherent cells are harvested by moderate pipeting, washed and resuspended at a concentration of $2–5\times10^6$ cells/mL in AB Culture Medium. The cell suspension is overlayered over four columns of 4.0 mL OCS separation medium (density 1.0565 gr/ml, pH 7.4, 280 mOsm/kg $H_2O$), in AB Culture Medium and centrifuged at 650×g for 20 minutes at room temperature without braking.

The interface and pellet cells are harvested and washed in AB Culture Medium (Basal RPMI-1640 medium, Gibco Laboratories, Grand Island, N.Y.) by centrifugation once at 650×g for 10 minutes and twice thereafter at 200×g for 5 minutes each at room temperature. The yield and viability of both cell fractions is estimated by counting on a hemocytometer using trypan blue exclusion.

The purity of dendritic cells in the interface fraction is quantified following analysis on a flow cytometer (FACS). Dendritic cells are characterized as negative for cell phenotype markers CD3 (T lymphocytes), CD14 (monocytes), CD16 (NK cells) and CD20 (B-cells) and positive for HLA class II expression using dual staining with HLA-DR (on the FITC channel) and a cocktail of CD3, CD14, CD16, CD20 (on the PE channel). Dual staining with IgG2a on both the FITC and PE channels can be used as isotype control.

The morphology of the cells can also be evaluated using photomicroscopy. The DC enriched fraction contains large sized veiled cells with cytoplasmic processes extending from the cell surface, features characteristic of DC.

It is claimed:

1. A cell-separation apparatus, comprising:

a centrifugation device having side walls and a closed bottom, a constriction member disposed within the device, said constriction member positioned and constructed to retain fluid in the bottom portion of the device below the constriction member, when the device is inverted, a closed top, at least a first and a second port in said top, said first port positioned for introduction of fluid material into said device, a closed fluid channel communicating between said second port and the bottom of the device below said constriction member, and a cell separation medium contained in the bottom portion of the device and extending above said constriction member to a level above an opening formed by said constriction member, such that cells which are captured at an interface between the cell-separation medium and a lower-density medium, after centrifugation, are discharged with the lower-density medium when the device is inverted.

2. The apparatus of claim 1, wherein said constriction member defines one or more downwardly sloped surfaces having lower edge regions defining a constricted opening.

3. The apparatus of claim 1, wherein said constriction element is an annulus having a central constricted opening.

4. The apparatus of claim 3, wherein said annulus is constructed for forced fit into the device at a selected device level.

5. The apparatus of claim 1, wherein said constriction member defines a plurality of openings.

6. The apparatus of claim 1, for further use in culturing cells, wherein said cell separation medium is a physiological cell growth medium.

7. The apparatus of claim 1, for use in enriching a selected rare blood cell from a cell mixture, wherein said cell separation medium is characterized by a specific density within about ±0.0005 of the specific density of the selected cell.

8. The apparatus of claim 7, wherein the selected rare blood cell is a CD34+ cell, the cell mixture is derived from bone marrow, and the cell separation medium has a specific density of 1.0685±0.0005 gr/ml.

9. The apparatus of claim 7, wherein the selected rare blood cell is a nucleated fetal cell, the cell mixture is derived from maternal blood, and the cell separation medium has a specific density of 1.0720±0.005 gr/ml.

10. The apparatus of claim 7, wherein the selected rare blood cell is a tumor cell, the cell mixture is derived from blood or bone marrow, and wherein the cell separation medium has a specific density selected from the range 1.0490–1.0580 gr/ml.

11. The apparatus of claim 7, wherein the selected rare blood cell is a breast tumor cell, the cell mixture is derived from blood or bone marrow, and wherein the cell separation medium has a specific density selected from the range 1.0490–1.0580 gr/ml.

12. The apparatus of claim 7, wherein the selected rare blood cell is a dendritic cell, and wherein said cell separation medium has a specific density selected from the group consisting of 1.0720 gr/ml, 1.0610 gr/ml and 1.0565 gr/ml.

13. The apparatus of claim 7, wherein the selected rare blood cell is a cylotoxic T lymphocyte wherein said cell separation medium has a specific density selected from the group consisting of 1.0720 gr/ml, 1.0610 gr/ml and 1.0565 gr/ml.

14. The apparatus of claim 7, wherein the selected rare blood cell is a natural killer cell, and wherein said cell separation medium has a specific density of 1.0605±0.0005 gr/ml.

15. The apparatus of claim 7, wherein the selected rare blood cell is a natural suppressor cell, and wherein said cell separation medium has a specific density of 1.0605±0.0005 gr/ml.

16. A method of enriching a selected cell from a cell mixture containing one or more other cell types with densities different from that of the selected cell type, comprising
adding the cell mixture to a centrifugation device having side walls and a closed bottom,
a constriction member disposed within the device, said constriction member positioned and constructed to retain fluid in the bottom portion of the device below the constriction member, when the device is inverted,
a closed top,
at least a first and a second port in said top, said first port positioned for introduction of fluid material into said device,
a closed fluid channel communicating between said second port and the bottom of the device below said constriction member, and
a cell separation medium contained in the bottom portion of the device and extending above said constriction member to a level above an opening formed by said constriction member, such that cells which are captured at an interface between the cell-separation medium and a lower-density medium, after centrifugation, are discharged with the lower-density medium when the device is inverted;
centrifuging said centrifugation device at a gravitational force sufficient to pellet cells having specific densities greater than the specific density of the density gradient material in said device; and
collecting from said device a cell fraction containing the selected cell.

17. The method of claim 16, wherein said cell separation medium has a specific density that is within ±0.0005 gr/ml of the specific density of the selected cell type and said collecting is by decantation from the device of medium present in the upper portion of the device.

18. The method of claim 16, wherein said selected cell fraction is collected from the lower portion of the device.

19. The method of claim 16, wherein said selected cell is a nucleated fetal cell, said cell mixture also contains maternal blood cells, and said cell separation medium is isotonic with the fetal cells and has a specific density of 1.0720±0.0002 gr/ml.

20. The method of claim 16, wherein said selected cell is a breast tumor cell and said cell separation medium is isotonic with said breast tumor cells and has a specific density selected from the range 1.0490–1.0580 gr/ml.

21. The method of claim 16, wherein said selected cell is a natural killer cell and said cell separation medium is isotonic with said natural killer cells and has a specific density of 1.0605±0.0005 gr/ml.

22. The method of claim 16, wherein said selected cell is a natural suppressor cell and said cell separation medium is isotonic with said natural suppressor cells and has a specific density of 1.0605±0.0005 gr/ml.

23. The method of claim 16, wherein said selected cell is a hematopoietic progenitor CD34+ cell derived from bone marrow, and said cell separation medium is isotonic with said CD34+ cells and has a specific density of 1.0605±0.0005 gr/ml.

24. The method of claim 16, further comprising prior to said centrifuging, incubating said cell mixture with a cell type-specific binding agent directly or indirectly linked to carrier particles, said particles having a specific density that is at least 0.001 gr/ml greater than the specific density of said cell separation medium.

25. The method of claim 24, wherein said cell separation medium has a specific density that is within about 0.0005 gr/ml of the specific density of the selected cell type.

26. The method of claim 24, wherein said cell type specific binding agent binds a tumor cell antigen.

27. The method of claim 26, wherein the tumor cell antigen is selected from the group consisting of CD-9, CD-10, CD-19 and CD-20.

28. The method of claim 26, wherein the tumor cell antigen is selected from the group consisting of Her2/Neu and estrogen receptor.

29. The method of claim 24, wherein said cell-type specific binding agent binds to a cell type other than said selected cell type.

30. The method of claim 29, for use in depleting T-cell lymphocytes from a mixture that includes hematopoietic progenitor cells, wherein the cell binding agent is selected from the group consisting of anti-CD3, anti-CD4 and anti-CD8 mouse monoclonal antibodies and the specific density of the cell separation medium is 1.0605±0.0005 gr/ml.

31. The method of claim 16, wherein said selected cell is a dendritic cell and said cell separation medium is isotonic with said dendritie cells and has a specific density selected from the group consisting of 1.0720 gr/ml, 1.0610 gr/ml and 1.0565 gr/ml.

32. The method of claim 16, wherein said selected cell is a cytotoxic T lymphocyte and said cell separation medium is isotonic with said cytotoxic T lymphocytes and has a specific density selected from the group consisting of 1.0720 gr/ml, 1.0610 gr/ml and 1.0565 gr/ml.

33. A method of enriching a natural killer cell from a cell mixture, comprising layering the cell mixture onto a cell separation medium in a centrifuge tube, said cell separation medium characterized by a specific density of 1.0605±0.0005 gr/ml isotonicity with the natural killer cell, said tube having side walls, a closed bottom, and a constriction member disposed within the tube, wherein said constriction member is positioned and constructed to retain fluid in the bottom portion of the tube below the constriction member when the tube is inverted, said cell separation medium contained in the bottom portion of the tube and extending above said constriction member to a level above an opening formed by said constriction member, such that cells which are captured at an interface between the cell-separation medium and a lower-density medium, after centrifugation, are discharged with the lower-density medium when the tube is inverted, centrifuging said centrifuge tube at a gravitational force sufficient to pellet cells having a specific density of greater than said specific density of said separation medium, and collecting the natural killer cell from the upper portion of said tube.

34. A method of enriching a natural suppressor cell from a cell mixture, comprising layering the cell mixture onto a cell separation medium in a centrifuge tube, said cell separation medium characterized by a specific density of 1.0605±0.0005 gr/ml isotonicity with the natural suppressor cell, said tube having side walls, a closed bottom, and a constriction member disposed within the tube, wherein said constriction member is positioned and constructed to retain fluid in the bottom portion of the tube below the constriction member when the tube is inverted, said cell separation medium contained in the bottom portion of the tube and extending above said constriction member to a level above an opening formed by said constriction member, such that cells which are captured at an interface between the cell-separation medium and a lower-density medium, after centrifugation, are discharged with the lower-density medium when the tube is inverted, centrifuging said centrifuge tube at a gravitational force sufficient to pellet cells having a specific density of greater than said specific density of said separation medium, and collecting the natural killer cell from the upper portion of said tube.

35. A method of enriching a dendritic cell from a cell mixture, comprising layering the cell mixture into a cell separation medium in a centrifuge tube, said cell separation medium characterized by a specific density selected from the group consisting of 1.0720±0.0005 gr/ml, 1.0610±0.0005 gr/ml and 1.0565±0.0005 gr/ml and isotonicity with the dendritic cell, said tube having side walls, a closed bottom, and a constriction member disposed within the tube, wherein said constriction member is positioned and constructed to retain fluid in the bottom portion of the tube below the constriction member when the tube is inverted, said cell separation medium contained in the bottom portion of the tube and extending above said constriction member to a level above an opening formed by said constriction member, such that cells which are captured at an interface between the cell-separation medium and a lower-density medium, after centrifugation, are discharged with the lower density medium when the tube is inverted, centrifuging said centrifuge tube at a gravitational force sufficient to pellet cells having a specific density of greater than said specific density of said separation medium, and collecting said dendritic cell from the upper portion of said tube.

36. A method of enriching a cytotoxic T lymphocyte from a cell mixture, comprising layering the cell mixture onto a cell separation medium in a centrifuge tube, said cell separation medium characterized by a specific density selected from the group consisting of 1.0720±0.0005 gr/ml, 1.0610±0.0005 gr/ml and 1.0565±0.0005 gr/ml and isotonicity with the T lymphocyte, said tube having side walls, a closed bottom, and a constriction member disposed within the tube, wherein said constriction member is positioned and constructed to retain fluid in the bottom portion of the tube below the constriction member when the tube is inverted, said cell separation medium contained in the bottom portion of the tube and extending above said constriction member to a level above an opening formed by said constriction member, such that cells which are captured at an interface between the cell-separation medium and a lower-density medium, after centrifugation, are discharged with the lower-density medium when the tube is inverted, centrifuging said centrifuge tube at a gravitational force sufficient to pellet cells having a specific density of greater than said specific density of said separation medium, and collecting said T lymphocyte from the upper portion of said tube.

37. A method of enriching a hematopoietic progenitor $CD34^+$ cell from cell mixture derived from bone marrow, comprising layering the cell mixture onto a cell separation medium in a centrifuge tube, said cell separation medium characterized by a specific density of 1.0685±0.0005 gr/ml and isotonicity with the hematopoietic progenitor $CD34^+$ cell, said tube having side walls, a closed bottom, and a constriction member disclosed within the tube, wherein said constriction member is positioned and constructed to retain fluid in the bottom portion of the tube below the constriction member when the tube is inverted, said cell separation medium contained in the bottom portion of the tube and extending above said constriction member to a level above an opening formed by said constriction member, that cells which are captured at an interface between the cell-separation medium and a lower-density medium, after centrifugation, are discharged with the lower-density medium when the tube is inverted, centrifuging said centrifuge tube at a gravitational force sufficient to pellet cells having a specific density of greater than said specific density of said separation medium, and collecting the hematopoietic progenitor CD34$^+$ cell from the upper portion of said tube.

38. A method of depleting a T-cell lymphocyte from a cell mixture that also contains hematopoietic progenitor CD34$^+$ cells, comprising layering the cell mixture onto a cell separation medium in a centrifuge tube, said cell separation medium characterized by a specific density of less than $1.0700\pm0.0005$ gr/ml, said tube having side walls, a closed bottom, and a constriction member disposed within the tube, wherein said constriction member is positioned and constructed to retain fluid in the bottom portion of the tube below the constriction member when the tube is inverted, said cell separation medium contained in the bottom portion of the tube and extending above said constriction member to a level above an opening formed by said constriction member, such that cells which are captured at an interface between the cell-separation medium and a lower-density medium, after centrifugation, are discharged with the lower-density medium when the tube is inverted, centrifuging said centrifuge tube at a gravitational force sufficient to pellet cells having a specific density of greater than said specific density of said separation medium.

39. The method of claim 38, wherein said cell separation medium has a specific density that is selected from the group consisting of $1.0605\pm0.0005$ gr/ml, $1.0650\pm0.0005$ gr/ml, and $1.0685\pm0.0005$ gr/ml.

40. A kit, comprising:

a) a centrifugation apparatus, which includes:
   (i) a centrifugation device having side walls and a closed bottom;
   (ii) a constriction member disposed within the device, said constriction member positioned and constructed to retain fluid in the bottom portion of the device below the constriction member, when the device is inverted; and
   (iii) a cell separation medium contained in the bottom portion of the device and extending above said constriction member to a level above an opening formed by said constriction member, such that cells which are captured at an interface between the cell-separation medium and a lower-density medium, after centrifugation, are discharged with the lower-density medium when the device is inverted; and b) a cell type-specific binding agent directly or indirectly linked to carrier particles, said particles having a specific density that is at least 0.001 gr/ml greater than the specific density of said cell separation medium.

41. The kit of claim 40, wherein said centrifugation device further comprises:

a closed top;

at least a first and a second port in said top, said first port positioned for introduction of fluid material into said device; and a closed fluid channel communicating between said second port and the bottom of the device below said constriction member.

* * * * *